(12) United States Patent
Grobler et al.

(10) Patent No.: US 6,274,311 B1
(45) Date of Patent: Aug. 14, 2001

(54) METHOD AND NUCLEOTIDE SEQUENCE FOR TRANSFORMING MICROORGANISMS

(75) Inventors: Jandre Grobler, Plumstead (ZA); Aldis Krizus, Toronto (CA); Chauanpit Osothsilp-Deeknamakul, Klongton (TH); Isak S. Pretorius; Hendrick J. Jansen Van Vuuren, both of Stellenbosch (ZA); Ronald E. Subden, Guelph (CA)

(73) Assignees: University of Guelph, Guelph (CA); University of Stellenbosch, Stellenbosch (ZA)

( * ) Notice: Subject to any disclaimer, the term of this patent is extended or adjusted under 35 U.S.C. 154(b) by 0 days.

(21) Appl. No.: 08/952,365
(22) PCT Filed: May 17, 1996
(86) PCT No.: PCT/CA96/00320
 § 371 Date: May 28, 1998
 § 102(e) Date: May 28, 1998
(87) PCT Pub. No.: WO96/36715
 PCT Pub. Date: Nov. 21, 1996

(30) Foreign Application Priority Data

May 18, 1995 (ZA) ..................................................... 95/4072

(51) Int. Cl.[7] ............................. C07H 21/04; C12Q 1/68; C12N 1/18; C07K 1/00
(52) U.S. Cl. ................... 435/6; 435/254.11; 435/254.21; 435/254.2; 435/69.1; 435/320.1; 530/350; 536/23.7; 536/23.74
(58) Field of Search ............................... 435/183, 6, 69.1, 435/320.1, 254.11, 254.2, 254.21; 530/350; 536/23.7, 23.74

(56) References Cited

U.S. PATENT DOCUMENTS

| 4,472,502 | 9/1984 | Hodges et al. | 435/172.3 |
| 5,422,267 | 6/1995 | Yocum et al. | 435/254.21 |
| 5,587,304 | 12/1996 | Barre et al. | 435/139 |

OTHER PUBLICATIONS

Chevallier et al. "Expression of the cloned uracil permease gene of *Saccharomyces cerveciae* in heterologous membrane" EMBO J. 1 (3), 375–377, 1982.*

Grobler et al., Yeast, vol. 11:1485–1491, 1995.

LaBarre et al., Applied and Enviromental Microbiology, vol. 62, No. 4, p. 1274–1282, Apr. 1996.

Kaplan, Ronald S. and Pedersen, Peter L., The Journal of Biological Chemistry, vol. 260, No. 18, p. 10293–10298, Aug. 1985.

Jiang, J. et al., Journal of Bacteriology, vol. 171, No. 10, p. 5244–5253, Oct. 1989.

Lautenbach, A. and Subden, R.E., Microbios, vol. 39:29–39, 1984.

\* cited by examiner

*Primary Examiner*—Nashaat T. Nashed
(74) *Attorney, Agent, or Firm*—Bereskin & Parr; Micheline Gravelle

(57) ABSTRACT

An isolated nucleic acid molecule is provided which contains a sequence which encodes a protein which mediates the uptake of L-malate, succinate, and malonate, and expression vectors and host cells containing the nucleic acid molecules. The nucleic acid molecules are used to transform cells for use in mediating malate, succinic acid or malonate uptake in particular malate uptake during the fermentation of wines.

34 Claims, 15 Drawing Sheets

FIGURE 3

```
-378                                          TGATCACTATTTGTTTGTTCTATTTTTGTTTTCTTTTACTTGTTTGCTACACAAAATAAGCTTATTTGTTGCTGCACT
-300  AGACTTTTTGTTTGATTTCTCATCCTACTTCTGTATCGGCAGTTTGCTCATTTACTAAGACTAGCAACAGCCAGTCATTCATTTTTTACACTCTCTATCA
-200  TTTTTTATTTTCATCACGATAACTAACATGTGCGATTAGACTCACAGATAAATTGCTAGCAATTGGTTGTCTCTTTCCTTCCTCCGTCTTTTCCTTTTTG
-100  TTCCTTTTTCTCCTTATATTTATATTTATATTTATATTCATTCTTCATTTTCTCTCTTGGCCACTATTTTTTTTTTTAATTCCCCTTTATCTCTCGATTCGAC
   1  ATGGGTGAACTCAAGGAAATCTTGAAACAGAGGTATCATGAGTTGCTTGACTGGAATGTCAAAGCCCCTCATGTCCCTCTCAGTCAACGACTGAAGCATT
      M  G  E  L  K  E  I  L  K  Q  R  Y  H  E  L  L  D  W  N  V  K  A  P  H  V  P  L  S  Q  R  L  K  H  F   34
 101  TTACATGGTCTTGGTTTGCATGTACTATGGCAACTGGTGGTGTTGGTTTGATTATTGGTTCTTTCCCCTTTCGATTTTATGGTCTTAATACAATTGGCAA
      T  W │S  W  F  A  C  T  M  A  T  G  G  V  G  L  I  I  G  S  F  P  F│ R  F  Y  G  L  N  T │I  G  K    67
 201  AATTGTTTATATTCTTCAAATCTTTTTGTTTTCTCTCTTTGGATCATGCATGCTTTTTCGCTTTATTAAATATCCTTCAACTATCAAGGATTCCTGGAAC
      │I  V  Y  I  L  Q  I  F  L  F  S  L  F  G  S  C  M  L│ F  R  F  I  K  Y  P  S  T  I  K  D  S  W  N   100
 301  CATCATTTGGAAAAGCTTTTCATTGCTACTTGTCTTCTTTCAATATCCACGTTCATCGACATGCTTGCCATATACGCCTATCCTGATACCGGCGAGTGGA
      H  H  L  E  K │L  F  I  A  T  C  L  L  S  I  S  T  F  I  D  M  L  A  I  Y  A│ Y  P  D  T  G  E  W  M   134
 401  TGGTGTGGGTCATTCGAATCCTTTATTACATTTACGTTGCAGTATCCTTTATATACTGCGTAATGGCTTTTTTTACAATTTTCAACAACCATGTATATAC
      V  W  V  I  R │I  L  Y  Y  I  Y  V  A  V  S  F  I  Y  C  V  M  A  F  F  T  I│ F  N  N  H  V  Y  T    167
 501  CATTGAAACCGCATCTCCTGCTTGGATTCTTCCTATTTTCCCTCCTATGATTTGTGGTGTCATTGCTGGCGCCGTCAATTCTACACAACCCGCTCATCAA
      I  E  T  A │S  P  A  W  I  L  P  I  F  P  P  M  I  C  G  V  I  A  G  A  V│(N) S  T  Q  P  A  H  Q    200
 601  TTAAAAAATATGGTTATCTTTGGTATCCTCTTTCAAGGACTTGGTTTTTGGGTTTATCTTTTACTGTTTGCCGTCAATGTCTTACGGTTTTTTACTGTAG
      L  K  N  M │V  I  F  G  I  L  F  Q  G  L  G  F  W  V  Y  L  L  L  F  A  V│ N  V  L  R  F  F  T  V  G  234
 701  GCCTGGCAAAACCCCAAGATCGACCTGGTATGTTTATGTTTGTCGGTCCACCAGCTTTCTCAGGTTTGGCCTTAATTAATATTGCGCGTGGTGCTATGGG
      L  A  K  P  Q  D  R │P  G  M  F  M  F  V  G  P  P  A  F  S  G  L  A  L  I  N  I  A│ R  G  A  M  G   267
 801  CAGTCGCCCTTATATTTTTGTTGGCGCCAACTCATCCGAGTATCTTGGTTTTGTTTCTACCTTTATGGCTATTTTTATTTGGGGTCTTGCTGCTTGGTGT
      S  R  P  Y  I  F  V  G  A (N) S  S  E  Y  L  G  F  V  S  T │F  M  A  I  F  I  W  G  L  A  A  W  C   300
 901  TACTGTCTCGCCATGGTTAGCTTTTTAGCGGGCTTTTTCACTCGAGCCCCTCTCAAGTTTGCTTGTGGATGGTTTGCATTCATTTTCCCCAACGTGGGTT
      Y  C  L  A  M  V  S  F│ L  A  G  F  F  T  R  A  P  L  K  F │A  C  G  W  F  A  F  I  F  P  N  V  G  F  334
1001  TTGTTAATTGTACCATTGAGATAGGTAAAATGATAGATTCCAAAGCTTTCCAAATGTTTGGACATATCATTGGGGTCATTCTTTGTATTCAGTGGATCCT
      V  N  C  T  I  E  I  G│ K  M  I  D  S  K  A  F  Q  M │F  G  H  I  I  G  V  I  L  C  I  Q  W  I  L    367
1101  CCTAATGTATTTAATGGTCCGTGCGTTTCTCGTCAATGATCTTTGCTATCCTGGCAAAGACGAAGATGCCCATCCTCCACCAAAACCAAATACAGGTGTC
      L  M  Y  L  M  V│ R  A  F  L  V  N  D  L  C  Y  P  G  K  D  E  D  A  H  P  P  P  K  P  N  T  G  V   400
1201  CTTAACCCTACCTTCCCACCTGAAAAAGCACCTGCATCTTTGGAAAAAGTCGATACACATGTCACATCTACTGGTGGTGAATCGGATCCTCCTAGTAGTG
      L  N  P  T  F  P  P  E  K  A  P  A  S  L  E  K  V  D  T  H  V  T  S (T) G  G  E  S  D  P  P  S (S) E  434
1301  AACATGAAAGCGTTTAAGCTTGTATGCTTTTCCTTAATTTTTCTATAAATCTGTGTGCCCTGCTCTTAATACCATTATAGATTAATCATTTTGAATCATT
      H  E  S  V  *                                                                                        438
1401  CTGTATCTTTATTGTACTACTGGTACTAATTTTGCTTAGACATTTTTGCTCCTTCTTCTTCTTTTTGTTTAAATTATACATACCAAAATTTTGGACTTTG
1501  AATAATGGTAATTTTTGGTTGTCGTAGTGTTAAATATGTATGCGTCTTGCATATGAATCACGACGAAGGAATCAATTAAAAAATCAATCCTGTACATAAT
1601  AAAATTAAGTTTATTTATTTCATTTTATCGGATTTAATCGTCTAAAATTTATATCTTGGTCATCCAAGCTTATATCTCTTTCTACTCTTATCAGCAGCAC
1701  ACTTTAGTTATGGTTATTTGAAAACTTGTGTATAAATTCCTGGTTATAGAGAAAATGAGTATAAGACAACAAAAAAAAGCCTAGTCGGCATGCGACATGT
1801  CTCAAACATATCTTTGGCGTATTGATGAGCATCTTACACACTCACTATACGTAACAATAAAATTAAGAGGGATTTCATGACAAAAGAATACTAGAGTGAA
1901  ACCACTATGACTAAATAAAAACTGGTAAAAGGTAATTCTAAAATATTAAATCATGTATAGAAAATAGTCCAATTAATCAAGATAGCGTTGAACGTGACC
2001  TGATACTAGATTGCACAAACGAAATAAAACAATCTTGAAGTAAAAGCAATAGCACAATAAAAGAGAAGATACCTCATTTAAC
```

FIGURE 7
a
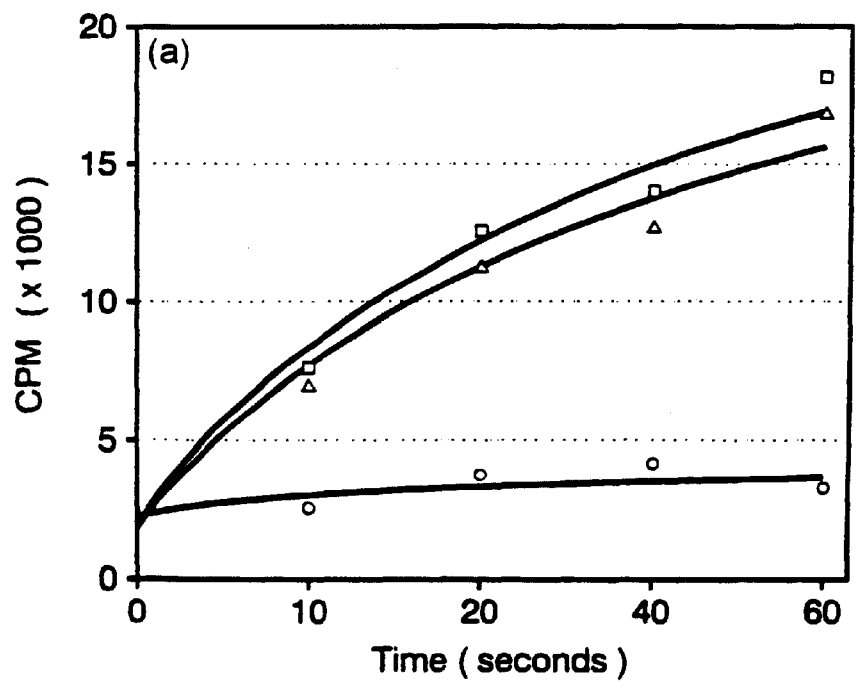
b
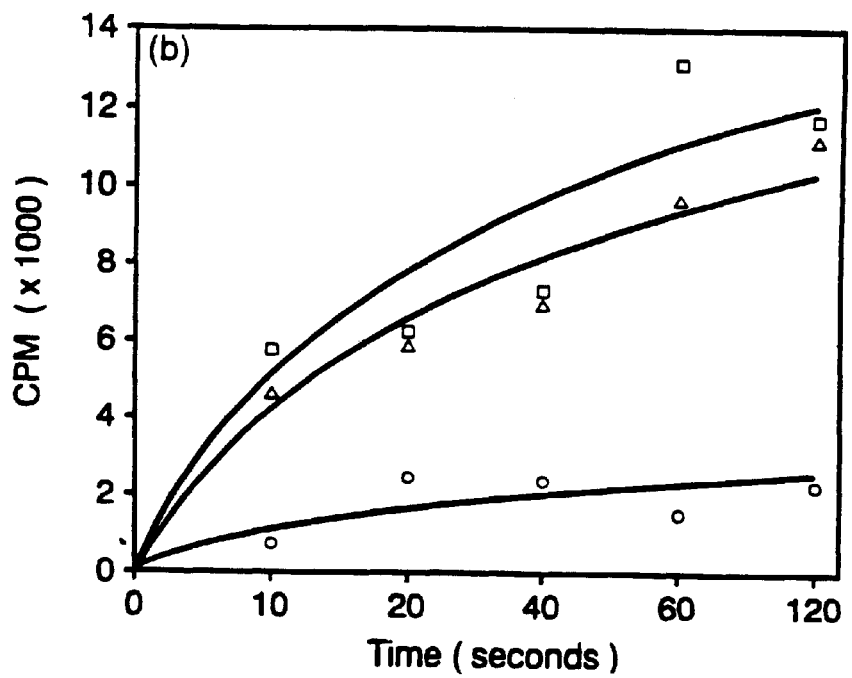

METHOD AND NUCLEOTIDE SEQUENCE FOR TRANSFORMING MICROORGANISMS

FIELD OF THE INVENTION

This invention relates to a method and nucleotide sequence for transforming microorganisms. More particularly, the invention relates to a recombinant DNA molecule, to a gene, to a polypeptide, to a transformed yeast strain, to a method of transforming a yeast strain, to a method of producing a desired polypeptide, and to a fermentation method.

BACKGROUND OF THE INVENTION

The transport of L-malic acid across the plasma membrane and its degradation in microorganisms is of considerable interest in many fields, particularly those involving fermentation by yeasts. L-malic acid may be used as a sole carbon and energy source by the yeasts *Candida sphaerica* (Corte-Real et al., 1989), *Hansenula anomala* (Corte-Real and Leao, 1990) and *Candida utilis* (Cassio and Leao, 1993). The dissociated form of malate is transported across the plasma membrane by proton symports which are inducible and subjected to glucose repression. However, in *Zygosaccharaomyces bailii* (Rodriquez and Thornton, 1990) and *Schizosaccharomyces pombe* (*S. pombe*) (Sousa et al., 1992), L-malic acid can only be metabolized in the presence of an assimilable carbon source (Osothsilp and Subden, 1986). L-malic acid is actively transported in the dissociated form whereas the undissociated acid enters the cell via simple diffusion (Baranowski and Radler, 1984; Osothsilp and Subden, 1986; Sousa et al., 1992). Competitive inhibition of initial uptake rates of L-malic acid by succinic acid, D-malic acid, faumaric acid, oxaloacetic acid, α-ketoglutaric acid, maleic acid and malonic acid strongly suggests that these acids are transported by the same carrier in *S. pombe* (Sousa et al, 1992).

Malic acid degradation is of particular interest to wineries. Wine yeast strains of *Saccharomyces cerevisiae* (*S. cerevisiae*) cannot metabolize malate in grape must efficiently and changes in the total acidity of the wine during vinification are therefore insignificant (Gao, 1995). Production of well-balanced wines requires the controlled reduction of excess malic acid, particularly in the colder viticultural regions of the world.

Chemical deacidification has been used to reduce the total acidity of wine. Chemical deacidification is typically carried out by (a) amelioration—which is essentially dilution of the malic acid with sugar water; (b) precipitation—the addition of calcium, potassium or other cations to produce an insoluble salt; or (c) masking—adding grape juice or sucrose to the finished wine to mask the sour taste of malic acid. All these methods result in residual malate which can support malolactic fermentation by contaminating bacteria unless treated with elevated doses of sulfites.

Malolactic fermentation methods for malic acid degradation rely on the conversion of L-malic acid to L-lactic acid and $CO_2$ by malolactic bacteria, for example, species of Leuconostoc, Lactobacillus, and Pediococcus. The malolactic bacteria may be found on grapes which become part of the winery microflora, or commercially available frozen or freeze-dried cultures of the bacteria may be introduced into the wine. Malolactic fermentation methods have a number of disadvantages; for example, the malolactic bacteria ferment terpenes which change the character of the wine. Control of malolactic fermentations is often difficult resulting in incomplete malolactic fermentation and subsequent bottle fermentations. Bacterial growth is also usually accompanied by the production of carbon dioxide which may result in "fizzy" wine.

Yeast strains which can degrade L-malic acid have also been used in wine fermentations. Fermentations using the fission yeast *S. pombe* which completely degrades malate to ethanol through a malo-ethanolic fermentation have been attempted. Thornton (U.S. Pat. No. 4,830,968) describes a method involving inoculating grape juice with a strain of *Saccharomyces malidevorans* which is capable of some degradation of L-malic acid under wine making conditions. However, these yeast strains (i.e. *Schizosaccharomyces pombe* and *Saccharomyces malidevorans*) are not desirable in wine making since off-flavours are produced. High density cell suspensions of several yeasts, including *S. cerevisiae* have also been used to try to increase the rate at which L-malate is degraded during fermentation (Gao, 1995).

Attempts have been made to hybridize wine yeasts with malate-metabolizing yeast strains. Protoplast fusion (Carrau et al., 1982; Svoboda, 1980, U.S. Pat. No. 5,330,774 to Carrau et al.), transformation (Lautensach and Subden, 1984; Williams et al., 1984), and other means (Fernandez, 1967; Goto et al., 1978; Kuczynski and Radler, 1982) have not been successful.

Metabolic engineering of *S. cerevisiae* strains to carry out alcoholic fermentation and malolactic or malo-ethanolic fermentation simultaneously has been explored. The malolactic gene (mleS) from *Lactobacillus delbrueckii* (Williams et al., 1984) and *Lactococcus lactis* (Ansanay et al., 1993, Denayrolles et al., 1994) have been cloned, characterized and several attempts have been made to introduce and express this gene in *S. cerevisiae*. However, recombinant strains of *S. cerevisiae* expressing the mleS gene were unable to degrade malate effectively to L-lactate (Williams et al., 1984; Ansanay et al., 1993, Denayrolles et al., 1995).

SUMMARY OF THE INVENTION

The present inventors have identified a gene in *S. pombe*, designated mae1 or malate permease gene, which encodes a dicarboxylic acid permease (referred to herein as "malate permease" or "Mae1"). This is the first molecular characterization of a dicarboxylic acid permease in a eukaryotic cell. The *S.pombe* mae1 gene encodes a single mRNA of 1.5 kb. The gene is expressed constitutively and is not subject to catabolite repression as was previously reported for the malate permease gene of *C. utilis* (Cassio and Leas, 1993) and *H. anomala* (Corte-Real and Leao, 1990). The mae1 gene was mapped to 2842 bp 5' to the MFm1 gene on Chromosome I.

Transport assays revealed that the mae1 gene encodes a malate permease involved in the transport of L-malate, succinate, and malonate. The *S. pombe* malate permease has 435 amino acid residues with a molecular weight of approximately 49 kDa.

Mae1 from *S. pombe* contains a number of well-characterized regions including two protein kinase C phosphorylation sites, a PEST region, a leucine zipper region, two hydrophillic linker regions, and ten membrane-spanning helices. In particular, a well conserved PEST region (amino acids 421–434 in FIG. 3, SEQ ID NO:2) is found at the C-terminal end, consisting of proline (P), glutamic acid (E), serine (S), threonine (T) and to a lesser extent aspartic acid. A leucine zipper motif (amino acids 214 to 235 in FIG. 3, SEQ ID NO:2), consisting of four leucine residues spaced by 6 amino acids, is located between membrane-spanning domains six and seven. Protein kinase C phosphorylation sites were found at positions 28: phvplSqrlkh and at position 94: ikypsTikdsw. Mae1 from *S.pombe* also contains three potential N-linked glycosylation sites located at amino acids 193, 277 and 336 (FIG. 3, SEQ ID NO:2).

The present inventors have introduced an efficient pathway for malate degradation in *S. cerevisiae* by cloning and expressing the *S. pombe* malate permease (mae1) and malic enzyme (mae2) genes in this yeast. Recombinant strains efficiently degraded 8 g/l of malate within 7 days. A recombinant strain of *S. cerevisiae* containing both the *S. pombe* mae 1 and *L. lactis* mleS genes was also shown to efficiently and rapidly degrade L-malate to L-lactate in grape must in a significantly short period of time. The present inventors have shown the efficacy of these recombinant strains (mae1, mae2, and mae1mleS) for maloethanolic fermentation, and malolactic fermentation, respectively.

The present invention therefore provides an isolated nucleic acid molecule comprising a sequence which encodes a polypeptide which mediates the uptake of L-malate, succinate, and malonate. The nucleic acid molecule may comprise the malate permease (mae1) gene from *S. pombe*. In particular, the nucleic acid molecule is characterized as encoding a protein which mediates uptake of L-malate, succinate, and malonate and has a PEST region, and a leucine zipper motif.

In an embodiment of the invention, the isolated nucleic acid molecule comprises (i) a nucleic acid sequence encoding a protein having the amino acid sequence shown in SEQ ID NO: 2 or FIG. 3;

(ii) nucleic acid sequences complementary to (i); and (iii) a nucleic acid capable of hybridizing under stringent conditions to a nucleic acid of (i).

Preferably, the isolated nucleic acid molecule comprises (i) a nucleic acid sequence as shown in SEQ ID NO:1 or FIG. 3, wherein T can also be U;

(ii) nucleic acid sequences complementary to (i), preferably complementary to the full length nucleic acid sequence shown in SEQ ID NO: 1 or FIG. 3;

(iii) a nucleic acid capable of hybridizing under stringent conditions to a nucleic acid of (i); and (iv) a nucleic acid molecule differing from any of the nucleic acids of (i) to (iii) in codon sequences due to the degeneracy of the genetic code.

The invention also contemplates a nucleic acid molecule comprising a sequence encoding a truncation of Mae1, an analog, or a homolog of Mae1, or a truncation thereof. (Mae1 and truncations, analogs and homologs of Mae1 are also collectively referred to herein as "Mae1 protein" or "Mae1 proteins").

The invention also provides a nucleic molecule encoding a fusion protein comprising a Mae1 protein and a heterologous protein or peptide, preferably a selectable marker, or a protein involved in the metabolism of L-malate, succinate, or malonate, such as malic enzyme or malolactic enzyme.

The nucleic acid molecules of the invention may be inserted into an appropriate expression vector, i.e. a vector which contains the necessary elements for the transcription and translation of the inserted coding sequence. Accordingly, expression vectors adapted for transformation of a host cell may be constructed which comprise a nucleic acid molecule of the invention and one or more transcription and translation elements operatively linked to the nucleic acid molecule.

The expression vector can be used to prepare transformed host cells expressing a Mae1 protein. Therefore, the invention further provides host cells containing an expression vector of the invention.

In accordance with an embodiment of the invention, a yeast strain is provided which incorporates DNA material comprising:

a nucleotide sequence which encodes a functional polypeptide or intermediate therefor, or encodes at least as much of an amino acid sequence thereof as will provide malate permease activity for the application in which the malate permease is intended for use, a promoter for promoting transcription of the nucleotide sequence and driving expression of the malate permease, and a terminator for terminating transcription of the nucleotide sequence.

The invention further provides a method for preparing a Mae1 protein utilizing the purified and isolated nucleic acid molecules of the invention. In an embodiment a method for preparing a Mae1 protein is provided comprising (a) transferring a recombinant expression vector of the invention into a host cell; (b) selecting transformed host cells from untransformed host cells; (c) culturing a selected transformed host cell under conditions which allow expression of the Mae1 protein; and (d) isolating the Mae1 protein.

According to an embodiment of the invention, there is provided a method of producing malate permease, which includes cultivating a yeast strain transformed by DNA material which includes a nucleotide sequence which encodes a functional malate permease or intermediate therefor, or encodes at least as much of an amino acid sequence thereof as will provide malate permease activity for the application in which the malate permease is intended for use, and which further encodes a promoter for promoting transcription of the nucleotide sequence and driving expression of the malate permease, and a terminator for terminating transcription of the nucleotide sequence.

The invention further broadly contemplates an isolated Mae1 protein which mediates the uptake of L-malate, succinate, and malonate. In an embodiment, the protein is characterized in that it has part or all of the primary structural conformation (ie. continuous sequence of amino acid residues) and the enzymatic activity of Mae1 from *S. pombe*. In particular, a purified Mae1 protein is provided which has the amino acid sequence as shown in SEQ ID NO:2 or FIG. 3. The invention also includes truncations of the protein and analogs, homologs, and isoforms of the protein and truncations thereof (i.e., Mae1 proteins).

The Mae1 proteins of the invention may be conjugated with other molecules, such as peptides or proteins, to prepare fusion proteins. This may be accomplished, for example, by the synthesis of N-terminal or C-terminal fusion proteins.

The invention further contemplates antibodies having specificity against an epitope of a Mae1 protein of the invention. Antibodies may be labelled with a detectable substance and used to detect Mae1 proteins.

The invention also permits the construction of nucleotide probes which are unique to the nucleic acid molecules of the invention and accordingly to Mae1 proteins. Therefore, the invention also relates to a probe comprising a sequence encoding a Mae1 protein. The probe may be labelled, for example, with a detectable substance and it may be used to select from a mixture of nucleotide sequences a nucleotide sequence coding for a protein which displays one or more of the properties of Mae1.

The identification and sequencing of a gene responsible for the active transport of L-malate, succinate, and malonate permits one skilled in the art to mediate malate, succinate and malonate uptake in cells in various technological applications.

A Mae1 protein of the invention may be used to identify substances which affect the activity of the protein, and thus may be useful in mediating transport of L-malate, succinate, or malonate in a cell preferably a microorganism or plant cell. The invention therefore provides a method for identifying a substance that mediates transport of L-malate, succinate or malonate comprising incubating a Mae1 protein of the invention with a substrate of the Mae1 protein, and a test substance which is suspected of affecting the activity of the Mae1 protein, and determining the effect of the substance by comparing to a control.

The invention also relates to a method of providing a cell, preferably a microorganism or plant cell, with the capability of transporting malate comprising transforming the cell with a DNA fragment or nucleic acid molecule comprising a nucleotide sequence which encodes a polypeptide which mediates the uptake of malate. Preferably the cell is transformed with a nucleic acid molecule encoding a Mae1 protein of the invention. According to a specific embodiment of the invention there is provided a method of providing a yeast strain with the capability of efficiently transporting malate, said method comprising transforming the yeast strain with a nucleotide sequence which encodes a functional polypeptide or intermediate therefor, or encodes at least as much of an amino acid sequence thereof as will mediate the uptake of malate. The transformation of the cells may provide the cells with the capability of efficiently degrading malate, succinate, or malonate.

The nucleic acid molecules of the invention may be used to mediate malate uptake in yeast strains in many industrial applications such as wine-making. Therefore, the methods of the invention may be used to transform a yeast or wine yeast of the genus Saccharomyces, preferably *Saccharomyces cerevisiae* or *S. bayanus*, to transport malate and thereby enable the yeast to efficiently degrade malate. More particularly, the transformation of *S. cerevisiae* may be effected by cloning the malate permease (mae1) gene from the yeast *S. pombe* into the *S. cerevisiae* yeast strain.

The invention further provides, broadly, a method of degrading malate which includes cultivating, in the presence of a supply of malate, a microorganism which has been transformed with a nucleotide sequence which encodes a polypeptide that mediates the uptake of malate.

More specifically, according to the invention there is further provided a method of degrading malate which includes cultivating in the presence of a supply of malate, a yeast strain which has been transformed by introducing into the yeast strain, a nucleic acid molecule having a sequence which encodes malate permease or an intermediate therefor, or encodes at least as much of an amino acid sequence thereof as will mediate the uptake of malate, and which includes a promoter and a terminator for promoting and terminating transcription, and hence expression of the malate permease gene.

The invention extends, yet further, to a method of degrading malate during fermentation of wine, which method includes, cultivating, in grape musts which contain a supply of malate, a yeast strain transformed by recombinant DNA material which includes a nucleotide sequence which encodes a functional malate permease or intermediate therefor, or encodes at least as much of an amino acid sequence thereof as will provide malate permease activity, and which further encodes a promoter for promoting transcription of the nucleotide sequence and driving expression of the nucleotide sequence, and a terminator to end transcription of the nucleotide sequence resulting in a permease to transport malate into the yeast cells.

Thus according to the invention there is provided a method of fermenting wine, which includes cultivating, in a wine fermentation medium which includes grape must containing a supply of malate, a yeast strain transformed by recombinant DNA material which includes a nucleotide sequence which encodes a functional malate permease or intermediate therefor, or encodes at least as much of an amino acid sequence thereof as will provide malate permease activity, and which further encodes a promoter for promoting transcription of the nucleotide sequence and driving expression of the nucleotide sequence, and a terminator to end transcription of the nucleotide sequence, resulting in a permease to transport malate into the yeast cells.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 3 shows nucleotide sequence (SEQ ID NO:1) and deduced amino acid sequence (SEQ ID NO:2) of the mae1 gene, the nucleotides being numbered on the left and the amino acids, designated by standard single-letter codes, being numbered on the right;

FIG. 7 shows uptake of (a) [$^{14}$C] L-malic acid and (b) [$^{14}$C] succinic acid by the wild-type (Δ), mae1 mutant (O) and complemented mutant (□);

DETAILED DESCRIPTION OF THE INVENTION

Figure 1:
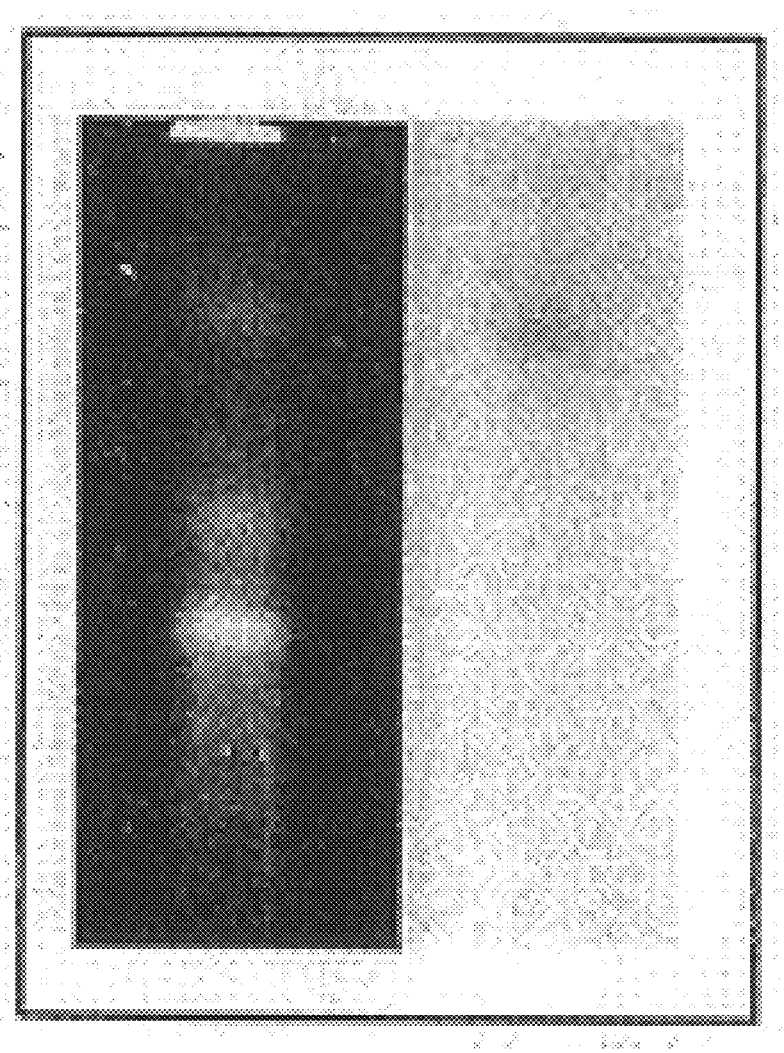
FIG. 1 shows chromosomal blotting of the mae1 gene wherein *S. pombe* chromosomes were separated on a CHEF gel (left) and probed with a labelled internal Nsi1/Xho1 fragment of mae1 (right)

I. Nucleic Acid Molecules of the Invention

As hereinbefore mentioned, the invention provides an isolated nucleic acid molecule having a sequence encoding a protein which mediates the uptake of L-malate, succinate, and malonate. The term "isolated" refers to a nucleic acid substantially free of cellular material or culture medium when produced by recombinant DNA techniques, or chemical reactants, or other chemicals when chemically synthesized. An "isolated" nucleic acid is also free of sequences which naturally flank the nucleic acid (i.e., sequences located at the 5' and 3' ends of the nucleic acid molecule) from which the nucleic acid is derived. The term "nucleic acid" is intended to include DNA and RNA and can be either double stranded or single stranded. In a preferred embodiment, the nucleic acid molecule encodes Mae1 having the amino acid sequence as shown in SEQ ID NO: 2 or FIG. 3. In another embodiment, the nucleic acid molecule is a DNA comprising the nucleotide sequence as shown in SEQ ID NO:1 and FIG. 3.

The invention includes nucleic acid sequences complementary to the nucleic acid encoding Mae1 having the amino acid sequence as shown in SEQ ID NO:2 and FIG. 3, and the nucleotide sequence as shown in SEQ ID NO:1 and FIG. 3; preferably, the nucleic acid sequences complementary to the full length nucleic acid sequence shown in SEQ ID NO: 1 and FIG. 3.

The invention also includes nucleic acid molecules having substantial sequence identity or homology to the nucleic acid sequence as shown in SEQ ID NO:1 and FIG. 3, or encoding Mae1 proteins having substantial homology to the amino acid sequence shown in SEQ ID. NO:2 and FIG. 3. Homology refers to sequence similarity between sequences and can be determined by comparing a position in each sequence which may be aligned for purposes of comparison. When a position in the compared sequence is occupied by the same nucleotide base or amino acid, then the molecules are matching or have identical positions shared by the sequences.

The invention also includes a nucleic acid molecule, and fragments of the nucleic acid molecule having at least 15 bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Isolated and purified nucleic acid molecules having sequences which differ from the nucleic acid sequence shown in SEQ ID NO:1 or FIG. 3, due to degeneracy in the genetic code are also within the scope of the invention.

An isolated nucleic acid molecule of the invention which comprises DNA can be isolated by preparing a labelled nucleic acid probe based on all or part of the nucleic acid sequences as shown in FIG. 3 or SEQ. ID. NO.: 1, and using this labelled nucleic acid probe to screen an appropriate DNA library (e.g. a cDNA or genomic DNA library). For example, a whole genomic library isolated from a microorganism can be used to isolate a DNA encoding a Mae1 protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a Mae1 protein of the invention using the polymerase chain reaction (PCR) methods and cDNA or genomic DNA. It is possible to design synthetic oligonucleotide primers from the nucleic acid molecules as shown in FIG. 3 or SEQ. ID. NO.: 1, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel Mae1 protein of the invention into an appropriate vector which allows for transcription of the cDNA to produce an RNA molecule which encodes a novel protein of the invention.

A nucleic acid molecule encoding a protein which mediates uptake of L-malate, succinic acid and malonate may also be identified using a functional approach. For example, the mae1 gene in *S.pombe* may be disrupted by employing standard recombinant DNA techniques and the DNA sequences of the mae1 gene as described herein, or alternatively, an *S.pombe* strain containing a mae1 gene may be subjected to a mutagenic treatment including radiation or chemical treatments. In particular, an *S.pombe* strain may be treated with ethylmethane sulfonate (EMS), nitrous acid (NA), or hydroxylamine (HA), which produce mutants with base-pair substitutions. Mutants defective in malate, succinic acid, or malonate utilization may be screened for example by plating an appropriate dilution onto differential agar plates where the mutant colonies are a distinguishable color. Complementation of these mutants with genomic libraries from other organisms may be used to identify clones which contain genes encoding proteins which mediate uptake of L-malate, succinic acid and malonate. (See Example 1).

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a Mae1 protein of the invention may be accomplished by expressing the cDNA in an appropriate host cell by standard techniques, and testing the activity of the protein using the methods as described herein. For example, the activity of a putative Mae1 protein may be tested by mixing with an appropriate substrate and assaying for malate permease activity. One skilled in the art can also compare the three-dimensional structure of the protein, as analyzed for example by x-ray crystallography or 2 dimensional NMR spectroscopy, with the three-dimensional structure for *S. pombe* malate permease. A cDNA having the activity, or three-dimensional structure of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of a nucleic acid molecule encoding a Mae1 protein may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may also be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably the nucleic acid sequence shown in the Sequence Listing as SEQ. ID. NO. 1 and in FIG. 3 may be inverted relative to their normal presentation for transcription to produce antisense nucleic acid molecules. The antisense sequences may be used to modulate the expression of the mae1 gene thereby reducing or inhibiting uptake of L-malate, succinic acid, or malonate.

The invention also provides nucleic acid molecules encoding fusion proteins comprising a Mae1 protein of the invention and a heterologous protein or peptide, or a selectable marker protein (see below). Construction of a nucleic acid molecule encoding a fusion protein, which comprises the nucleic acid sequence of a selected peptide or protein and a nucleic acid sequence of a Mae1 protein, employs conventional genetic engineering techniques [see, Sambrook et al, Molecular Cloning. A Laboratory Manual., Cold Spring Harbor Laboratory, Cold Spring Harbor, N.Y. (1989)]. For example, the sequence encoding a selected protein may be fused to a sequence of one of several identifiable regions which when the protein is membrane bound are found on the cell surface. In addition, the selected protein may be fused to the amino terminus of the Mae1 molecule. Alternatively, the selected protein sequence may be fused to the carboxyl terminus of the Mae1 molecule. At either the amino or carboxyl terminus, the desired peptide or protein is fused in such a manner that the fusion does not destabilize the native structure of either protein.

A nucleic acid molecule of the invention may contain multiple copies of a sequence encoding a Mae1 protein, with the sequence encoding a heterologous protein or peptide fused to only one of the Mae1 sequences, or with the heterologous protein or peptide fused to all copies of the Mae1 sequence.

A nucleic acid molecule encoding a fusion protein comprising a sequence encoding a Mae1 protein and a sequence encoding a heterologous protein or peptide sequence may optionally contain a linker peptide inserted between the Mae1 sequence and the selected heterologous peptide or protein sequence. This linker sequence may encode, if desired, a polypeptide which is selectably cleavable or digestible by conventional chemical or enzymatic methods. For example, the selected cleavage site may be an enzymatic cleavage site. The optional linker sequence may serve a purpose other than the provision of a cleavage site. The linker may also be a simple amino acid sequence of a sufficient length to prevent any steric hindrance between the Mae1 molecule and the selected heterologous peptide or protein.

A wide variety of heterologous genes or gene fragments are useful in forming the nucleic acid molecules of the present invention. Heterologous genes which may be incorporated in the nucleic acid molecules of the invention include the following:

(a) malolactic acid genes, which encode a malolactic enzyme which converts L-malate to L-lactate, and truncations, analogs and homologs thereof which have the activity of a malolactic enzyme. Examples of genes encoding a malolactic enzyme are the mleS and EML genes of *Lactobacillus lactis* (V. Ansanay, et al., FEBS 332:74–80; SEQ.ID.NOS: 3 and 5) and *L. delbrueckii* (Williams et al., 1984), and the malolatic gene described by Lautensach, and Subden (Microbios, 1984);

(b) malic acid genes which encode a malic acid enzyme which catalyzes the oxidative decarboxylation of malate to pyruvate and carbon dioxide followed by successive decarboxylation and reduction of acetaldehyde to yield ethanol, and truncations, analogs and homologs thereof which have the activity of a malic acid enzyme. Examples of malic acid genes include the mae2 gene of *S. pombe* (Viljoen et al, 1994, SEQ. ID. NO:7); and the genes encoding the malic acid enzymes of mouse (Bagchi, S., et al., J. Biol. Chem. 262, 1558–1565, 1987), rat (Mangnuson, Ma. A. et al., J. Biol. Chem. 261, 1183–1186, 1986), *Zea maize* (Rothermel, B. A. and Nelson, T. J. Biol. Chem. 264, 19587–19592, 1989), *P.vulgaris*, (Walter et al., 1988, Proc. Natl. Acad. Sci. USA 85:5546–5550)*Populus deltoides* (Van Doorsselaere et.al. 1991, Plant Physiol. 96:1385–1386); *F. linearis* (Rajeevan et al, 1991, Plant Mol. Biol. 17:371–383); *B. stearo* (Kobayshi et al., 1989, J. Biol. Chem. 264: 3200–3205), *E.coli* (Mahajan, S. K. Et al., Genetics 125,261–273, 1990), *Flaveria trinervia* (Boersch, D., and Westhoff, P., FEBS Lett.), human (Loeber, G., et al., J. Biol. Chem. 266, 3016–3021, 1991), *Ascaris suum* (Swiss-Prot database, accession number P27443) and *Mesembry-*

*anthemum crystallinum*(Cushman, 1992, Eur. J. Biochem. 208, 259–266); and (c) genes encoding enzymes involved in malate metabolism in plants, and truncations, analogs and homologs thereof which have the activity of the enzymes. Examples of enzymes involved in malate metabolism in plants include malate dehydrogenase, malic enzyme, malate synthase, fumarase, and PEP carboxylase (Martinoia, E. and D. Rentsch, Acta. Rev. Plant Physiol. Plant Mol. Biol. 1994, 45:447–67 and references set out therein).

II. Mae Proteins of the Invention

As mentioned herein, the invention contemplates an isolated Mae1 protein which mediates the uptake of L-malate, succinate, and malonate. In an embodiment, the protein is characterized in that it has part or all of the primary structural conformation (ie. continuous sequence of amino acid residues) and the enzymatic activity of Mae1 from *S. pombe*.

In particular, a purified Mae1 protein is provided which has the amino acid sequence of Mae1 from *S. pombe* as shown in SEQ.ID. No. 2 and in FIG. 3. The *S. pombe* mae1 gene encodes a protein of 435 amino acid residues with a molecular weight of approximately 49 kDa. The hydropathy profile of the deduced amino acid sequence (FIG. 4) revealed a protein with hydrophilic N- and C-termini and ten putative membrane-spanning helices, typical of membrane-transport proteins. The N-terminal 36 amino acids and the C-terminal 65 amino acids are highly hydrophilic.

Figure 5:
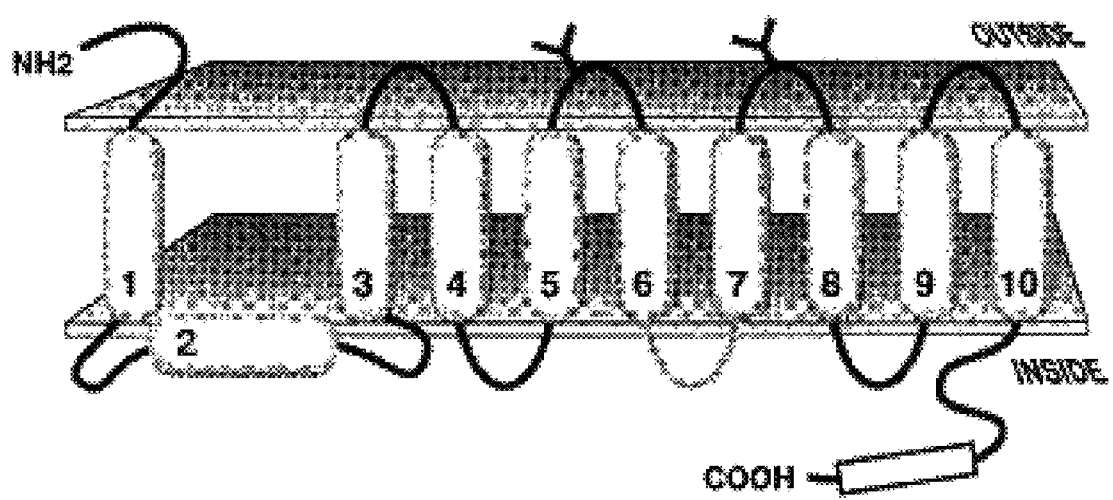
FIG. 5 is a suggested model showing the proposed distribution of the hydrophobic membrane domains which are numbered from 1 to 10.

A structural model for the malate permease was constructed by computer analysis (FIG. 5). Two prominent hydrophilic linkers, 20 and 25 amino acids long, are located between hydrophobic membrane-spanning domains two and three, and seven and eight, respectively. The length of the other hydrophilic linkers range from 7 to 12 amino acids.

Mae1 from *S. pombe* contains a number of well-characterized regions including two protein kinase C phosphorylation sites, a PEST region, a leucine zipper region, two hydrophilic linker regions, and ten membrane-spanning helices. In particular, a well conserved PEST region (amino acids 421–434) is found at the C-terminal end, consisting of proline (P), glutamic acid (E), serine (S), threonine (T) and to a lesser extent aspartic acid. A leucine zipper motif (amino acids 214 to 235), consisting of four leucine residues spaced by 6 amino acids, is located between membrane-spanning domains six and seven. Protein kinase C phosphorylation sites were found at positions 28: phvplSqrlkh and at position 94: ikypsTikdsw. Mae1 from *S.pombe* also contains three potential N-linked glycosylation sites located at amino acids 193, 277 and 336.

The three-dimensional structure of *S. pombe* malate permease depicted in FIG. 5 shows that the malate permease contains several identifiable, accessible regions, which, when the protein is membrane bound, are found on the cell surface, and are not involved in any interactions with the rest of the protein that contribute to overall structural stability. Those regions are therefore good candidates as sites for fusions or modifications (insertions, deletions etc.) as discussed herein. In addition, both the amino- and carboxyl-termini of *S. pombe* malate permease are readily accessible for fusions or modifications.

Mae1 proteins of the invention are further characterized by their ability to transport L-malate, succinate and malonate from an extracellular medium to the intracellular matrix. Malate, succinate, and malonate transport can be assayed using the transport assays described herein. For example, yeast cells transformed with a nucleic acid molecule encoding a Mae1 protein of the invention may be grown in the presence of labeled L-malate or L-succinic acid and the amount of labeled L-malate or L-succinic bound to the yeast cells may be measured.

Within the context of the present invention, a protein of the invention may include various structural forms of the primary protein which retain malate permease activity. For example, a protein of the invention may be in the form of acidic or basic salts or in neutral form. Further, individual amino acid residues may be modified by oxidation or reduction.

In addition to the full length Mae1 amino acid sequence (SEQ. ID.NO:2 or FIG. 3), the proteins of the present invention include truncations of Mae1, and analogs, and homologs of Mae1, and truncations thereof as described herein. Truncated proteins may comprise peptides of between 3 and 400 amino acid residues, ranging in size from a tripeptide to a 400 mer polypeptide. For example, a truncated protein may comprise the PEST region (amino acids 421–434) or leucine zipper motif (amino acids 214 to 235).

The proteins of the invention may also include analogs of Mae1 as shown in FIG. 3 or SEQ. ID. NO. 2, and/or truncations thereof as described herein, which may include, but are not limited to Mae1 from *S. pombe* (FIG. 3 or SEQ. ID. NO. 2), containing one or more amino acid substitutions, insertions, and/or deletions. Amino acid substitutions may be of a conserved or non-conserved nature. Conserved amino acid substitutions involve replacing one or more amino acids of the Mae1 amino acid sequence with amino acids of similar charge, size, and/or hydrophobicity characteristics. When only conserved substitutions are made the resulting analog should be functionally equivalent to the Mae 1 from *S.pombe* (FIG. 3 or SEQ. ID. NO. 2). Non-conserved substitutions involve replacing one or more amino acids of the Mae1 amino acid sequence with one or more amino acids which possess dissimilar charge, size, and/or hydrophobicity characteristics.

One or more amino acid insertions may be introduced into Mae1 from *S. pombe* (SEQ. ID. NO. 2). Amino acid insertions may consist of single amino acid residues or sequential amino acids ranging from 2 to 15 amino acids in length.

Deletions may consist of the removal of one or more amino acids, or discrete portions (e.g. one or more of the PEST region, leucine zipper motif) from the Mae1 (SEQ. ID. NO. 2) sequence. The deleted amino acids may or may not be contiguous. The lower limit length of the resulting analog with a deletion mutation is about 10 amino acids, preferably 100 amino acids.

It is anticipated that if amino acids are replaced, inserted or deleted in sequences outside the well-characterized regions such as the PEST region and the leucine zipper motif etc., that the resulting Mae1 protein could have malate permease activity. Preferably the modifications are made in the identifiable and accessible regions, which, are found on the cell surface (See FIG. 5).

The proteins of the invention also include homologs of Mae1 (SEQ. ID. NO. 2) and/or truncations thereof as described herein. Such Mae1 homologs include proteins whose amino acid sequences are comprised of the amino acid sequences of Mae1 regions from other species where the nucleotide sequence encoding the Mae1 region hybridizes under stringent hybridization conditions (see discussion of stringent hybridization conditions herein) with a probe used to obtain Mae1.

The invention also contemplates isoforms of the protein of the invention. An isoform contains the same number and kinds of amino acids as the protein of the invention, but the isoform has a different molecular structure. The isoforms contemplated by the present invention are those having the same properties as the protein of the invention as described herein.

The present invention also includes Mae1 proteins conjugated with a selectable marker protein or a heterologous protein or peptide to produce fusion proteins. Examples of selectable marker proteins are G418, β-chloramphenicol, phleomycin, and hygromycin which confer resistance to certain drugs; proteins which confer resistance to herbicides (e.g. sulphometuron-methyl) and to copper; β-galactosidase, chloramphenicol acetyltransferase, or firefly luciferase. Examples of heterologous proteins include the malolactic enzyme of L. lactis and L. delbrueckii [SEQ. ID. NOS:3 to 6], the malic enzymes of S. pombe [SEQ. ID. NOS:7 and 8], mouse, rat, human, maize, P.vulgaris, P.deltoides, F. linearis B. stearo, E.coli, Flaveria trinervia, Ascaris suum and Mesembryanthemum, and the enzymes involved in malate metabolism in plants as described herein.

III. Expression Vectors, Host Cells, and Expression of mae1

The nucleic acid molecules of the present invention having a sequence which encodes a Mae1 protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. For example, the vector may be a shuttle vector such as pRS315, or a vector such as pHVX2, YEplac181, or a CEN based plasmid.

Vectors may be selected based on the number of copies of the nucleic acid molecule to be introduced into a host cell, which in turn is determined by the choice of replication origin. Accordingly the following vectors may be selected: (a) a replicative vector (YEp) at high copy number having a replication origin in yeast (e.g. YEplac181); (b) a replicative vector (YRp) at high copy number having a chromosomal ARS sequence as a replication origin; (c) linear replicative vector (YLp) at high copy number having a telomer sequence as a replication origin; and (d) replicative vector (YCp) at low copy number having a chromosomal ARS and centromere sequences.

A nucleic acid molecule of the invention may be integrated into the genome of a host cell, preferably the genome of a yeast cell, to either replace or duplicate a native sequence. In this case an integrative vector (YIp) possessing no origin in the host cells may be selected.

The invention therefore contemplates an expression vector containing one or more nucleic acid molecules of the invention, and the necessary regulatory sequences for the transcription and translation of the inserted protein sequence (s). In particular, the expression vector may include promoter and terminator sequences for promoting and terminating transcription of the gene in the transformed host cell and expression of the malate permease gene. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)).

Selection of appropriate regulatory sequences is dependent on the host cell chosen, and may be readily accomplished by one of ordinary skill in the art. Examples of regulatory sequences which may be used in a nucleic acid molecule of the invention include the promoters and terminators of genes for alcohol dehydrogenase I (ADHI), glyceraldehyde-3-phosphate dehydrogenase (GAPDH), and 3-phosphoglycerate kinase (PGK), or other promoters that are functional in S. cerevisiae.

The necessary regulatory sequences may be supplied by the native mae1 and/or its flanking regions. However, in host cells where a native promoter is inactive (e.g. the mae1 S. pombe promoter in strains of S.cerevisiae), the promoter may be selected from suitable promoters of the host cell for example, the alcohol dehydrogenase I (ADH) and 3-phosphoglycerate kinase (PGK) promoter and the associated terminator sequences may be used with S. cerevisiae.

It will be appreciated that the level of expression of a nucleic acid molecule of the invention may be modulated by adjusting the number of copies of the nucleic acid molecule introduced into the host cell and/or the nature of the regulatory elements contained in the nucleic acid molecule.

The expression vectors of the invention may also contain a selectable arker gene which facilitates the selection of host cells transformed or transfected with a recombinant molecule of the invention. Examples of selectable marker genes are genes encoding a selectable marker protein such as G418, β-chloramphenicol, phleomycin, and hygromycin which confer resistance to certain drugs; a protein which confers resistance to herbicides (sulphometuron-methyl) and to copper; β-galactosidase, chloramphenicol acetyltransferase, or firefly luciferase. The selectable markers can be introduced on a separate vector from the nucleic acid molecule of interest.

The expression vectors may also contain genes which encode a moiety which provides increased expression of the recombinant protein; aid in the purification of the target recombinant protein by acting as a ligand in affinity purification; and target the recombinant protein to the plasma membrane. For example, a proteolytic cleavage site may be added to the target recombinant protein to allow separation of the recombinant protein from the fusion moiety subsequent to purification of the fusion protein, or a signal peptide may be used to target the malate permease to the plasma membrane of the yeast strain.

The expression vectors may be introduced into host cells to produce a transformant host cell. "Transformant host cells" include host cells which have been transformed or transfected with a recombinant expression vector of the invention. The terms "transformed with", "transfected with", "transformation" and "transfection" encompass the introduction of nucleic acid (e.g. a vector) into a cell by one of many standard techniques. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks. The most common transformation techniques that can be used for yeast strains include protoplast techniques, the technique of permeabilization to lithium salts, and electroporation. An expression vector of the invention may also be integrated into the genome of a host cell using conventional methods such as the colony hybridization procedure as described by Rose et al. (Methods in Yeast Genetics, Cold Spring Harbour Press, 1990).

To produce a fusion protein of this invention, the host cell is either transformed with, or has integrated into its genome, a nucleic acid molecule comprising a Mae1 sequence fused to the sequence of a selected heterologous peptide or protein, or selectable marker protein, desirably under the control of regulator sequences capable of directing the expression of a fusion protein. The host cell is then cultured under known conditions suitable for fusion protein production.

A wide variety of prokaryotic and eukaryotic host cells may be used as host cells for expressing a Mae1 protein or fusion protein of the invention. For example, the proteins of the invention may be expressed in bacterial cells such as E. coli, insect cells (using baculovirus), yeast cells, plant cells, or mammalian cells. Other suitable host cells can be found in Goeddel, Gene Expression Technology: Methods in Enzymology 185, Academic Press, San Diego, Calif. (1991).

Most particularly, the host cell is a yeast strain, preferably a Saccharomyces cerevisiae yeast strain, a S. bayanus yeast strain, or a Schizosaccharomyces yeast strain. Transformed host cells for use in wine-making are preferably wine yeast strains of Saccharomyces cerevisiae or Schizosaccharomyces, for example "Prise de Mousse" (Lallemande EC 1118), Vin13, Vin7, N96, and WE352.

The present invention therefore includes transformed eukaryotic or prokaryotic cells, characterized in that they contain at least one nucleic acid molecule encoding a Mae1 protein, or encoding a fusion protein of a Mae1 protein and a heterologous protein or peptide. An example of such a transformed host cell is a yeast strain having a nucleotide sequence of the mae1 gene as shown in FIG. 3 or SEQ. ID. NO. 1, and a functional polypeptide, which is a malate permease. In one embodiment, the transformed yeast strain may be Saccharomyces, transformed with a malate permease gene in particular a nucleic acid molecule encoding a Mae1 protein. In another embodiment, the transformed yeast strain may be Saccharomyces, transformed with a mae1 gene from S. pombe. In another embodiment, the transformed yeast strain may be Saccharomyces cerevisiae, and the mae1 gene may be cloned from S. pombe. Preferably the yeast strain is S. cerevisiae containing a nucleic acid molecule comprising the sequence as shown in FIG. 3 or SEQ ID NO: 1.

The present invention also includes transformed eukaryotic or prokaryotic cells, characterized in that they contain at least one nucleic acid molecule encoding a fusion protein of a Mae1 protein and a heterologous protein or peptide. In an embodiment of the invention, a yeast strain is provided which contains a nucleic acid molecule comprising a sequence encoding a Mae1 protein and a sequence encoding a malolactic enzyme, preferably comprising the mae1 S. pombe gene (FIG. 3 or SEQ ID NO: 1) and the L. lactis mleS gene (SEQ ID NO:5). In another embodiment of the invention, the yeast strain is a wine yeast strain containing a nucleic acid molecule comprising a sequence encoding a Mae1 protein, and a sequence encoding a malic enzyme, most preferably the sequence comprises S. pombe mae1 (FIG. 3 or SEQ ID NO: 1) and the S. pombe mae2 gene (SEQ. ID. NOS: 7 & 8).

In an embodiment of the invention, a method is provided for preparing a Mae1 protein comprising the steps of: constructing a vector comprising a recombinant DNA molecule having the above-defined nucleotide sequence for transforming a yeast strain and enabling synthesis of a malate transporting polypeptide. Thus, the method may include isolating the mae1 gene from S. pombe or any other organism; inserting the mae1 gene into a cloning vector, such as a yeast expression plasmid or CEN based plasmid, and introducing the mae1 gene into a S. cerevisiae yeast strain, thereby transforming S. cerevisiae into a malate transporting microorganism. The plasmid may serve as a basis for further characterization and manipulation of the mae1 gene. Expression of the mae1 gene in S. cerevisiae may be effected by replacing the S. pombe native promoter by S. cerevisiae promoter and terminator sequences. The gene construct may be subcloned, if desired, into a suitable vector before being transformed into the yeast strain, or alternatively the gene can be integrated into the chromosomal DNA of S. cerevisiae.

The methods described herein may be used to produce and isolate a Mae1 protein. Therefore, the invention provides a method for preparing a Mae1 protein comprising (a) transferring an expression vector of the invention into a host cell; (b) selecting transformed host cells from untransformed host cells; (c) culturing a selected transformed host cell under conditions which allow expression of the Mae1 protein; and (d) isolating the Mae1 protein.

Mae1 proteins of the invention may also be prepared by chemical synthesis using techniques well known in the chemistry of proteins such as solid phase synthesis (Merrifield, 1964, J. Am. Chem. Assoc.85:2149–2154) or synthesis in homogenous solution (Houbenweyl, 1987, Methods of Organic Chemistry, ed. E. Wansch, Vol. 15 I and II, Thieme, Stuttgart).

IV. Applications

Nucleotide Probes

The nucleic acid molecules of the invention allow those skilled in the art to construct nucleotide probes for use in the detection of nucleic acid sequences encoding Mae1 proteins. Suitable probes include nucleic acid molecules based on nucleic acid sequences encoding at least 6 sequential amino acids from regions of the Mae1 protein as shown in SEQ.ID NO: 1, or FIG. 3. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in yeast cells, that encode Mae1 proteins.

Antibodies

Mae1 proteins of the invention can be used to prepare antibodies specific for the proteins. Antibodies can be prepared which bind a distinct epitope in an unconserved region of the protein. An unconserved region of the protein is one which does not have substantial sequence homology to other proteins, for example the regions outside the conserved PEST and leucine zipper motifs as described herein. A region from one of the well-characterized domains (e.g.

PEST regions) can be used to prepare an antibody to a conserved region of a Mae1 protein. Antibodies having specificity for a Mae1 protein may also be raised from fusion proteins created by expressing fusion proteins in bacteria as described herein.

Conventional methods can be used to prepare the antibodies. For example, by using a peptide of a Mae1 protein, polyclonal antisera or monoclonal antibodies can be made using standard methods [e.g., the hybridoma technique originally developed by Kohler and Milstein (Nature 256, 495–497 (1975)) as well as other techniques such as screening of combinatorial antibody libraries (Huse et al., Science 246, 1275 (1989)]. The term "antibody" includes antibody fragments which also specifically react with a protein, or peptide having the activity of a Mae1 protein.

Antibodies specifically reactive with a Mae1 protein, or derivatives, such as enzyme conjugates or labeled derivatives, may be used to detect Mae1 in various samples e.g. yeasts or plants, for example they may be used in any known immunoassays which rely on the binding interaction between an antigenic determinant of a Mae1 protein and the antibodies. Examples of such assays are radioimmunoassays, enzyme immunoassays (e.g. ELISA), immunofluorescence, immunoprecipitation, latex agglutination, and hemagglutination.

Methods of Mediating Malate, Succinic Acid and Malonate Uptake

A Mae1 protein of the invention may be used to identify substances which affect the activity of the protein, and thus may be useful in mediating transport of L-malate, succinate, or malonate in a cell, preferably a microorganism (e.g. yeast) or plant cell. The invention therefore provides a method for identifying a substance that mediates transport of L-malate, succinate or malonate comprising incubating a Mae1 protein of the invention with a substrate of the Mae1 protein, and a test substance which is suspected of affecting the activity of the Mae1 protein, and determining the effect of the substance by comparing to a control. The substance may be a synthetic or natural substance.

The invention in particular provides a method for identifying a substance that mediates transport of L-malate, succinate, or malonate in a microorganism (e.g. yeast) comprising cultivating in the presence of malate, succinate or malonate and a test substance which is suspected of affecting the activity of a Mae1 protein, a microorganism which has been transformed with a nucleic acid molecule of the invention containing a sequence encoding a Mae1 protein, and expresses a Mae1 protein, assaying for uptake of malate, succinate, or malonate, and determining the effect of the substance by comparing to a control where the microorganism is cultivated without the test substance. The malate, succinate or malonate may be labelled with a detectable substance as described herein.

The substances identified using the methods of the invention as well as antisense nucleic acid molecules, and antibodies, may reduce the expression or activity of the Mae1 protein in a cell, preferably a microorganism or plant cell, thereby affecting the uptake of malate, succinic acid and malonate by the cell. Inhibitors of a Mae1 protein may be particularly useful in wine-making where the wine yeast strain used is very efficient in degrading malate. The inhibitory substances may be particularly useful in warm-regions, where there is typically insufficient acid in the wine and acid must be added to convert insipid flat wines into palatable wines.

Substances identified using the method of the invention which stimulate the activity of a Mae1 protein of the invention may be particularly useful in enhancing malolactic or maloethanolic fermentation. The stimulator substances may be useful in increasing malate uptake and they may have particular application in wine-making using yeast strains (e.g. S. cerevisiae) which do not efficiently remove malate.

Nucleic acid molecules of the invention may be used to transform a cell, preferably a microorganism or plant cell, so as to mediate uptake and metabolism of L-malate, succinic acid, or malonate by the cell. In particular, the nucleic acid molecule may render a cell, preferably a microorganism, capable of efficiently degrading malate. In an embodiment of the invention a recombinant DNA is provided which is used to transform a microorganism so as to provide it with the capability of efficiently degrading malate, the recombinant DNA comprising a nucleotide sequence which encodes a polypeptide which mediates the uptake of malate, and which enables synthesis of the polypeptide by the transformed microorganism.

More particularly, according to the invention there is provided a recombinant DNA molecule for use in transforming a yeast strain so as to provide it with the capability of efficiently degrading malate, said DNA comprising a nucleotide sequence which encodes malate permease or an intermediate therefor, or encodes at least as much of an amino acid sequence thereof as will mediate the uptake of malate, and enable expression of malate permease in the transformed yeast.

Host cells (e.g. microorganisms and plant cells) of the invention containing a nucleic acid molecule of the invention may be used to mediate uptake and metabolism of L-malate, succinic acid, or malonate. Therefore, the invention provides a method of mediating uptake and metabolism of L-malate, succinic acid, or malonate comprising growing in the presence of a supply of L-malate, succinic acid, or malonate, a cell transformed with a nucleic acid molecule of the invention. In an embodiment of the invention, a method of degrading malate is contemplated which includes cultivating, in the presence of a supply of malate, a microorganism which has been transformed with a nucleotide sequence which encodes a polypeptide that mediates the uptake of malate. Preferably, the microorganism is transformed with a nucleic acid molecule comprising a sequence encoding a Mae1 protein, most preferably the sequence comprises S. pombe mae1 (FIG. 3 or SEQ ID NO:1).

More specifically, according to the invention there is provided a method of degrading malate which includes cultivating in the presence of a supply of malate, a yeast strain which has been transformed by introducing into the yeast strain, a nucleotide sequence which encodes malate permease or an intermediate therefor, or encodes at least as much of an amino acid sequence thereof as will mediate the uptake of malate, and which includes a promoter and a terminator for promoting and terminating transcription, and expression of the malate permease gene. Preferably the yeast strain is S. cerevisiae containing a nucleic acid molecule comprising a sequence encoding a Mae1 protein, most preferably the sequence comprises S. pombe mae1 (FIG. 3 or SEQ ID NO:1).

The method of the invention for degrading malate using transformed host cells of the invention is particularly useful in wine-making, and it provides a simple, less expensive means to degrade malate efficiently either during, or after the alcoholic fermentation step. Therefore, the invention also contemplates a method of degrading malate during fermentation of wine, which method includes, cultivating, in grape musts which contain a supply of malate, a yeast strain transformed by a nucleic acid molecule of the invention. In an embodiment of the invention the yeast strain is transformed by recombinant DNA material which includes a nucleotide sequence which encodes a functional malate permease or intermediate therefor, or encodes at least as much of an amino acid sequence thereof as will provide malate permease activity, and which further encodes a promoter for promoting transcription of the nucleotide sequence and driving expression of the nucleotide sequence, and a terminator to end transcription of the nucleotide sequence resulting in a permease to transport malate into the yeast cells.

According to the invention there is also provided a method of fermenting wine, which includes cultivating, in a wine fermentation medium which includes grape must containing a supply of malate, a yeast strain transformed by a nucleic acid molecule of the invention. In an embodiment of the invention the yeast strain is transformed with a recombinant DNA material which includes a nucleotide sequence which encodes a functional malate permease or intermediate therefor, or encodes at least as much of an amino acid sequence thereof as will provide malate permease activity, and which further encodes a promoter for promoting transcription of the nucleotide sequence and driving expression of the nucleotide sequence, and a terminator to end transcription of the nucleotide sequence, resulting in a permease to transport malate into the yeast cells.

The yeast strain used in the methods of the invention for the fermentation of wine may be a wine yeast strain containing a nucleic acid molecule comprising a sequence encoding a Mae1 protein, most preferably the sequence comprises *S. pombe* mae1 (FIG. 3.or SEQ ID NO: 1). In a preferred embodiment of the invention, the yeast strain contains a nucleic acid molecule comprising a sequence encoding a Mae1 protein and a sequence encoding a malolactic enzyme, preferably comprising the mae1 *S. pombe* gene (FIG. 3 or SEQ ID NO: 1) and the *L. lactis* mleS gene (SEQ ID NO: 5). In another preferred embodiment of the invention, the yeast strain is a wine yeast strain containing a nucleic acid molecule comprising a sequence encoding a Mae1 protein, and a sequence encoding a malic enzyme, most preferably the sequence comprises *S. pombe* mae1 (FIG. 3 or SEQ ID NO: 1) and the *S. pombe* mae2 gene [SEQ. ID. NO: 7]. The present inventors have shown that recombinant *S. cerevisiae* strains containing the *S. pombe* mae 1 and mae2 genes under control of *S. cerevisiae* promoter and terminator signals degrade 8–9 g/l of malate.

Examples of wine yeast strains which can be used in the methods of the invention are wine strains of *S. cerevisiae* and *S. bayanus* including the industrial wine yeast strains Bourgovin RC 212, ICV 0-47, 71B-1122, KIV-1116 (Lallemande) "Prise de Mousse"(Lallemande EC 1118), Vin 7, Vin 13, N96, and WE352 (Dept. of Microbiology, University of Stellenbosch).

The yeast strains of the present invention containing a nucleic acid molecule encoding a malolactic enzyme (e.g. mles) will be useful in degrading malate to L-lactate and $CO_2$ during alcohol fermentation (i.e. malolactic fermentation), whereas the yeast strains containing a nucleotide sequence encoding a malic enzyme (e.g., mae2) will be useful in degrading malate to ethanol and $CO_2$ after alcoholic fermentation (maloethanolic fermentation). The yeast strains containing a nucleic acid molecule encoding a malolactic enzyme may also be ethanol sensitive strains. These ethanol sensitive strains can be used as co-cultures together with industrial wine yeast strains.

The yeast strains of the invention which are particularly useful in the fermentation of wine may be selected based on their fermentation efficacy using an automated version of a mini-fermentometer as described by Reed and Chen (Am J Enol Vitic 29:165, 1978). Strains selected based on the fermentation efficacy tests may be scaled up for lot productions and evaluated for parameters such as conversion efficacy, cold tolerance, short lag phase, ethanol tolerance, $SO_2$ tolerance, low foaming activity, malate degradation, flocculence at the end of fermentation, and resistance to killer zymotoxins. Organoleptic trials may also be conducted using conventional procedures. A vinter can select strains for maloethanolic fermentation or malolactic fermentation based on the composition of the must and the style of the wine.

It will be appreciated that the nucleic acid molecules, host cells, and methods of the invention may be used to mediate malate, succinic acid, or malonate uptake in technological fields other than wine-making. For example, increasing malate uptake and metabolism of malate using the nucleic acid molecules of the invention to thereby increase ethanol production, may be useful in wine and fruit juice fermentations for the production of alcoholic liquors such as brandy.

In plants, malate plays a pivotal function in most organelles. Malate serves the following important functions in plants: (i) malate is as an intermediate in the tricarboxylic acid cycle, and malate accumulation may serve as respiratory energy during the night; (ii) malate is the store for both $CO_2$ and reduction equivalents in CAM; (iii) an oxaloacetate-malate shuttle mediates transport of reduction equivalents to the cytosol or peroxisomes, and may function in the generation of apoplastic NADH which is used in a complex reaction to generate apoplastic $H_2O_2$; (iv) malate can be used as an osmotieum; (v) malic acid synthesis and degradation are components of the pH state mechanism; (vi) malate synthesis balances unequal cation or anion uptake by roots; (vii) malate is an important component of exudate of some plant roots which increases phosphate availability in the soil; and (viii) malate modulates the voltage-dependence of stomatal anion channel and it may be part of the $CO_2$ sensor mechanism (E. Martinoia and D. Rentsch, Acta. Rev. Plant Physiol Plant Mol Biol 1994, 45:447–67).

The nucleic acid molecules (e.g. nucleic acid molecules encoding Mae1 proteins, or functional equivalents of Mae1 proteins, and optionally genes encoding enzymes involved in malate metabolism in plants as described herein), host cells containing the nucleic acid molecules, and substances of the present invention may be useful in modulating malate metabolism in plants thereby affecting one or more functions as described above. In particular, the nucleic acid molecules, host cells, and substances of the present invention may be useful in modifying malate transport in plant organelles such as chloroplasts, mitochondria, vacuoles, peroxisomes, and symbiosomes to thereby affect malate metabolism in the organelles. The nucleic acid molecules, host cells, and substances of the present invention may be useful in modulating the efficiency by which some plants convert $CO_2$ to carbohydrates. Further, malic acid plays a very important role as an energy reservoir in the diurnal cycle of higher plant metabolism. Therefore, nucleic acid molecules of the invention may be used in plastid, chloroplast, mitochondrial, and other higher plant organelles to control malate metabolism leading to the construction of more energy efficient plants of agricultural or other commercial interest.

The invention will be more fully understood by reference to the following examples. However, the examples are merely intended to illustrate embodiments of the invention and are not to be construed to limit the scope of the invention.

EXAMPLES

Example 1

Cloning and Characterization of MAE1

Strains and growth conditions: *Escherichia coli* strain HB101 (hsd20 leuB supE44 ara-14 galK2 lacY1 proA2 rpsL20 xyl-5 mtl-1 recA13 mcrB) was used. Procedures for manipulating *Escherichia coli* cells and DNA were based on Sambrook et al. (1989). Furthermore, a haploid strain of *Schizosaccharomyces pombe* 972 leu 1-32 h-(wild-type), and a haploid mae1⁻mutant *S. pombe* leu 1-32 T⁻h mae1⁻ (Osothsilp and Subden, 1986b) were also used in this study. The yeast cells were grown in YE (2% glucose, 0.5% yeast extract), MM (Alfa et al., 1993) plus leucine and YEPD medium (1% yeast extract, 2% Bactopeptone, 2% glucose), supplemented with 0.8% L-malic acid (Sigma, St. Louis, Mo.) if required. Transformants were selected on YNB (0.17% yeast nitrogen base without amino acids and $(NH_4)SO_4$, [Difco Laboratories, Detroit, Mich.], 0.5% $(NH_4)_2SO_4$ 2% glucose, 1.7% bacto-agar [Difco Laboratories, Detroit, Mich.] and malate-glucose indicator agar (MGIA), previously described by Osothsilp and Subden (1986b).

Yeast transformation: *S. pombe* cells were transformed by electroporation (Prentice, 1992). Pulsed-field gel electrophoresis and Southern blotting: Chromosomal blotting was done as described by Viljoen et al. (1994). Standard procedures (Sambrook et al., 1989) were used for Southern blotting. A 0.45-μm Hybond-N nylon membrane (Amersham International, Buckinghamshire, UK) was used. The random-primed DNA-labelling kit (Boehringer Mannheim, Mannheim, Germany) was used for radio-labelling the mae1 probe.

Northern blotting: RNA isolation was done according to Viljoen et al. (1994). Total RNA was separated in a 0.8% agarose/2.2 M-formaldehyde denaturing gel and transferred to a 0.45 μm Hybond-N nylon membrane (Amersham International, Buckinghamshire, UK) as described by Sambrook et al. (1989).

Cloning of mae1 gene: A Hind III genomic library of *S. pombe* prepared in a shuttle vector WH5 by Paul Young (Queen's University, Kingston, Ontario) was used to transform *S. pombe* strain leu1-32 mae1⁻, h⁻ according to the method of Beach et al. (1982). Transformants were transferred into 100 μl of MG1 liquid indicator medium (Osothsilp and Subden, 1986b). Complementation was determined calorimetrically and then confirmed by transport activity assays (Osothsilp and Subden, 1986b).

A 5.4-kb EcoR1 subclone and a 3.4-kb Smal subclone in pRS315 (Sikorski and Hieter, 1989) were transformed into the mae1 mutant to determine which fragment contained the mae1 gene.

DNA Sequence Analysis of mae1

In order to sequence the cloned fragment, unidirectional digestions with Exonuclease III were performed (Sambrook et al., 1989). The deletion derivatives were transformed into *E. coli* (Tschumper and Carbon, 1980).

Plasmid DNA was isolated from the transformants using the alkaline lysis method of Lee and Rasheed (1990) and digested with PvuII to determine the sizes of the fragments obtained. Overlapping fragments were selected for DNA sequence analysis (Tabor and Richardson, 1987) and the DNA fragment containing the mae1 gene was sequenced in both directions using Sequenase v2.0 (US Biochemical Corp., Cleveland, Ohio). The nucleotide sequence was analyzed with the Genetics Computer Group package of programs. Searches of the Genbank database were performed using the FASTA and TFASTA programs and using BLAST on the NCB1 file service (Altschul et al., 1990). Transmembrane segments of the mae1 protein were predicted by the methods of Eisenberg et al. (1984) and Rao and Argos (1986).

Transport assays for L-malic and succinic acids: Yeast cells in the logarithmic growth phase (OD of 1.2 at $A_{595}$) were harvested and washed three times with 0.1 M KCl (pH 3.5). The cells were resuspended in 4 ml 0.1 M KCl (pH 3.5) and stored at 4° C. Transport assays were completed within 3 h. The cell suspensions were pre-incubated for 5 min in a shaker water bath at 30° C. at 100 rpm. Assays were initiated by adding 25 μl of $^{14}$C-labelled L malate (45 μCi/μmol) (Amersham), 100 μl of succinic acid (42 μCi/μmol) (ICN), 100 μl malonic acid (56.7 μCi/μmol) (Du Pont) or 100 μl β-ketoglutarate (51.8 μCi/μmol) (Du Pont). A 0.5-ml sample was withdrawn at 10, 20, 40, 60, and 120 sec intervals, rapidly filtered through 0.45 μm membranes (Millipore Corporation, Bedford, Mass.), and immediately washed three times with 5 ml amounts of ice-cold 0.1 M KCl (pH 3.5). Filters containing the cells were oven-dried at 50° C. and placed in scintillation vials containing 5 ml of scintillation reaction mixture (Boehringer Mannheim, Mannheim, Germany). Pre-boiled (5 min) cells were used to determine non-specific binding of [$^{14}$C] malate, succinate, malonate and a-ketoglutarate to the yeast cells.

Cloning and subcloning the mae1 gene: The mae1 gene was cloned from a *S. pombe* HindIII genomic library by complementation of a transport mutant. Osothsilp and Subden (1986b) generated various mutants of *S. pombe* that were unable to utilize malate. A 3.4-kb Sma1 subclone was the smallest fragment able fully to restore L-malate transport in the mutant.

Chromosomal localization of the mae1 gene: Southern analysis of CHEF gels (FIG. 1) confirmed the location of the mae1 gene on chromosome 1 (Osothsilp, 1987). Sequence analysis revealed that the mae1 gene is located 2842 bp 5' to the MFm1 gene (Davey, 1992) (FIG. 2).

Nucleotide sequence of the mae1 gene: The sequence of the *S. pombe* mae1 gene has been submitted to GenBank under accession number U21002 but is not available to the public or to any person other than the applicant without the applicant's authorization. A restriction map of the mae1 gene is shown in FIG. 2. The nucleotide sequence of the mae1 gene of the invention is given in FIG. 3. DNA sequence analysis revealed an open reading frame of 1314 bp. Homology searches of the GenBank database v72.0 conducted for the nucleotide sequence and the deduced protein sequence, did not reveal any significant similarity to other DNA sequences or proteins. A prominent TATAT repeated (four times) sequence was located at −153 to −175 bp upstream of the ATG codon. A direct repeat of 10 bp TCATTTTTA separated by 9 bp was found at positions −258 to −267 and −277 to −286.

Features of the mae1 protein: The mae1 gene is predicted to encode a protein of 435 amino acid (aa) residues with a predicted molecular weight of approximately 49 kDa. The hydropathy profile of the deduced aa sequence (FIG. 4) revealed a protein with hydrophilic N and C-termini and ten putative membrane-spanning helices, typical of membrane-transport proteins. The N-terminal 36 aa and the C-terminal 65 aa are highly hydrophilic. No signal peptide was found at the N-terminus but the presence of an internal signal peptide should not be ruled out. Several membrane proteins without an N-terminus signal sequence, e.g. the arginine permease encoded by CAN 1 (Hoffmann, 1985) and the GAL2 protein (Tschopp et al., 1986) from *S. cerevisiae* do not contain a signal sequence.

Transmembrane segments of the mae1 protein were predicted by the methods of Eisenberg et al. (1984) and Rao and Argos (1986).

A structural model for the malate permease was constructed by computer analysis (FIG. 5). Two prominent hydrophilic linkers, 20 and 25 aa long, are located between hydrophobic membrane-spanning domains two and three, and seven and eight, respectively. The length of the other hydrophilic linkers range from 7 to 12 aa.

Several conserved motifs were recognized in the mae1 protein. A well conserved PEST region (aa 421–434) is found at the C-terminal end. Many proteins with intracellular half-lives of less than 2 h contain one or more PEST regions, consisting of proline (P), glutamic acid (E), serine (S), threonine (T) and to a lesser extent aspartic acid (Rogers et al., 1986).

A leucine zipper motif (aa 214 to 235), consisting of four leucine residues spaced by 6 aa, is located between membrane-spanning domains six and seven. The periodicity of a leucine or isoleucine every seventh residue (Landschulz et al., 1988) has been observed in several transport proteins (Bisson et al., 1993). In mammalian glucose transporters and many of the fungal transporters a conserved zipper motif is found in or near the second putative transmembrane domain (White and Weber, 1989). These motifs have been shown to mediate protein—protein interactions in several systems by means of a coiled-coil structure. It is not known if this motif has any function in transporters. There is, however, a high degree of conservation of this motif among eukaryotic transporters in general (Bisson et al., 1993).

The mae1 protein contains three potential N-linked glycosylation sites located at aa 193, 277 and 336. The possible protein kinase C phosphorylation sites were found at positions 28: phvplSqrlkh and at position 94: ikypsTikdsw.

Expression of the mae1 gene: Northern analysis revealed that the mae1 gene encodes a single transcript of approximately 1.5 kb. Expression of the mae1 gene in the presence of glucose, raffinose or fructose (FIG. 6) revealed that the S. pombe mae1 gene was not subject to catabolite repression as was previously reported for the malate permease genes of C. utilis (Cassio and Leâo, 1993) and H. anomala (Côrte-Real and Leâo, 1990).

Malic and succinic acid transport by the S. pombe mae1 permease: Malic, succinic, malonic and α-ketoglutaric acid transport assays were done using a wild-type strain of S. pombe, a mae1⁻ mutant and the mae1⁻ mutant complemented with the mae1 gene. The 3.4-kb Sma1 fragment containing the mae1 gene cloned into pRS315 fully restored transport of L-malic (FIG. 7(a)), succinic (FIG. 7(b)) and malonic acids in the mae1⁻ mutant. α-Ketoglutarate was not transported by any of the S. pombe strains used in the transport assays.

Sousa et al. (1992) stated that competitive inhibition of initial uptake rates of L-malic acid by succinic acid, D-malic acid, fumaric acid, oxaloacetic acid, α-ketoglutaric acid, maleic acid and malonic acid suggests that these acids are transported by the same carrier. The results show that the mae1 gene of S. pombe encodes a general permease for L-malate, succinate and malonate.

This data shows a permease of $C_4$ dicarboxylic acids in eukaryotes.

Example 2
Functional Expression of S. pombe mae1 and mae2 Genes in S. cerevisiae.

S. cerevisiae cannot degrade malate efficiently due to the absence of a malate transporter, and a malic enzyme with low substrate affinity. In contrast, S. pombe degrades malate actively as the yeast contains a permease for malate and a malic enzyme with high substrate affinity (FIG. 8). lacZ fusions demonstrated that the promoters of the mae1 (SEQ ID NO: 1) and mae2 (SEQ ID NO: 3) genes of S. pombe are not functional in S. cerevisiae. To express these genes in S. cerevisiae, mae1 and mae2 open reading frames (ORFs) of S. pombe were subcloned into expression cassettes containing the S. cerevisiae alcohol dehydrogenase (ADH1) and 3-phosphoglycerate kinase (PGK1) promoter and terminator sequences. The different constructs employed in this study are listed in Table 1.

All plasmids listed in Table 1 were transformed into laboratory strain S. cerevisiae YPH259 (Sikorski, 1989) The recombinant S. cerevisiae strains containing the mae1 gene were able to actively transport L-malate (FIG. 9), thus demonstrating synthesis, correct post-translational modification and insertion of the S. pombe Mae1 protein into the plasma membrane of S. cerevisiae. The ability of the recombinant S. cerevisiae strains, containing the S. pombe mae1 and mae2 genes under control of S. cerevisiae promoter and terminator signals, to degrade 8–9 g/l of L-malate in 2% glycerol-ethanol-based (respiratory conditions) and 2% glucose-based (fermentative conditions) media, were investigated (FIGS. 10 and 11).

The control yeast strains YADH and YPGK degraded only insignificant amounts of L-malate after 22 days. Recombinant yeasts YADH-mae1 and YPGK-mae1 containing only the permease, showed an increased ability to degrade L-malate (FIGS. 10 and 11) which was probably accomplished by the native malic enzyme of S. cerevisiae. Degradation of L-malate by recombinant strains containing only the S. pombe malic enzyme, was not significantly different from that of the control yeasts. However, when both the malate permease (mae1) and the S. pombe mae2 genes were introduced, complete degradation of L-malate occurred.

Figure 10:
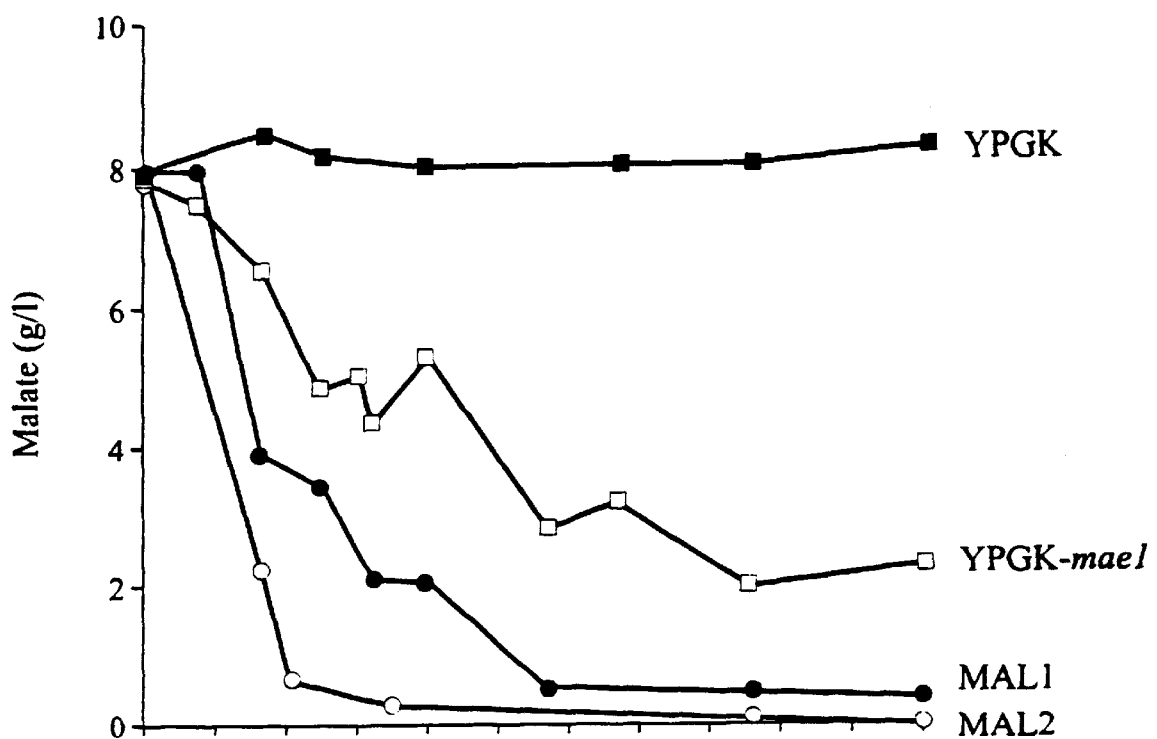
FIG. 10 shows malate degradation by the recombinant strains of *S. cerevisiae* containing the mae1 and/or mae2 genes of *S. pombe* in 2% glycerol-ethanol medium containing 8–9 g/l L-malate.
Figure 11:
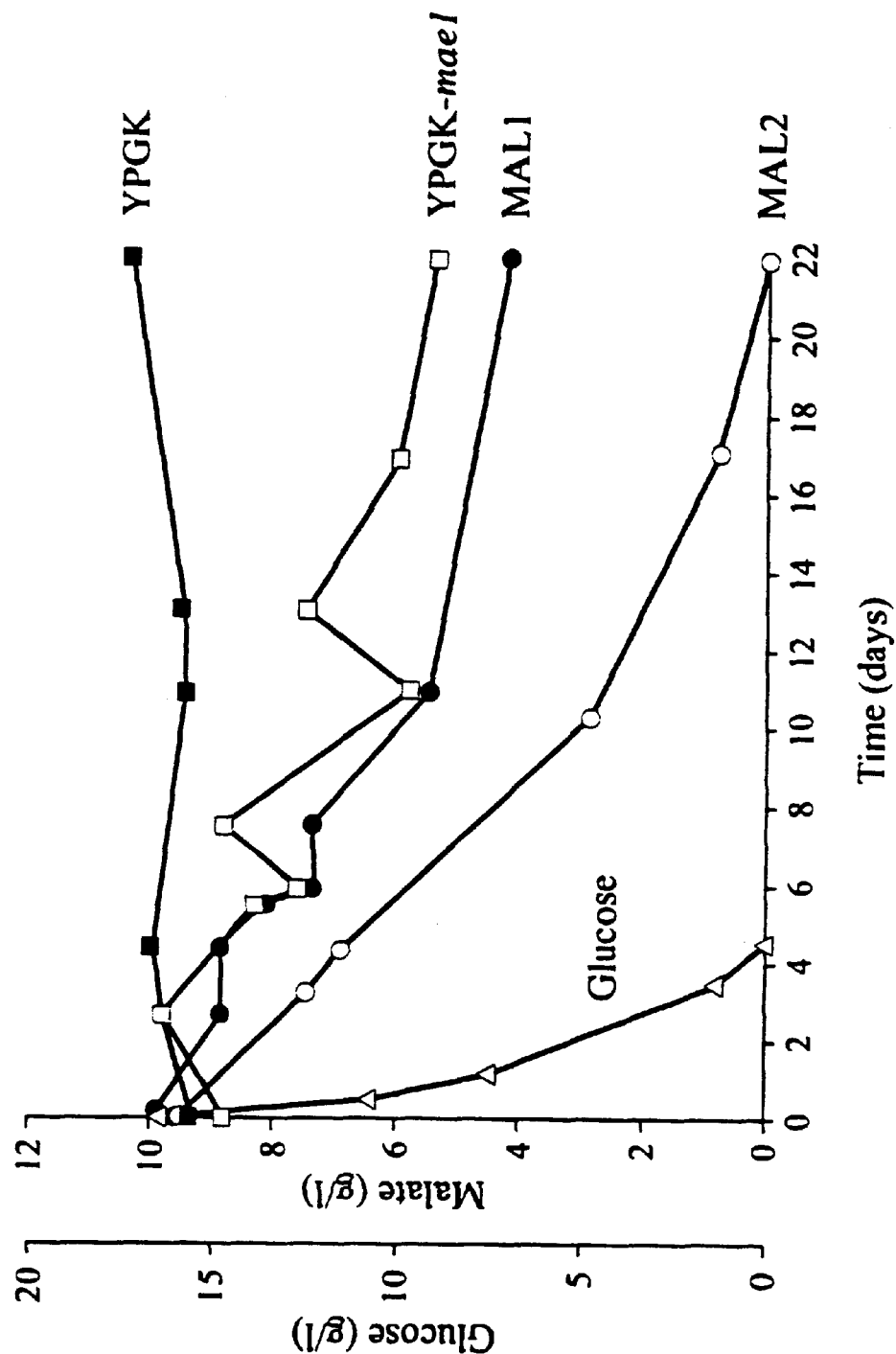
FIG. 11 shows malate degradation by the recombinant strains of *S. cerevisiae* containing the mae1 and/or mae2 genes of *S. pombe* in 2% glucose medium containing 8–9 g/l L-malate.

In a 2% glycerol-ethanol and a 2% glucose medium the recombinant strain MAL2 was able to degrade L-malate fully within 7 and 19 days, respectively (FIGS. 10 and 11). Compared to MAL2, the MAL1 recombinant strain degraded malate less efficiently in both glycerol-ethanol and glucose media. This phenomenon could possibly be explained by the fact that the mae2 gene, under control of the ADH1 promoter (MAL2), is more strongly expressed than the mae2 gene under control of the PGK1 promoter (MAL1). It is also possible that over-expression of the Mae1 protein may have a disrupting effect on the yeast cell membrane. This effect would have been more severe in the construct where the mae1 gene is under control of the stronger ADH1 promoter.

The ability of strains MAL1 and MAL2 to metabolize L-malate differed considerably in glycerol-ethanol and glucose media. Both recombinant strains performed much more efficiently in glycerol-ethanol than in glucose medium. In glycerol-ethanol 92% (7 g/l) L-malate was rapidly degraded in 4 days by the MAL2 strain (FIG. 10), whereas in glucose medium (FIG. 11) this strain degraded L-malate much slower; after 4 days only 27% of the malate was degraded. Complete degradation of L-malate in glucose medium occurred only after 18–19 days. Neither the PGK1 promoter nor the ADH1 promoter used is subject to glucose regulation; expression of the mae1 and mae2 genes in the glucose medium was confirmed by Northern and Western blot analyses.

This study has shown that S.cerevisiae require a permease to degrade malate efficiently. In contrast to numerous unsuccessful attempts elsewhere, a strain of S.cerevisiae was engineered that degrades up to 8 g/l L-malate within 7 days under aerobic conditions.

Example 3
Malolactic Fermentation in Grape Musts by a Genetically Engineered Strain of S. cerevisiae.

The following materials and methods were used in the study outlined in this example:

Strains and plasmids: The different strains and plasmids employed are listed in Table 2.

Figure 15:
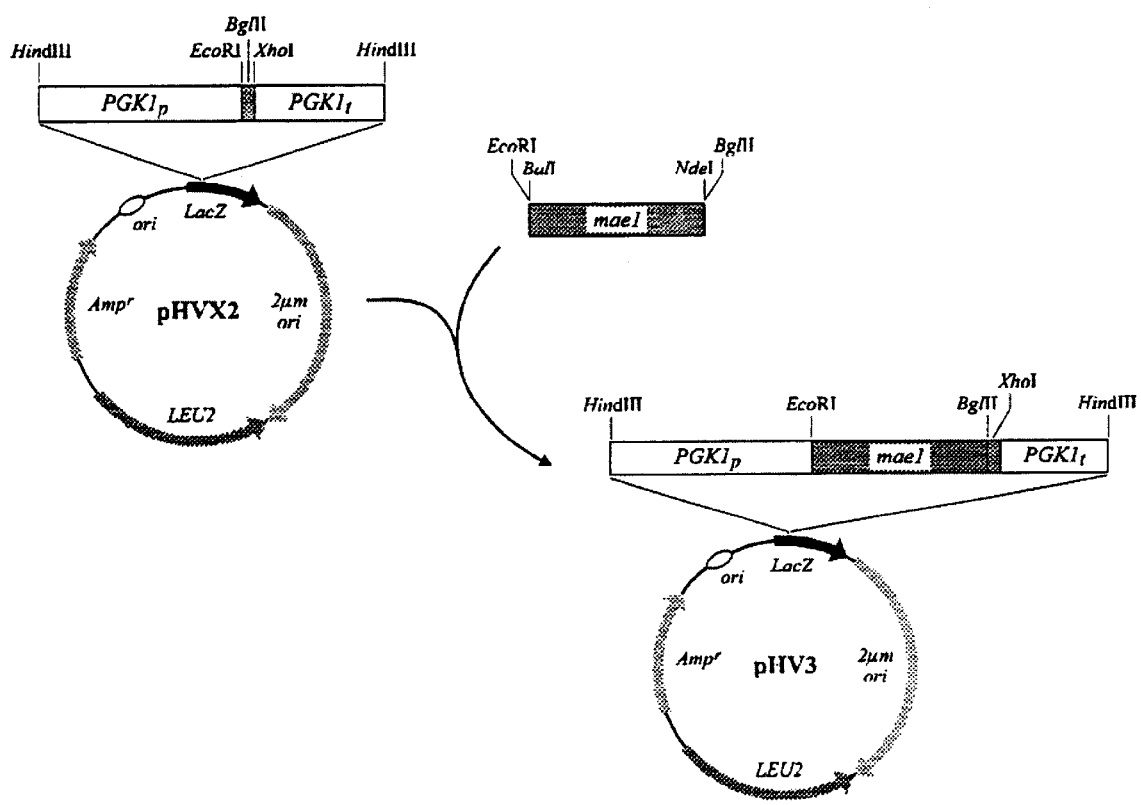
FIG. 15 shows a schematic representation of the subcloning of the *S. pombe's* mae1 ORF under control of the PGK1 promoter and terminator sequences in pHVX2, a derivative of Yeplac181.

Subcloning of the mae1 and mleS genes: DNA manipulations were performed in the yeast-E. coli shuttle vector YEplac181 (Gietz and Sugino, 1988). The expression vector pHVX2 (Table 2) was obtained by subcloning a HindIII fragment from plasmid pJC (Crous et al., 1995), containing the PGK1 promoter and terminator sequences into the HindIII site of Yeplac181 (FIG. 15). The mae1 ORF was isolated as a BalI-NdeI fragment from plasmid pJG1 (Grobler et al., 1996) and subcloned into YEplac181 containing a multiple cloning site with EcoRI, BalI, NdeI and BglII restriction sites. The mae1 ORF was reisolated as an EcoRI-BglII fragment and subcloned into the EcoRII BglII site of pHvX2 to yield plasmid pHV3 (FIG. 15). The cloning and expression of the L. lactis mleS gene in S. cerevisiae have previously been described (Denayrolles et al., 1994).

Culture conditions: E. coli JM109 (Table 2) was grown in terrific broth (1.2% tryptone, 2.4% yeast extract, 0.4% glycerol and 10% (v/v) 0.17 M $KH_2PO_4$ and 0.72 M $K_2HPO_4$ buffer solution) at 37° C. E. coli transformants were selected on LB medium (0.5% yeast extract, 1% NaCl, 1% tryptone) supplemented with ampicillin.

Yeast cells were cultured in liquid YPD media (1% yeast extract, 2% bactopeptone, 2% glucose) at 30° C. S. cerevisiae was transformed with plasmids pHV3 and pMDMALO together, as well as with pHVX2, pHV3 or pMDMALO on their own (Table 2). Transformants were isolated on selective YNB agar plates (0.17% yeast nitrogen base (YNB) without amino acids (aa) and ammonium sulphate [Difco Laboratories, Detroit, Mich.], 0.5% $(NH_4)_2SO_4$, 2% glucose and 1.7% agar, supplemented with 0.002% (w/v) adenine, histidine and 0.003% (w/v) lycine with or without uracil and leucin, or both. The transformants were cultured to high cell density in 10 malo-lactic YNB liquid medium at 30° C., harvested by centrifugation and resuspended in sterile grape juice before inoculation into grape must.

Malolactic fermentation in grape musts: Recombinant strains of S. cerevisiae containing the different plasmids were inoculated to a final concentration of $2 \times 10^6$ cells/ml in 200 ml must (preheated to 15–20° C.) in 250 ml glass containers. Cabernet Sauvignon (2.8 g/l L-malate) and Shiraz (3.2 g/l L-malate) musts were fermented at 20° C. and Chardonnay must (3.4 g/l L-malate) at 15° C., without shaking. Both red and white grape musts were supplemented with 0.075% diammonium phosphate before inoculation.

The malate concentration during fermentation was measured enzymatically using the L-Malic Acid Test Kit (Boehringer Mannheim, Germany). Malate to lactate conversion was visualized by paper chromatography according to standard methods. Plate counts on YPD agar plates were used to determine viable cell numbers and growth of the malolactic strains of S. cerevisiae.

Figure 12:
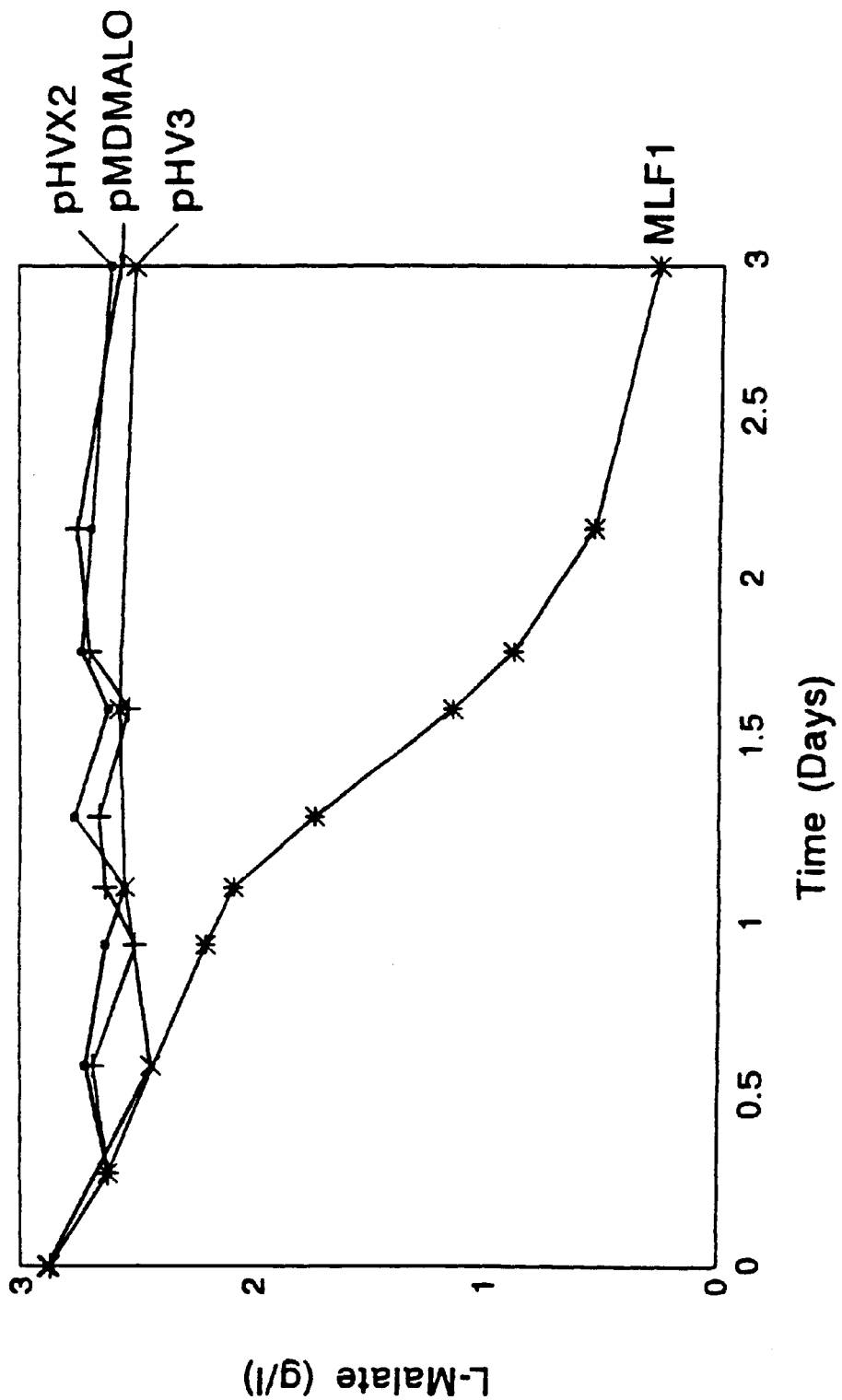
FIG. 12 shows the degradation of L-malate in Cabernet Sauvignon grape must by recombinant strains of *S. cerevisiae*, including control strains.
Figure 13:
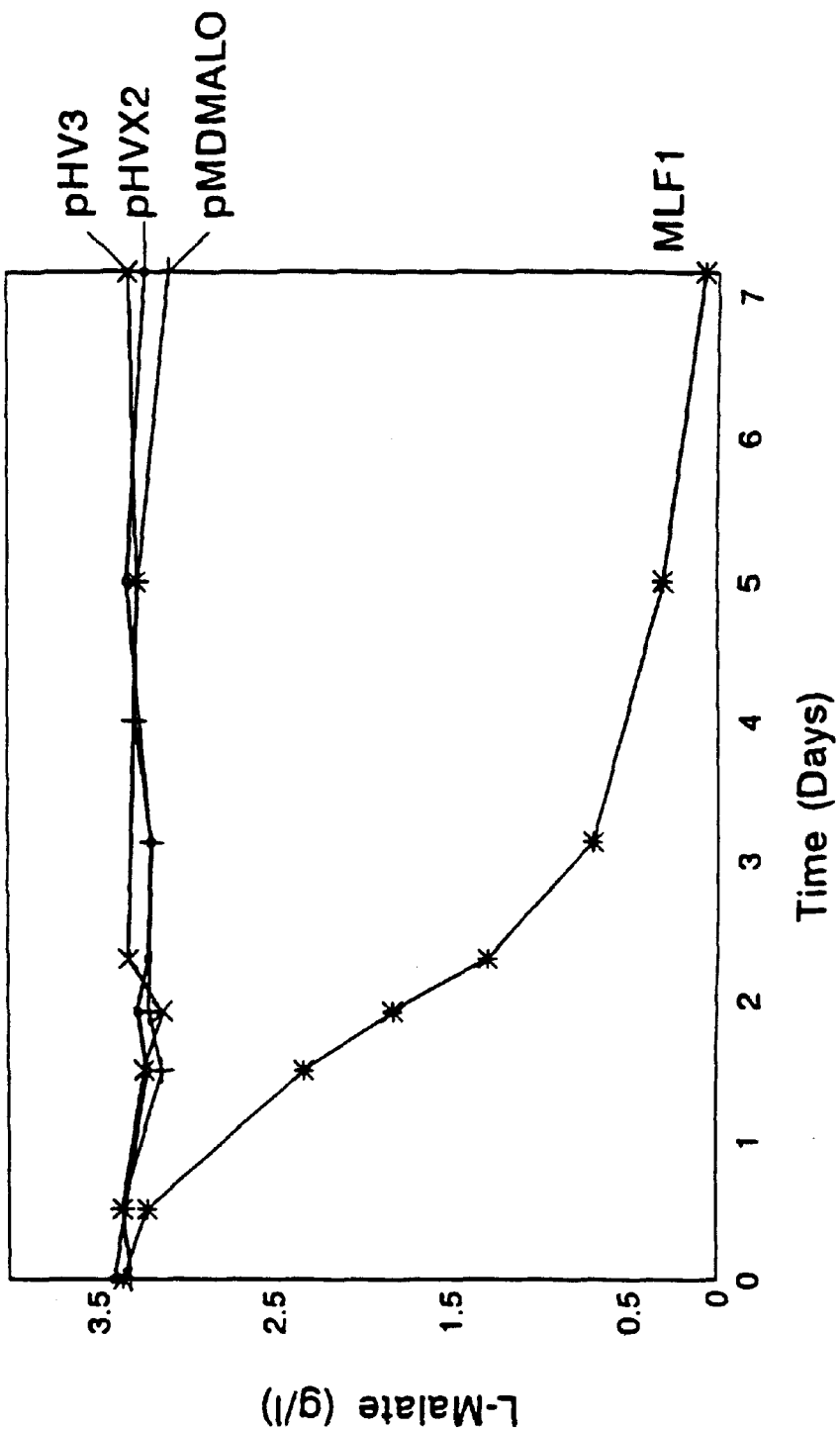
FIG. 13 shows the degradation of L-malate in Chardonnay grape must by recombinant strains of *S. cerevisiae*, including control strains.

In this study a recombinant strain of S. cerevisiae, containing both the S. pombe mae1 (SEQ ID NO: 1) and L. lactis mleS (SEQ ID NO: 2) genes, was constructed. The ability of the recombinant strain to conduct malolactic fermentation in Cabernet Sauvignon, Shiraz and Chardonnay grape musts was investigated. The recombinant yeast strain (MLF1), containing both the S. pombe mae1 and L. lactic mleS genes, efficiently and rapidly degraded L-malate to L-lactate in grape must in a significantly short period of time (FIGS. 12 and 13). The control yeast strains, containing only the PGK1-expression cassette (pHVX2), or the mleS gene (pMDMALO) or the mae1 (pHV3) gene under the control of the PGK1 promoter, were unable to degrade L-malate to L-lactate and $CO_2$.

Figure 14:
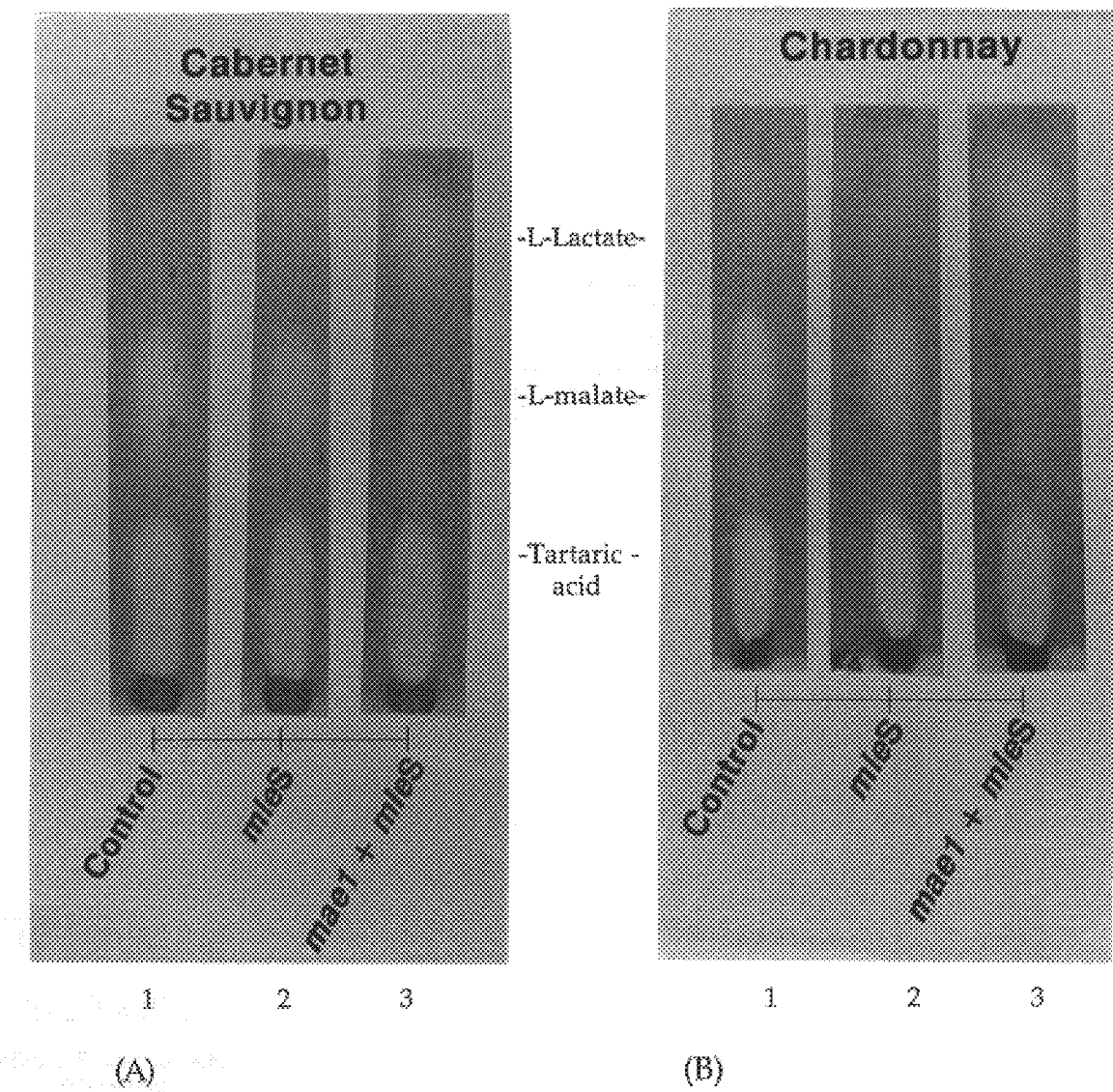
FIG. 14 are blots showing malolactic fermentation by the recombinant yeast strains of *S. cerevisiae* in Cabernet Sauvignon (A) and Chardonnay (B) wines after fermentation.

Rapid and complete metabolism of 2.8 g/l L-malate in Cabernet Sauvignon must was obtained within 3 days (FIG. 12). In Chardonnay must, 3.4 g/l L-malate was degraded to lactate within 7 days at 15° C. (FIGS. 13 and 14). Rapid malolactic fermentation (2 days) with the recombinant strain was also achieved in Shiraz grape must.

Integrating the mae1 and mleS genes into the genomes of wine yeast strains should produce strains which are able to degrade malate to lactate and $CO_2$ during the alcoholic fermentation. An alternative approach is to construct ethanol sensitive malolactic strains of S. cerevisiae which can be used as co-cultures together with industrial wine yeast strains. The use of ethanol sensitive malolactic strains of S. cerevisiae during vinification should result in a rapid and complete degradation of malate to lactate. However, the spread of malolactic yeasts in a cellar will be prevented as these yeast cells will be killed during the latter stages of fermentation due to ethanol toxicity. The early completion of malolactic fermentation in wine is of great importance to winemakers, since cellar operations can commence immediately to prevent oxidation and spoilage of wine. The application of malolactic strains of S. cerevisiae can circumvent delays with the early bottling and storage of wine, immediately after alcoholic fermentation.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

Below full citations are set out for some of the references referred to in the specification, and detailed legends for some of the figures are provided.

The application contains sequence listings which form part of the application.

TABLE 1

Constructs used to engineer a malate degrading pathway in S. cerevisiae YPH259 (19)

| Name of construct | Description | Recombinant strains |
|---|---|---|
| pHVX1 | Shuttle vector YEplac181 (18), containing the $ADH1_p$-$ADH1_t$ expression cassette | YADH |
| pHVX2 | Shuttle vector YEplac181 containing the $PGK1_p$-$PGK1_t$ expression cassette | YPGK |
| pHV1 | pHVX1 with mae1 ORF ($ADH1_p$-mae1-adh1$_t$) | YADH-mae1 |
| pHV2 | pHVX1 with mae2 ORF ($ADH1_p$-mae2-adh1$_t$) | YADH-mae2 |
| pHV3 | pHVX2 with mae1 ORF ($PGK1_p$-mae1-$PGK1_t$) | YPGK-mae1 |
| pHV4 | pHVX2 with mae2 ORF ($PGK1_p$-mae2-$PGK1_t$) | YPGK-mae2 |
| pHV5 | Combination of pHV1 and pHV4 to give a YEplac181-based vector containing the $ADH1_p$-mae1-$ADH1_t$/$PGK1_p$-mae2-$PGK1_t$ expression system | MAL1 |

TABLE 1-continued

Constructs used to engineer a malate degrading pathway in
S. cerevisiae YPH259 (19)

| Name of construct | Description | Recombinant strains |
|---|---|---|
| pHV6 | Combination of pHV2 and pHV3 to give a MAL2 YEplac181-based vector containing the ADH1$_p$-mae2-ADH1$_t$/PGK1$_p$-mae1-PGK1$_t$ expression system | |

TABLE 2

Different strains and plasmids employed in the genetic
construction of malolactic strains of S. cerevisiae.

| | Description | Ref. |
|---|---|---|
| Strains | | |
| E. coli JM109 | endA1, recA1, gyrA96, thi, hsdR17 [r$_{k-1}$m$_k$+], relA1, supE44, λ⁻, Δ(lac-proAB), [F¹, traD36, proA⁺B⁺, lacI$^q$ZΔM15] | |
| S. cerevisiae | a ura3-52, lys2-801$^{amber}$, ade2-101$^{ochre}$, his3Δ200, leu2-Δ1 | Sikorski and Hieter, 1989 |
| Plasmids | | |
| PHVX2 | Expression vector containing only the PGK1 promoter and terminator sequences | FIG. 15 |
| pHV3 | Multicopy episomal plasmid containing the mae1 ORF inserted between the PGK1 promoter and terminator sequences | FIG. 15 |
| pMDMALO | Multicopy episomal plasmid containing the mleS ORF inserted between the PGK1 promoter and terminator sequences. | Denayrolles et al., 1995 |

FULL CITATIONS FOR REFERENCES
REFERRED TO IN THE SPECIFICATION

REFERENCES (These references are incorporated herein by reference thereto).

1. C. Gao, G. H. Fleet, *Food Microbiol.* 12, 65 (1995).
2. H. J. J. van Vuuren, L. M. T. Dicks, *Am. J. Enol. Vitic.* 44, 99 (1993).
3. C. R. Davies, W. Wibowo, R. Eschenbruch, T. H Lee, G. H. Fleet, *Am. J. Enol. Vitic.* 36, 290 (1985).
4. R. E. Kunkee, *FEMS Microbiol. Rev.* 88, 55 (1991).
5. R. B. Beelman, J. F. Gallander,. *Adv. Food Res.* 25, 1 (1979).
6. J. F. Gallander, *Am. J. Enol. Vitic.* 28, 65 (1977).
7. F. Radler, in *Wine Microbiology and Biotechnology*, G. H. Fleet, Ed. (Chur, Harwood Academic, 1993), pp. 165–182.
8. E. Fuck, G. Stark, F. Radler, *Arch. Mikrobiol.* 89, 223 (1973).
9. A. Temperli, V. Kunsch, K. Mayer, I. Busch, *Biochem. Biophys. Acta.* 110, 630 (1965).
10. S. B. Rodriquez, R. J. Thornton, *FEMS Microbiol. Lett.* 72, 17 (1990).
11. M. Denayrolles, M. Aigle, A. Lonvaud-Funel, *FEMS Microbiol. Lett.* 125, 37 (1995).
12. S. A. Williams, R. A. Hodges, T. L. Strike, R. Snow, R. E. Kunkee, *Appl. Environ. Microbiol.* 47, 288 (1984).
13. J. Grobler, F. Bauer, R. E. Subden, H. J. J. van Vuuren, *Yeast* 11, 1485 (1996).
14. E. Maconi, P. Manachini, F. Aragozzini, C. Gennari, G. Ricca, *Biochem. J.* 217, 585 (1984).
15. R. D. Gietz, A. Sugino, *Gene* 74, 527 (1988).
16. R. S. Sikorski, P. Hieter, *Genetics* 122, 19 (1989).
17. B. Martineau, T. Henick-Kling, T. Acree, *Am. J. Enol. Vitic.* 46, 385 (1995).
18. D. C. Burke, *J. Appl. Bacteriol. Symposium Supplement* 79, 1 (1995).
19. R. B. Boulton, V. L. Sinleton, L. F. Bisson and R. E. Kunkee, Malolactic fermentation, In *Principles and practices of winemaking*, pp. 244–273 (1996).
20. E. Carre, S. Lafon-Lafourcade, A. Bertrand, *Connaissance de la Vigne et du Vin* 17, 43–53 (1983).
21. J. M. Crous, I. S. Pretorius and W. H. Van Zyl, *Curr. Genet* 28 467–473 (1995).
22. M. Denayrolles, M. Aigle and A. Lonvaud-Funel, *FEMS Micriobiol. Lett.* 116, 79–86, (1994).
23. T. Henick-Kling, In *Wine Microbiology and Biotechnology*, pp. 289–326, Switzerland: Harwood Academic Publishers (1993).
24. R. E. Kunkee, *Adv. Appl. Microbiol.* 9, 235–79 (1974).
25. A. Lautensach and R. E. Subden, *E. coli. Microbios.* 39, 29–39 (1984).
26. K. Mayer and A. Temperli, *Arch. Mikrobiol.* 46, 321–328 (1963).
27. M. J. Sousa and C. Leao, *Yeast*, 8, 1025–1031 (1992).
28. Alfa, C., Fantes, P., Hyams, J., McLeod, M. and Warbrick, E. (1993). In: Experiments with fission yeast: a laboratory course manual. Cold Spring Harbor laboratory Press, USA. pp 1–186.
29. Altschul, S. F., Gish, W., Miller, W., Myers, E. W. and Lipman, D. J. (1990). Basic local alignment search tool. J. Mol. Biol. 215, 403–410.
30. Ansanay, V., Dequin, S., Blondin, B. and Barre, P. (1993). Cloning, sequence and expression of the gene encoding the malolactic enzyme from *Lactococcus lactis*. FEBS Lett. 332, 74–80.
31. Baranowski, K. and Radler, F. (1984). The glucose-dependant transport of L-malic acid in *Zygosaccharomyces bailii*. Antonie van Leeuwenhoek J. Microbiol. 50, 329–340.
32. Beach, D., Piper, M. and Nurse, P. (1982). Construction of a *Schizosaccharomyces pombe* gene bank in a yeast shuttle vector and its use to isolate genes by complementation. Mol. Gen. Genet. 187, 326–329.
33. Bisson, L. F., Coons, D. M., Kruckeberg, A. L. and Lewis, D. A. (1993). Yeast sugar transporters, Crit. Rev. Biochem. Mol. Biol. 28, 259–308.
34. Cassio, F. and Leão, C. (1993). A comparative study on the transport of L(-) malic acid and other short-chain carboxylic acids in the yeast *Candida utilis*: Evidence for a general organic acid permease. Yeast 9, 743–752.
35. Côrte-Real, M. and Leão, C. (1990). Transport of malic acid and other dicarboxylic acids in the yeast *Hansenula anomala*. Appl. Environ. Microbiol. 56, 1109–1113.
36. Côrte-Real, M. and Leão, C. and Van Uden, N. (1989). Transport of L-malic acid and other dicarboxylic acids in the yeast *Candida sphaerica*. Appl. Microbiol. Biotechnol. 31, 551–555.
37. Davey, J. (1992). Mating pheromones of the fission yeast *Schizosaccharomyces pombe*: purification and structural characterization of M-factor and isolation and analysis of two genes encoding the pheromone. EMBO J. 11, 951–960.
38. Denayrolles, M., Aigle, M. and Lonvaud-Funel, A. (1995). Functional expression in *Saccharomyces cerevisiae* of the *Lactococcus lactis* mleS gene encoding the malolactic enzyme. FEMS Lett. 125, 37–44.

39. Devereux, J., Haeberli, P. and Smithies, O. (1984). A comprehensive set of sequence analysis programs for the VAX. Nucl. Acids Res. 12, 387–395.
40. Eisenberg, D., Schwarz, E., Komaromy, M, and Wall, R. (1984). Analysis of membrane and surface protein sequences with the hydrophobic moment plot. J. Mol. Biol. 179, 125–142.
41. Hoffman, W. (1985). Molocular characterization of the CAN1 locus in *Sacchromyces cerevisiae*. J. Biol. Chem. 260, 11831–11837.
42. Kyte, J. and Doolittle, R. F. (1982). A simple method for displaying the hydropathic character of a protein. J. Biol. Chem. 157, 105.
43. Landschulz, W. H., Johnson, P. F. and McKnight, S. L. (1988). The leucine zipper: a hypothetical structure common to a new class of DNA binding proteins. Science 240, 1759–1764.
44. Lee, S. and Rasheed, S. (1990). A simple procedure for maximum yield of high-quality plasmid DNA. BioTechniques 9, 676–679.
45. Osothsilp, C. (1987). Ph.D.thesis, University of Guelph, Ontario, Canada.
46. Osothsilp, C. and Subden, R. E. (1986a). Isolation and characterization of *Schizosaccharomyces pombe* mutants with defective NAD-dependant malic enzyme. Can J. Microbiol. 32,481–486.
47. Osothsilp, C. and Subden, R. E. (1986b). Malate transport in *Schizosaccharomyces pombe*. J. Bacteriol. 168, 1439–1443.
48. Prentice, H. L. (1992). High efficiency transformation of *Schizosaccharomyces pombe*. J. Bacteriol. 20, 621.
49. Radler, F. (1993). Yeast-metabolism of organic acids. In Wine Microbiology and Biotechnology. Ed. G. H. Fleet, Harwood Academic Publishers, Australia, p.p. 165–182.
50. Rao, M. J. K. and Argos, P. (1986). A conformational preference parameter to predict helices in integral membrane protein. Biochim. Biophys. Acta 869, 197–214.
51. Rodriques, S. B. and Thorton, R. J. (1990). Factors influencing the utilisation of L-malate by yeasts. FEMS Microbiology Letters 72, 17–22.
52. Rogers, S., Wells, R. and Rechsteiner, M. (1986). Amino acid sequence common to rapidly degraded proteins: The PEST hypothesis. Science 234, 364–368.
53. Sambrook, J., Fritsch, E. F. and Maniatis, T. (1989). Molecular cloning. A Laboratory Manual, 2nd edn. Cold Spring Harbor, N.Y.
54. Sikorski, R. S. and Hieter, P. (1989). A system of shuttle vectors and yeast host strains designed for efficient manipulation of DNA in *Saccharomyces cerevisiae*. Genetics 122, 19–27.
55. Sousa, M. J., Mota, M. and Leâo, C. (1992). Transport of malic acid in the yeast *Schizosaccharomyces pombe*: evidence for a protondicarboxylate symport. Yeast 8, 1025–1031.
56. Tabor, S. and Richardson, C. (1987). DNA sequence analysis with modified bacteriophage T7 DNA polymerase. Proc. Natl. Acad. Sci. USA 84, 4767–4771.
57. Tschumper, G. and Carbon, J. (1980). Sequence of a yeast DNA fragment containing a chromosomal replicator and the TRP1 gene. Gene 19, 1157–1166.
58. Tschopp, J. F., Emr, S. D., Field, D. and Schekman, R. (1986). GAL2 codes for a membrane-bound subunit of the g alactose permease in *Saccharomyces cerevisiae*. J. Bacteriol. 166, 31.
59. Viljoen, M., Subden, R. E., Krizus, A. and Van Vuuren, H. J. J. (1994). Molecular analysis of the malic enzyme gene (mae2) of *Schizosacharomyces pombe*. Yeast 10, 613–624.
60. White, M. K. and Weber, M. J. (1989). Leucine zipper motif upd ate. Nature (London) 340, 103–104.
61. Williams, S. A., Hodges, R. A., Strike, T. L., Snow, R. and Kunkee, R. E. (1984). Cloning the gene for the malolactic fermentation of wine from *Lactobacillus delbrueckii* in *Escherichia coli* and yeasts. Appl. Environ. Microbiol. 47, 288–293.
62. Carrau, J. L. et al., 1982, Rev. Brasil. Genet. 1: 221–226.
63. Fernan dez, M. J. et al., 1967, Eur. J. Biochem. 3: 11–18.
64. Goto, S., et al., 1978, Hakkokogaku, 56: 133–135.
65. Kuczynski, J. T. and F. Radler, 1982, Arch. Microbiol. 131: 266–270.
66. Svoboda, A., 1980. Intergeneric fusion of yeast protoplast: *Saccharomyces cerevisiae* & *Schizosaccharomyces pombe*. In Advances in protoplast research.
Edited by H. Szeged. Pergamon Press. Oxford, Toronto, pp 119–124.

Detailed Figure Legends for FIGS. 1 to 15

Figure 2:
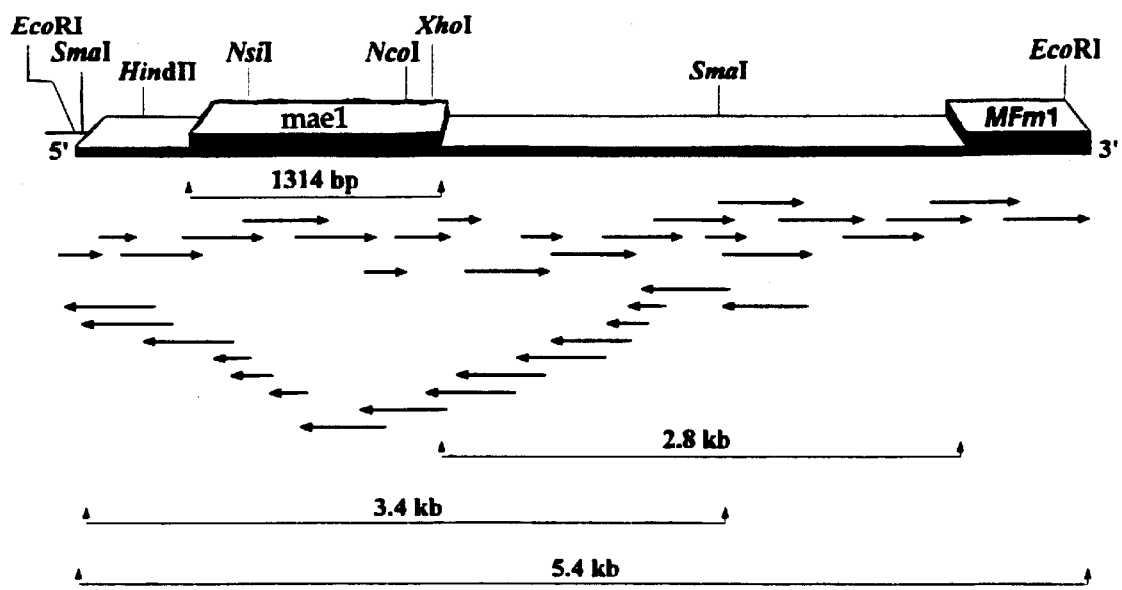
FIG. 2 shows a restriction map and DNA sequencing strategy for the coding and 3' region of the mae1 gene and the MFm1 gene.

FIG. 1. Chromosomal blotting of the mae1 gene. *S. pombe* chromosomes were separated on a CHEF gel (left) and probed with the labeled internal Nsi1/Xho1 fragment of mae1 (right).

FIG. 2. Restriction map and DNA sequencing strategy for the coding and 3' region of the mae1 gene and the MFm1 gene. Only unique restriction sites that occur within the mae1 gene are shown. Overlapping exonuclease fragments were generated for sequencing as indicated by the arrows. Both strands of the mae1 gene were sequenced entirely whereas only one strand of the MFm1 gene was sequenced.

FIG. 3. Nucleotide and deduced aa sequence of the mae1 gene. Nucleotides are numbered on the left, and amino acids, designated by the standard single-letter codes, are numbered on the right. The arrows connecting residues 421 and 434 enclose a PEST sequence; the circled serine and threonine are the potential phosphorylation sites in the PEST sequence. The putative membrane-spanning segments are shown as solid boxes. The circled asparagines (N) are possible glycosylation sites. Stars indicate a putative leucine zipper. At the 5' end the putative "TATA" box is underlined.

Figure 4:
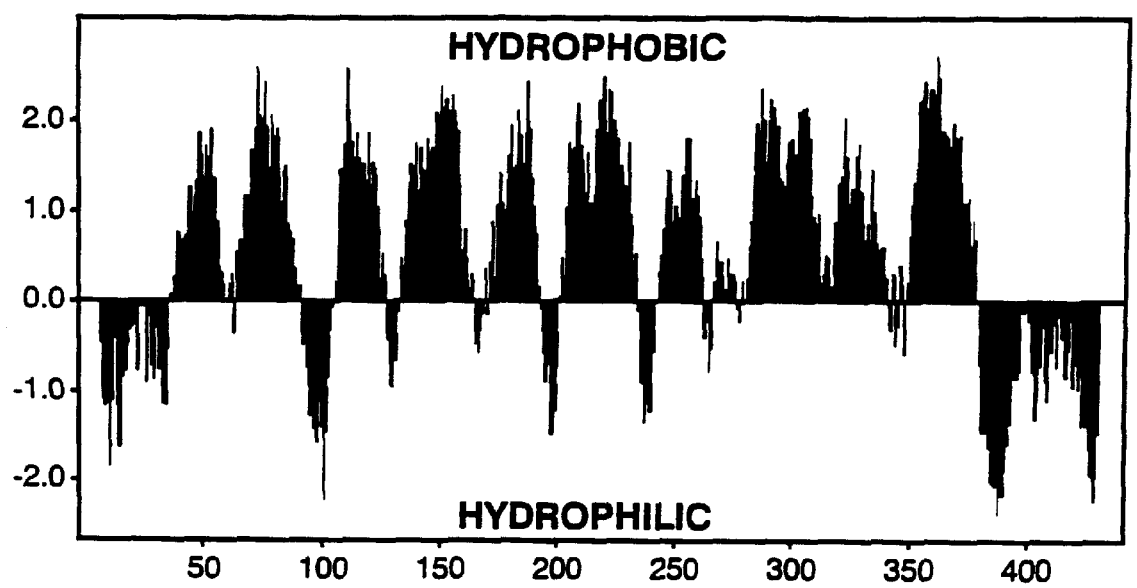
FIG. 4 shows a hydropathy plot of the predicted mae1 protein.

FIG. 4. Hydropathy plot of the predicted mae1 protein. The profile was determined by the algorithm of Kyte and Doolittle (1982) using a window of 10 aa.

FIG. 5. Model showing the proposed distribution of the hydrophobic membrane domains which are numbered from 1 to 10. The N-glycosylation sites (Y), leucine zipper pattern (connecting domains 6 and 7) and PEST region (open cylinder near —COOH end) are indicated on e model. The model was constructed from the analysis of the mae1 protein using the methods of Eisenburg et al. (1984) and Rao and Argos (1986).

Figure 6:
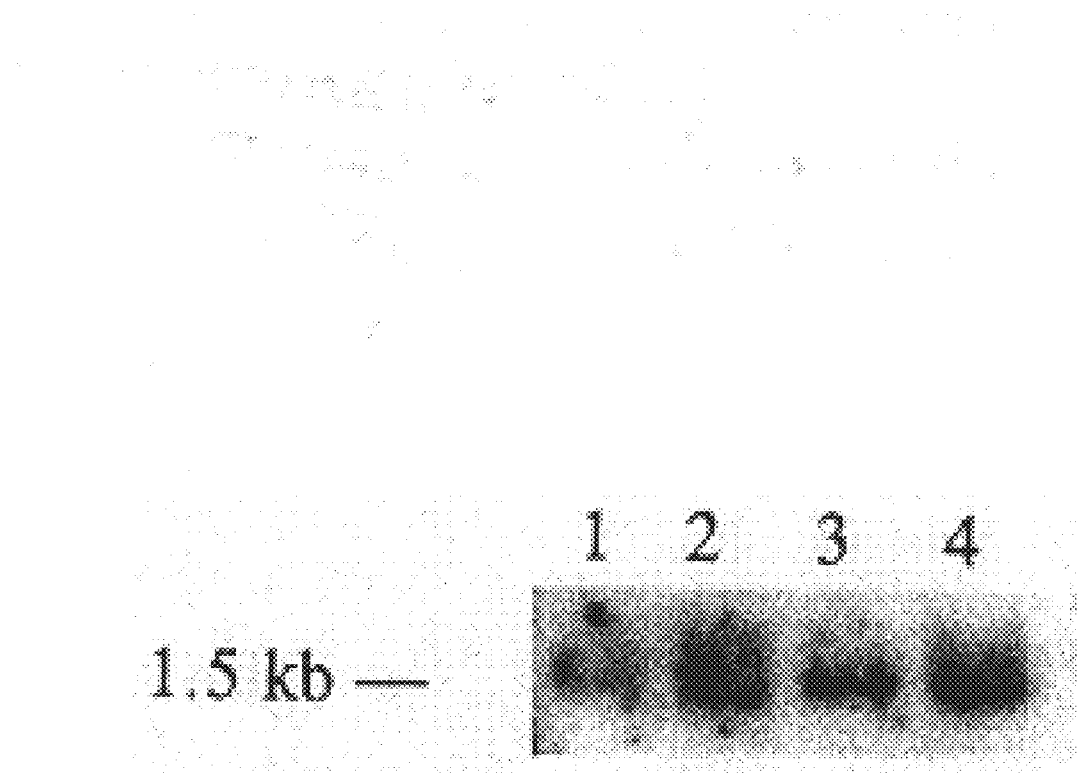
FIG. 6 shows a Northern blot of wild-type *S. pombe* total RNA, probed with 695 bp Nsi1/Xho1 fragment of mae1.

FIG. 6. Northern blot of wild-type *S. pombe* total RNA, probed with the 695 bp Nsi/Xhol fragment of mae1. Cells were grown in glucose (1), fructose (2), fructose buffered with 10 mM succinate at pH 6.0 (3) or raffinose (4) as sole carbon source.

FIG. 7. Uptake of [$^{14}$C] L-malic acid (a) and [$^{14}$C] succinic acid (b) by the wild-type (Δ), mae1⁻ mutant (o) and complemented mutant (□). The transport of L-malic and succinic acid by the mutant was fully restored by transforming the cells with the mae1 gene. Similar results were obtained when [$^{14}$C] malonic acid was used (data not shown).

Figure 8:
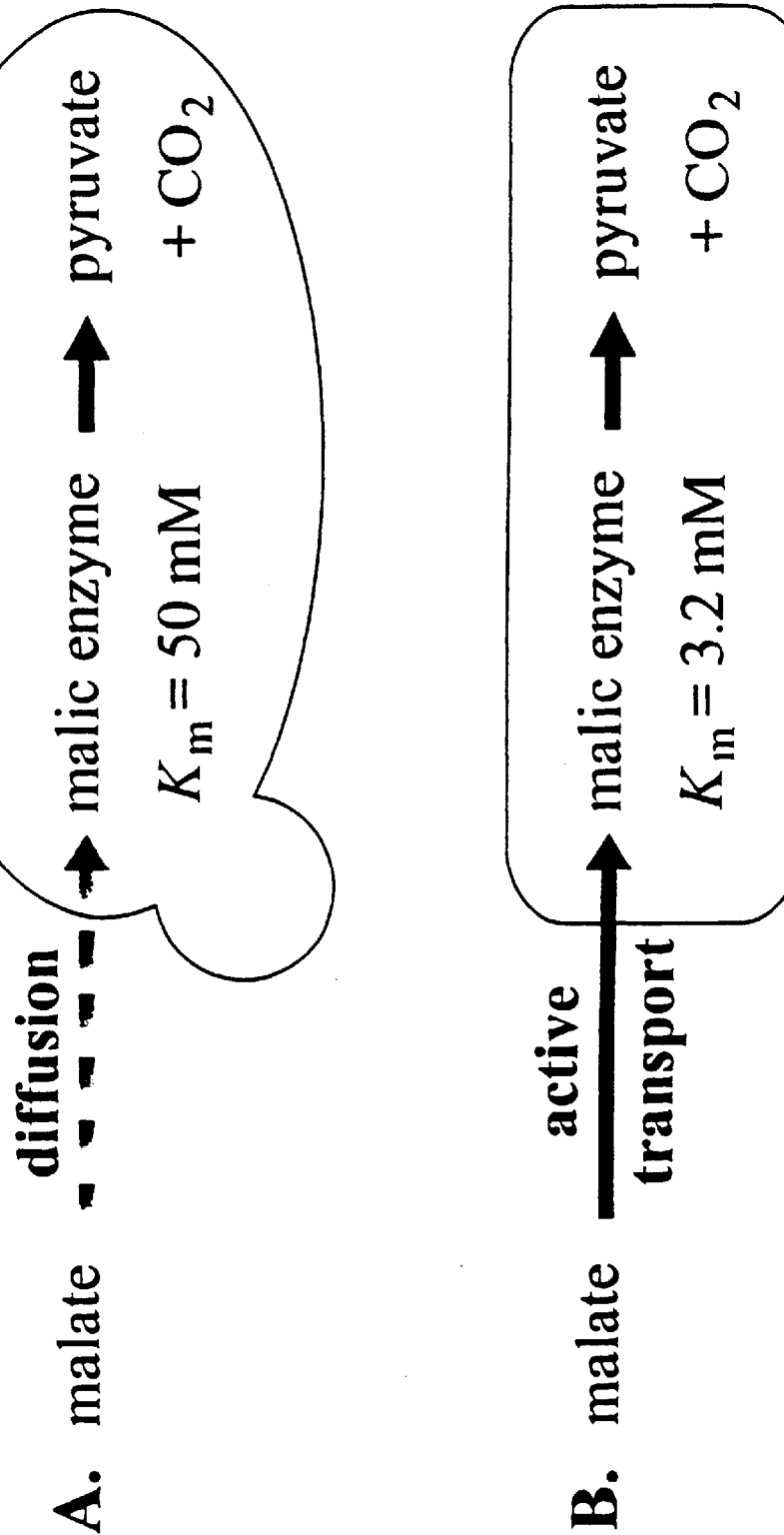
FIG. 8 shows an overview of the permeability and transport and degradation of malate by (A) *S. cerevisiae* and (B) *S. pombe;*

FIG. 8. (A) *S. cerevisiae* cannot degrade malate efficiently due to the absence of a malate transporter and a malic enzyme with a low substrate affinity ($K_m$=50 mM). (B) In contrast, *S. pombe* degrades malate actively as this yeast contains a permease for malate and other $C_4$ dicarboxylic acids. In addition, the substrate affinity of the *S. pombe* malic enzyme is considerably higher than that of the *S. cerevisiae* enzyme.

Figure 9:
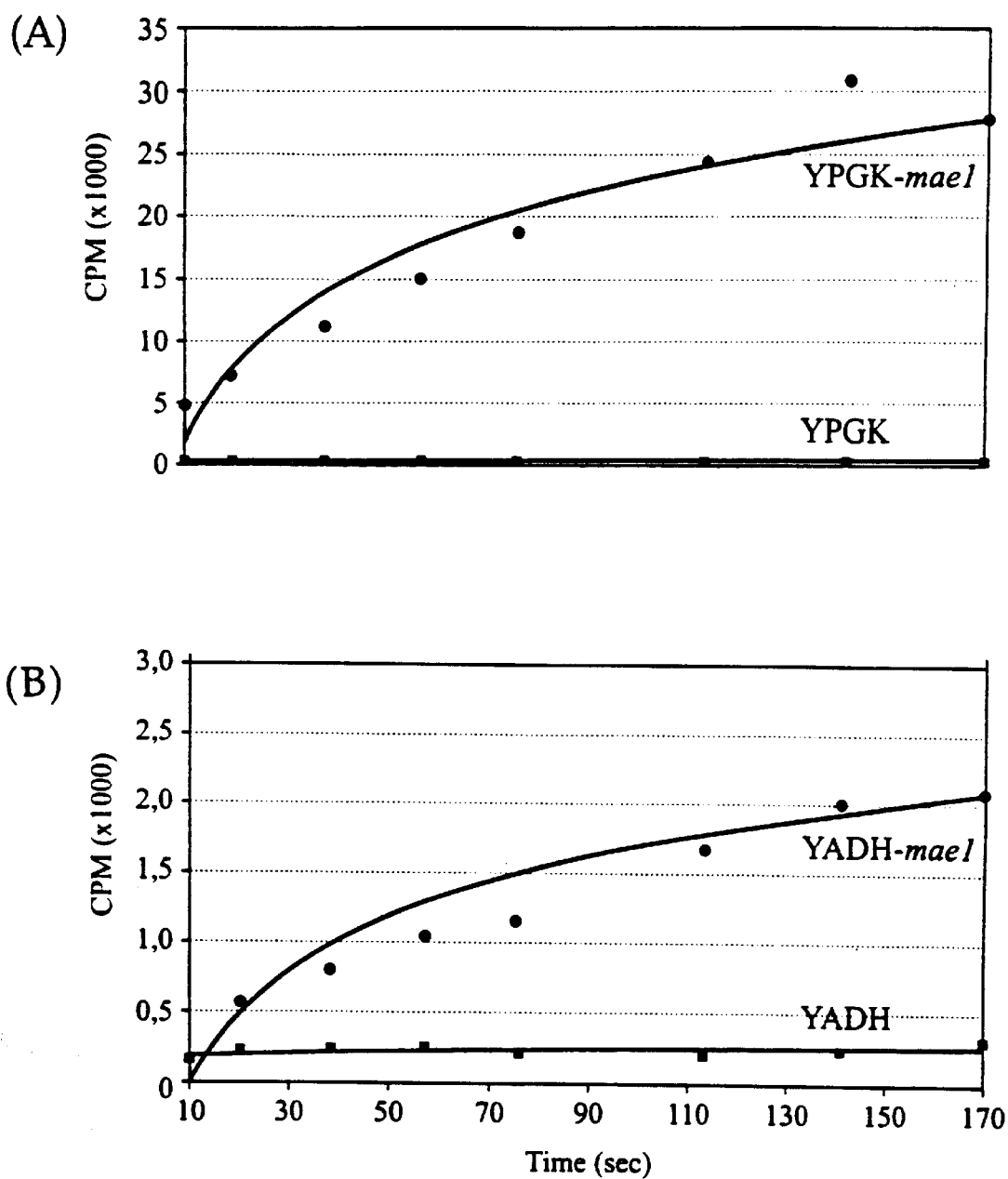
FIG. 9 shows the uptake of $^{14}$C L-malate by recombinant strains of *S. cerevisiae* containing the mae1 gene of *S. pombe* under the regulation of (A) the PGK1 promoter and (B) the ADH1 promoter.

FIG. 9. Uptake of $^{14}C$ L-malate by recombinant strains of *S. cerevisiae* containing the mae1 gene of *S. pombe* under the regulation of (A) the PGK1 promoter and (B) the ADH1 promoter, according to Grobler et al. (14). The cells were cultured to $OD_{600}$=0.6 in a 2% glucose medium, containing 0.17% yeast nitrogen base [without amino acids and $(NH_4)_2SO_4$] and 0.5% $(NH_4)_2SO_4$, 0.002% adenine, uracil and histidine and 0.003% lysine.

FIG. 10. Malate degradation by the recombinant strains of *S. cerevisiae* containing the mae1 and/or mae2 genes of *S. pombe* in 2% glycerol-ethanol medium containing 8–9 g/lL-malate. The glycerol/ethanol and the glucose media were supplemented as indicated in FIG. 9. The malate concentration during fermentation was measured enzymatically with the 1-malic Acid Test Kit from Boehringer Mannheim. Malate degradation was regarded as complete with the concentration reached 0.3 g/l L-malate (malolactic fermentation is considered to be complete at this point during vinification).

FIG. 11. Malate degradation by the recombinant strains of *S. cerevisiae* containing the mae1 and/or mae2 genes of *S. pombe* in 2% glucose medium containing 8–9 g/lL-malate. The glycerol/ethanol and the glucose media were supplemented as indicated in FIG. 9. The malate concentration during fermentation was measured enzymatically with the 1-malic Acid Test Kit from Boehringer Mannheim. Malate degradation was regarded as complete with the concentration reached 0.3 g/l L-malate (malolactic fermentation is considered to be complete at this point during vinification).

FIG. 12. Degradation of L-malate in Cabernet Sauvignon grape must by recombinant strains of *S. cerevisiae*. Malolactic fermentation was regarded as complete when the concentration of L-malate reached 0.3 g/l (Martineau et al., 1995). The MLF1 strain of *S. cerevisiae* containing the malate permease gene (mae1) of *S. pombe* and the malolactic gene (mleS) of *L. lactis* completely degraded L-malate in Cabernet Sauvignon grape must. Malate was not degraded by the control yeasts containing the PGK1 expression cassette (pHVX2) or the mleS gene (pMDMALO) or the mae1 gene (pHV3) individually.

FIG. 13. Degradation of L-malate in Chardonnay grape must by recombinant strains of *S. cerevisiae*. Malolactic fermentation was regarded as complete when the concentration of L-malate reached 0.3 g/l (Martineau et al., 1995). The MLF1 strain of *S. cerevisiae* containing the malate permease gene (mae1) of *S. pombe* and the malolactic gene (mleS) of *L. lactis* completely degraded L-malate in both Cabernet Sauvignon and Chardonnay grape must. Malate was not degraded by the control yeasts containing the PGK1 expression cassette (pHVX2) or the mleS gene (pMDMALO) or the mae1 gene (pHV3) individually.

FIG. 14. Malolactic fermentation by the recombinant yeast strains of *S. cerevisiae* in Cabernet Sauvignon (A) and Chardonnay (B) wines after fermentation. Lanes A3 and B3 correspond to the must fermented with MLF1. The first and second lanes (A and B) correspond to the control yeast containing only the PGK1 expression cassette (pHVX2) or the mleS gene (pMDMALO), respectively.

FIG. 15. Subcloning of the *S. pombe*'s mae1 ORF under control of the PGK1 promoter and terminator sequences in pHVX2, a derivative of Yeplac181 (Sikorski and Hieter, 1989).

We claim:

1. An isolated nucleic acid molecule comprising a sequence which encodes a eukaryotic malate permease from *Schizosaccharomyces pombe* which mediates the uptake of L-malate, succinate, and malonate.

2. An isolated nucleic acid molecule as claimed in claim 1 wherein the protein contains a PEST region, and a leucine zipper motif and at least one transmembrane domain.

3. An isolated nucleic acid molecule comprising
   (i) a nucleic acid sequence encoding a protein having the amino acid sequence shown in SEQ ID NO: 2; or
   (ii) nucleic acid sequences complementary to (i).

4. An isolated nucleic acid molecule comprising
   (i) a nucleic acid sequence as shown in SEQ ID NO:1, wherein T can also be U;
   (ii) nucleic acid sequences complementary to (i); or
   (iii) a nucleic acid encoding a malate permease and capable of hybridizing under stringent conditions to a nucleic acid of (i) wherein the stringent conditions comprise 6.0×sodium chloride/sodium citrate (SSC) at about 45° C., followed by a wash of 2.0×SSC at about 50° C.

5. An isolated nucleic acid molecule comprising a sequence encoding a truncation of a protein having the amino acid sequence shown in SEQ ID NO: 2 and having malate permease activity.

6. An isolated nucleic acid probe encoding at least 6 sequential amino acids from the sequence shown in SEQ.ID.NO.:2.

7. A method of isolating a nucleic acid according to claim 1, 3, 5, or 6 comprising contacting a nucleic acid containing sample with a nucleic acid probe encoding at least 6 sequential amino acids from the sequence shown in SEQ.ID.NO.:2, under conditions which permit the hybridization of the probe with the nucleic acid molecule if present in the sample and isolating the nucleic acid molecule.

8. An isolated nucleic acid molecule according to claim 1, 3, 4 or 5 obtainable by a method comprising contacting a nucleic acid containing sample with a nucleic acid probe encoding at least 6 sequential amino acids from the sequence shown in SEQ.ID.NO.:2 under conditions which permit the hybridization of the probe with the nucleic acid molecule in the sample and isolating the nucleic acid molecule.

9. A recombinant expression vector adapted for transformation of a host cell comprising a nucleic acid molecule as claimed in any one of claims 1, 3, 4, or 5.

10. A recombinant expression vector adapted for transformation of a host cell comprising a nucleic acid molecule as claimed in claim 8.

11. A recombinant expression vector according to claim 9 further comprising a nucleic acid molecule encoding a malic enzyme, a malolactic enzyme, or an enzyme involved in the metabolism of malate in plants.

12. A recombinant expression vector as claimed in claim 11, wherein the malic enzyme is from *S. pombe*.

13. An recombinant expression vector as claimed in claim 11, wherein the malolactic enzyme is from Leuconostoc, Lactobacillus or Pediococcus.

14. A eukaryotic host cell having integrated into its genome a nucleic acid molecule as claimed in claim 1.

15. A eukaryotic host cell transformed with a recombinant expression vector according to claim 9.

16. A eukaryotic cell according to claim 14 wherein the cell further contains a nucleic acid molecule encoding a malolactic enzyme.

17. A eukaryotic cell according to claim 14 wherein the cell further contains a nucleic acid molecule encoding a malic enzyme.

18. A eukaryotic cell according to claim 14 wherein the cell degrades at least 27% L-malate in solution.

19. A eukaryotic cell according to claims 14 wherein the cell completely degrades L-malate in grape musts.

20. A eukaryotic cell according to claim 14 wherein the cell degrades L-malate during alcoholic fermentation.

21. A eukaryotic cell according to claim 14 wherein the cell degrades L-malate during the alcoholic fermentation of wine.

22. A eukaryotic cell according to claim 14 wherein the cell degrades L-malate to L-lactate and $CO_2$.

23. A eukaryotic cell according to claim 14 wherein the cell degrades L-malate to ethanol and $CO_2$.

24. A eukaryotic cell as claimed in claim 14 which is a yeast strain.

25. A eukaryotic cell according to claim 24 which is Saccharomyces.

26. A eukaryotic cell as claimed in claim 25 which is *Saccharomyces cerevisiae* or *Saccharomyces bayanus*.

27. A eukaryotic host cell having integrated into its genome a nucleic acid molecule as claimed in claim 8.

28. A method of increasing uptake of L-malate, succinic acid or malonate in a cell comprising transforming the cell with a nucleic acid molecule as claimed in claim 1.

29. A method for preparing a protein which mediates the uptake of L-malate, succinate, and malonate comprising (a) transferring a recombinant expression vector as claimed in claim 9 into a host cell; (b) selecting transformed host cells from untransformed host cells; (c) culturing a selected transformed host cell under conditions which allow expression of the protein; and (d) isolating the protein.

30. An isolated protein characterized in that it is encoded by a nucleic acid according to any one of claims 1, 3, 4 or 5 and in that it mediates the uptake into a cell of external L-malate, succinate, and malonate.

31. An isolated protein as claimed in claim 30 further characterized in that it has the enzymatic activity of Mae1 from *S. pombe*.

32. An isolated protein as claimed in claim 31 which has the amino acid sequence as shown in SEQ ID NO:2.

33. An isolated protein which is a truncation, of the protein which has the amino acid sequence as shown in SEQ.ID.NO.:2, which mediates the uptake into a cell of external L-malate, succinate and malonate and has malate permease activity.

34. An isolated protein characterized in that it is encoded by a nucleic acid according to claim 8 and in that it mediates the uptake into a cell of external L-malate, succinate, and malonate.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2460 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Schizosaccharomyces pombe (vii) IMMEDIATE SOURCE:
      (B) CLONE: Mae1

(ix) FEATURE:
      (A) NAME/KEY: CDS
      (B) LOCATION: 379..1695

(xi) SEQUENCE DESCRIPTION: SEQ ID NO:1:

```
TGATCACTAT TTGTTTGTTC TATTTTTGTT TTCTTTTACT TGTTTGCTAC ACAAAATAAG      60

CTTATTTGTT GCTGCACTAG ACTTTTTGTT TGATTTCTCA TCCTACTTCT GTATCGGCAG     120

TTTGCTCATT TACTAAGACT AGCAACAGCC AGTCATTCAT TTTTTACACT CTCTATCATT     180

TTTTATTTTC ATCACGATAA CTAACATGTG CGATTAGACT CACAGATAAA TTGCTAGCAA     240
```

```
TTGGTTGTCT CTTTCCTTCC TCCGTCTTTT CCTTTTTGTT CCTTTTCTC CTTATATTAT        300

ATTATATTAT ATTCATTCTT CATTTTCTCT CTTGGCCACT ATTTTTTTTT TTAATTCCCC        360

TTTATCTCTC GATTCGAC ATG GGT GAA CTC AAG GAA ATC TTG AAA CAG AGG          411
                    Met Gly Glu Leu Lys Glu Ile Leu Lys Gln Arg
                     1               5                  10

TAT CAT GAG TTG CTT GAC TGG AAT GTC AAA GCC CCT CAT GTC CCT CTC          459
Tyr His Glu Leu Leu Asp Trp Asn Val Lys Ala Pro His Val Pro Leu
         15                  20                  25

AGT CAA CGA CTG AAG CAT TTT ACA TGG TCT TGG TTT GCA TGT ACT ATG          507
Ser Gln Arg Leu Lys His Phe Thr Trp Ser Trp Phe Ala Cys Thr Met
             30                  35                  40

GCA ACT GGT GGT GTT GGT TTG ATT ATT GGT TCT TTC CCC TTT CGA TTT          555
Ala Thr Gly Gly Val Gly Leu Ile Ile Gly Ser Phe Pro Phe Arg Phe
     45                  50                  55

TAT GGT CTT AAT ACA ATT GGC AAA ATT GTT TAT ATT CTT CAA ATC TTT          603
Tyr Gly Leu Asn Thr Ile Gly Lys Ile Val Tyr Ile Leu Gln Ile Phe
 60                  65                  70                  75

TTG TTT TCT CTC TTT GGA TCA TGC ATG CTT TTT CGC TTT ATT AAA TAT          651
Leu Phe Ser Leu Phe Gly Ser Cys Met Leu Phe Arg Phe Ile Lys Tyr
                 80                  85                  90

CCT TCA ACT ATC AAG GAT TCC TGG AAC CAT CAT TTG GAA AAG CTT TTC          699
Pro Ser Thr Ile Lys Asp Ser Trp Asn His His Leu Glu Lys Leu Phe
             95                 100                 105

ATT GCT ACT TGT CTT CTT TCA ATA TCC ACG TTC ATC GAC ATG CTT GCC          747
Ile Ala Thr Cys Leu Leu Ser Ile Ser Thr Phe Ile Asp Met Leu Ala
         110                 115                 120

ATA TAC GCC TAT CCT GAT ACC GGC GAG TGG ATG GTG TGG GTC ATT CGA          795
Ile Tyr Ala Tyr Pro Asp Thr Gly Glu Trp Met Val Trp Val Ile Arg
 125                 130                 135

ATC CTT TAT TAC ATT TAC GTT GCA GTA TCC TTT ATA TAC TGC GTA ATG          843
Ile Leu Tyr Tyr Ile Tyr Val Ala Val Ser Phe Ile Tyr Cys Val Met
140                 145                 150                 155

GCT TTT TTT ACA ATT TTC AAC AAC CAT GTA TAT ACC ATT GAA ACC GCA          891
Ala Phe Phe Thr Ile Phe Asn Asn His Val Tyr Thr Ile Glu Thr Ala
                160                 165                 170

TCT CCT GCT TGG ATT CTT CCT ATT TTC CCT CCT ATG ATT TGT GGT GTC          939
Ser Pro Ala Trp Ile Leu Pro Ile Phe Pro Pro Met Ile Cys Gly Val
            175                 180                 185

ATT GCT GGC GCC GTC AAT TCT ACA CAA CCC GCT CAT CAA TTA AAA AAT          987
Ile Ala Gly Ala Val Asn Ser Thr Gln Pro Ala His Gln Leu Lys Asn
        190                 195                 200

ATG GTT ATC TTT GGT ATC CTC TTT CAA GGA CTT GGT TTT TGG GTT TAT         1035
Met Val Ile Phe Gly Ile Leu Phe Gln Gly Leu Gly Phe Trp Val Tyr
    205                 210                 215

CTT TTA CTG TTT GCC GTC AAT GTC TTA CGG TTT TTT ACT GTA GGC CTG         1083
Leu Leu Leu Phe Ala Val Asn Val Leu Arg Phe Phe Thr Val Gly Leu
220                 225                 230                 235

GCA AAA CCC CAA GAT CGA CCT GGT ATG TTT ATG TTT GTC GGT CCA CCA         1131
Ala Lys Pro Gln Asp Arg Pro Gly Met Phe Met Phe Val Gly Pro Pro
                240                 245                 250

GCT TTC TCA GGT TTG GCC TTA ATT AAT ATT GCG CGT GGT GCT ATG GGC         1179
Ala Phe Ser Gly Leu Ala Leu Ile Asn Ile Ala Arg Gly Ala Met Gly
            255                 260                 265

AGT CGC CCT TAT ATT TTT GTT GGC GCC AAC TCA TCC GAG TAT CTT GGT         1227
Ser Arg Pro Tyr Ile Phe Val Gly Ala Asn Ser Ser Glu Tyr Leu Gly
        270                 275                 280

TTT GTT TCT ACC TTT ATG GCT ATT TTT ATT TGG GGT CTT GCT GCT TGG         1275
Phe Val Ser Thr Phe Met Ala Ile Phe Ile Trp Gly Leu Ala Ala Trp
    285                 290                 295
```

```
TGT TAC TGT CTC GCC ATG GTT AGC TTT TTA GCG GGC TTT TTC ACT CGA    1323
Cys Tyr Cys Leu Ala Met Val Ser Phe Leu Ala Gly Phe Phe Thr Arg
300             305                 310                 315

GCC CCT CTC AAG TTT GCT TGT GGA TGG TTT GCA TTC ATT TTC CCC AAC    1371
Ala Pro Leu Lys Phe Ala Cys Gly Trp Phe Ala Phe Ile Phe Pro Asn
                320                 325                 330

GTG GGT TTT GTT AAT TGT ACC ATT GAG ATA GGT AAA ATG ATA GAT TCC    1419
Val Gly Phe Val Asn Cys Thr Ile Glu Ile Gly Lys Met Ile Asp Ser
            335                 340                 345

AAA GCT TTC CAA ATG TTT GGA CAT ATC ATT GGG GTC ATT CTT TGT ATT    1467
Lys Ala Phe Gln Met Phe Gly His Ile Ile Gly Val Ile Leu Cys Ile
        350                 355                 360

CAG TGG ATC CTC CTA ATG TAT TTA ATG GTC CGT GCG TTT CTC GTC AAT    1515
Gln Trp Ile Leu Leu Met Tyr Leu Met Val Arg Ala Phe Leu Val Asn
365                 370                 375

GAT CTT TGC TAT CCT GGC AAA GAC GAA GAT GCC CAT CCT CCA CCA AAA    1563
Asp Leu Cys Tyr Pro Gly Lys Asp Glu Asp Ala His Pro Pro Pro Lys
380                 385                 390                 395

CCA AAT ACA GGT GTC CTT AAC CCT ACC TTC CCA CCT GAA AAA GCA CCT    1611
Pro Asn Thr Gly Val Leu Asn Pro Thr Phe Pro Pro Glu Lys Ala Pro
                400                 405                 410

GCA TCT TTG GAA AAA GTC GAT ACA CAT GTC ACA TCT ACT GGT GGT GAA    1659
Ala Ser Leu Glu Lys Val Asp Thr His Val Thr Ser Thr Gly Gly Glu
            415                 420                 425

TCG GAT CCT CCT AGT AGT GAA CAT GAA AGC GTT TAA GCTTGTATGC         1705
Ser Asp Pro Pro Ser Ser Glu His Glu Ser Val *
        430                 435

TTTTCCTTAA TTTTTCTATA AATCTGTGTG CCCTGCTCTT AATACCATTA TAGATTAATC  1765

ATTTTGAATC ATTCTGTATC TTTATTGTAC TACTGGTACT AATTTTGCTT AGACATTTTT  1825

GCTCCTTCTT CTTCTTTTTG TTTAAATTAT ACATACCAAA ATTTTGGACT TGAATAATG   1885

GTAATTTTTG GTTGTCGTAG TGTTAAATAT GTATGCGTCT TGCATATGAA TCACGACGAA  1945

GGAATCAATT AAAAAATCAA TCCTGTACAT AATAAAATTA AGTTTATTTA TTTCATTTTA  2005

TCGGATTTAA TCGTCTAAAA TTTATATCTT GGTCATCCAA GCTTATATCT CTTTCTACTC  2065

TTATCAGCAG CACACTTTAG TTATGGTTAT TTGAAAACTT GTGTATAAAT TCCTGGTTAT  2125

AGAGAAAATG AGTATAAGAC AACAAAAAAA AGCCTAGTCG GCATGCGACA TGTCTCAAAC  2185

ATATCTTTGG CGTATTGATG AGCATCTTAC ACACTCACTA TACGTAACAA TAAAATTAAG  2245

AGGGATTTCA TGACAAAAGA ATACTAGAGT GAAACCACTA TGACTAAAAT AAAAACTGGT  2305

AAAAGGTAAT TCTAAAATAT TAAATCATGT ATAGAAAATA GTCCAATTAA TCAAGATAGC  2365

GTTGAACGTG ACCTGATACT AGATTGCACA AACGAAATAA AACAATCTTG AAGTAAAAGC  2425

AATAGCACAA TAAAAGAGAA GATACCTCAT TTAAC                            2460

(2) INFORMATION FOR SEQ ID NO:2:

(i) SEQUENCE CHARACTERISTICS:
        (A) LENGTH: 438 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Glu Leu Lys Glu Ile Leu Lys Gln Arg Tyr His Glu Leu Leu
 1               5                  10                  15

Asp Trp Asn Val Lys Ala Pro His Val Pro Leu Ser Gln Arg Leu Lys
```

-continued

```
                20                  25                  30
His Phe Thr Trp Ser Trp Phe Ala Cys Thr Met Ala Thr Gly Gly Val
         35                  40                  45
Gly Leu Ile Ile Gly Ser Phe Pro Phe Arg Phe Tyr Gly Leu Asn Thr
 50                  55                  60
Ile Gly Lys Ile Val Tyr Ile Leu Gln Ile Phe Leu Phe Ser Leu Phe
 65                  70                  75                  80
Gly Ser Cys Met Leu Phe Arg Phe Ile Lys Tyr Pro Ser Thr Ile Lys
             85                  90                  95
Asp Ser Trp Asn His His Leu Glu Lys Leu Phe Ile Ala Thr Cys Leu
            100                 105                 110
Leu Ser Ile Ser Thr Phe Ile Asp Met Leu Ala Ile Tyr Ala Tyr Pro
            115                 120                 125
Asp Thr Gly Glu Trp Met Val Trp Val Ile Arg Ile Leu Tyr Tyr Ile
            130                 135                 140
Tyr Val Ala Val Ser Phe Ile Tyr Cys Val Met Ala Phe Phe Thr Ile
145                 150                 155                 160
Phe Asn Asn His Val Tyr Thr Ile Glu Thr Ala Ser Pro Ala Trp Ile
            165                 170                 175
Leu Pro Ile Phe Pro Pro Met Ile Cys Gly Val Ile Ala Gly Ala Val
            180                 185                 190
Asn Ser Thr Gln Pro Ala His Gln Leu Lys Asn Met Val Ile Phe Gly
            195                 200                 205
Ile Leu Phe Gln Gly Leu Gly Phe Trp Val Tyr Leu Leu Leu Phe Ala
            210                 215                 220
Val Asn Val Leu Arg Phe Phe Thr Val Gly Leu Ala Lys Pro Gln Asp
225                 230                 235                 240
Arg Pro Gly Met Phe Met Phe Val Gly Pro Ala Phe Ser Gly Leu
            245                 250                 255
Ala Leu Ile Asn Ile Ala Arg Gly Ala Met Gly Ser Arg Pro Tyr Ile
            260                 265                 270
Phe Val Gly Ala Asn Ser Ser Glu Tyr Leu Gly Phe Val Ser Thr Phe
            275                 280                 285
Met Ala Ile Phe Ile Trp Gly Leu Ala Ala Trp Cys Tyr Cys Leu Ala
            290                 295                 300
Met Val Ser Phe Leu Ala Gly Phe Phe Thr Arg Ala Pro Leu Lys Phe
305                 310                 315                 320
Ala Cys Gly Trp Phe Ala Phe Ile Phe Pro Asn Val Gly Phe Val Asn
            325                 330                 335
Cys Thr Ile Glu Ile Gly Lys Met Ile Asp Ser Lys Ala Phe Gln Met
            340                 345                 350
Phe Gly His Ile Ile Gly Val Ile Leu Cys Ile Gln Trp Ile Leu Leu
            355                 360                 365
Met Tyr Leu Met Val Arg Ala Phe Leu Val Asn Asp Leu Cys Tyr Pro
            370                 375                 380
Gly Lys Asp Glu Asp Ala His Pro Pro Lys Pro Asn Thr Gly Val
385                 390                 395                 400
Leu Asn Pro Thr Phe Pro Pro Glu Lys Ala Pro Ala Ser Leu Glu Lys
            405                 410                 415
Val Asp Thr His Val Thr Ser Thr Gly Gly Glu Ser Asp Pro Pro Ser
            420                 425                 430
Ser Glu His Glu Ser Val
            435
```

(2) INFORMATION FOR SEQ ID NO:3:

(i) SEQUENCE CHARACTERISTICS:
        (A) LENGTH: 1927 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lactococcus lactis (vii) IMMEDIATE SOURCE:
        (B) CLONE: EML (ix) FEATURE:
        (A) NAME/KEY: CDS
        (B) LOCATION: 267..1832

(xi) SEQUENCE DESCRIPTION: SEQ ID NO:3:

```
TTATCATTTA ATAGTTATAA GCTAATTTTT ACTACCATTT CTTTGATTAA TATCATCTAT      60

TTTTATATAG AGACTTTTAA ATAAACATTG ACATTATTTA TGCGTTATAA ATAAAATTTA     120

TCAACACTAA GGAATTTGAC TATAACGATA AAAGAAGTTT ATAGTAATAA AGTAATAACA     180

TTAATTATAA TTTTTATGGA GGTTGTACGA TGCGTGCACA TGAAATTTTA AACAATCCTT     240

TTTTAAATAA AGGAACAGCT TTTACT ATG AAA GAA CGT CAA GAA TTG GGG TTG      293
                             Met Lys Glu Arg Gln Glu Leu Gly Leu
                              1               5

ATT GGT CTT CTT CCA CCA ACT GTT CAA ACA ATT GAG GAA CAA GCT GAA      341
Ile Gly Leu Leu Pro Pro Thr Val Gln Thr Ile Glu Glu Gln Ala Glu
 10              15                  20                  25

CAA ACT TAC GAA CAA TAT TTG ACA AAA CCA TCT GAT TTA GAA AAA CGT      389
Gln Thr Tyr Glu Gln Tyr Leu Thr Lys Pro Ser Asp Leu Glu Lys Arg
                 30                  35                  40

CAT TTC TTG ATG GAA ATT TTT AAT ACA AAC CGT ACT TTG TTT TAC TAC      437
His Phe Leu Met Glu Ile Phe Asn Thr Asn Arg Thr Leu Phe Tyr Tyr
             45                  50                  55

TTA TTC AAC AAA CAT ATT GTA GAA TTT AAT CCA GTT GTT TAT GAT CCA      485
Leu Phe Asn Lys His Ile Val Glu Phe Asn Pro Val Val Tyr Asp Pro
         60                  65                  70

ACA ATT GCT GAT ACA ATT GAA AAC TAC AGT CAT TTG TTC GTA GAT CCA      533
Thr Ile Ala Asp Thr Ile Glu Asn Tyr Ser His Leu Phe Val Asp Pro
 75                  80                  85

CAA TAT GCT GCT TAT CTT GAT ATT AAC CAC CCT GAA AAC ATT ACT GAA      581
Gln Tyr Ala Ala Tyr Leu Asp Ile Asn His Pro Glu Asn Ile Thr Glu
 90                  95                 100                 105

ACA TTG AAA AAT GCA GCA GGT GAC AGA GAA ATT CGT CTT ATT GTT GTA      629
Thr Leu Lys Asn Ala Ala Gly Asp Arg Glu Ile Arg Leu Ile Val Val
                110                 115                 120

ACT GAT GCT GAA GGA ATC CTT GGT ATT GGA GAC TGG GGA ACT CAA GGT      677
Thr Asp Ala Glu Gly Ile Leu Gly Ile Gly Asp Trp Gly Thr Gln Gly
            125                 130                 135

GTT GAT ATC TCA GTT GGT AAA TTA ATG ATT TAT ACA GCC GCA GCA GGT      725
Val Asp Ile Ser Val Gly Lys Leu Met Ile Tyr Thr Ala Ala Ala Gly
        140                 145                 150

ATT GAT CCA GCG TCT GTA CTT CCA GTT GTT ATT GAT GCA GGA ACA AAT      773
Ile Asp Pro Ala Ser Val Leu Pro Val Val Ile Asp Ala Gly Thr Asn
155                 160                 165

AGA AAA GAA CTT TTA GAA GAT CAT TTG TAT CTT GGA AAT CAT CAA GAA      821
Arg Lys Glu Leu Leu Glu Asp His Leu Tyr Leu Gly Asn His Gln Glu
170                 175                 180                 185
```

```
CGT ATT TAC GGT GAT CAA TAC TAC AGT TTC GTC GAT CAA TTT GTA GAA      869
Arg Ile Tyr Gly Asp Gln Tyr Tyr Ser Phe Val Asp Gln Phe Val Glu
                190                 195                 200

ACT GCA GAA TCA ATT TTC CCT AAA TTG TAC CTT CAC TGG GAA GAT TTC      917
Thr Ala Glu Ser Ile Phe Pro Lys Leu Tyr Leu His Trp Glu Asp Phe
            205                 210                 215

GGA CGT TCA AAT GCT GCA ACA ATT TTA AAT AAC TAC AAA ACA AAA ATC      965
Gly Arg Ser Asn Ala Ala Thr Ile Leu Asn Asn Tyr Lys Thr Lys Ile
        220                 225                 230

CCA ACA TTT AAT GAT GAC ATT CAA GGA ACT GGT ATT GTT GTT TTA GGT     1013
Pro Thr Phe Asn Asp Asp Ile Gln Gly Thr Gly Ile Val Val Leu Gly
    235                 240                 245

GGT ATT TTC GGA TCA CTT GAC ATT ACA GGT GAA AAA TTA ACT GAT CAA     1061
Gly Ile Phe Gly Ser Leu Asp Ile Thr Gly Glu Lys Leu Thr Asp Gln
250                 255                 260                 265

GTA TAT CTT TGC TAT GGT GGT GGT TCA GCC GGT GCA GGG ATT GCT GGT     1109
Val Tyr Leu Cys Tyr Gly Gly Gly Ser Ala Gly Ala Gly Ile Ala Gly
                270                 275                 280

CGT GTT CAT GCT GAA ATG GTT AGT GAA GGT CTT TCT GAA GAA GAA GCT     1157
Arg Val His Ala Glu Met Val Ser Glu Gly Leu Ser Glu Glu Glu Ala
            285                 290                 295

TAC AAA CAT TTC TTC ATG ATT GAT CAA CAA GGT TTA CTT TTT GAT GAT     1205
Tyr Lys His Phe Phe Met Ile Asp Gln Gln Gly Leu Leu Phe Asp Asp
        300                 305                 310

ATG GAA GAC CTT ACA CCA GCT CAA AAA CCA TTT GCT AAA AAA CGT GCT     1253
Met Glu Asp Leu Thr Pro Ala Gln Lys Pro Phe Ala Lys Lys Arg Ala
    315                 320                 325

GAT TAT AAA GAT GCT GGA GAT ATG ACT GAC CTT CTT AAC GTT GTT AAG     1301
Asp Tyr Lys Asp Ala Gly Asp Met Thr Asp Leu Leu Asn Val Val Lys
330                 335                 340                 345

ACA GTA AAA CCA ACT ATT TTA GTA GGA ACT TCA ACT AAT CCA GGT GCC     1349
Thr Val Lys Pro Thr Ile Leu Val Gly Thr Ser Thr Asn Pro Gly Ala
                350                 355                 360

TTT ACA AAA GAA GTT GTT GAA GCA ATG TGT GCT AAT ACA GAA CGC CCA     1397
Phe Thr Lys Glu Val Val Glu Ala Met Cys Ala Asn Thr Glu Arg Pro
            365                 370                 375

GTA ATC TTC CCT ATC TCA AAT CCA ACT AAA AAA ATG GAA ACT ACA GCT     1445
Val Ile Phe Pro Ile Ser Asn Pro Thr Lys Lys Met Glu Thr Thr Ala
        380                 385                 390

GAA CAA GTT ATT GAG TGG TCT GAT GGA AAA GCT TTT GTC GCT ACT GGT     1493
Glu Gln Val Ile Glu Trp Ser Asp Gly Lys Ala Phe Val Ala Thr Gly
    395                 400                 405

GTT CCT TCA GGA ACA ATC AGC TAC AAA GGT GTT GAT TAT CAA ATT GGT     1541
Val Pro Ser Gly Thr Ile Ser Tyr Lys Gly Val Asp Tyr Gln Ile Gly
410                 415                 420                 425

CAA GCA AAT AAC TCA CTT ATC TAC CCA GGT TTG GGC TTA GGA ATG TTG     1589
Gln Ala Asn Asn Ser Leu Ile Tyr Pro Gly Leu Gly Leu Gly Met Leu
                430                 435                 440

GCA TCT GAA GCA AAA CTT TTG ACA GAT GAA ATG ATC GGT GCA GCT GCA     1637
Ala Ser Glu Ala Lys Leu Leu Thr Asp Glu Met Ile Gly Ala Ala Ala
            445                 450                 455

CAT TCA TTG AGC GGT TTA GTA GAT CCA GGT AAA CCA GGT GCT CCT GTT     1685
His Ser Leu Ser Gly Leu Val Asp Pro Gly Lys Pro Gly Ala Pro Val
        460                 465                 470

CTT CCT CCA TTT GAA TTT GTT GCT GAT GTA TCA ATT AAA GTT GCA GAA     1733
Leu Pro Pro Phe Glu Phe Val Ala Asp Val Ser Ile Lys Val Ala Glu
    475                 480                 485

GCA GTT GCT AAG AAA GCT CAA GAA CAA GGT CTT ACT GAA TCT AAA GAA     1781
Ala Val Ala Lys Lys Ala Gln Glu Gln Gly Leu Thr Glu Ser Lys Glu
```

```
                490                495                500                505
ACT GAT ATG GCT AAA GCA GTT CGT GAT CTT AAA TGG TAT CCA GAG TAC          1829
Thr Asp Met Ala Lys Ala Val Arg Asp Leu Lys Trp Tyr Pro Glu Tyr
            510                515                520

TAA GGGAATATC TTAAATGAAA AAACTTAAAG AAACGAAAAT ATCGGGAATT                1882
 *

AGTCTTCCCT TATATGCCTT TTTCGTAGCT GTCATCATAG TTGTA                        1927
```

(2) INFORMATION FOR SEQ ID NO:4:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Glu Arg Gln Glu Leu Gly Leu Ile Gly Leu Leu Pro Pro Thr
 1               5                  10                  15

Val Gln Thr Ile Glu Glu Gln Ala Glu Gln Thr Tyr Glu Gln Tyr Leu
            20                  25                  30

Thr Lys Pro Ser Asp Leu Glu Lys Arg His Phe Leu Met Glu Ile Phe
        35                  40                  45

Asn Thr Asn Arg Thr Leu Phe Tyr Tyr Leu Phe Asn Lys His Ile Val
 50                  55                  60

Glu Phe Asn Pro Val Val Tyr Asp Pro Thr Ile Ala Asp Thr Ile Glu
 65                  70                  75                  80

Asn Tyr Ser His Leu Phe Val Asp Pro Gln Tyr Ala Ala Tyr Leu Asp
                85                  90                  95

Ile Asn His Pro Glu Asn Ile Thr Glu Thr Leu Lys Asn Ala Ala Gly
            100                 105                 110

Asp Arg Glu Ile Arg Leu Ile Val Thr Asp Ala Glu Gly Ile Leu
        115                 120                 125

Gly Ile Gly Asp Trp Gly Thr Gln Gly Val Asp Ile Ser Val Gly Lys
130                 135                 140

Leu Met Ile Tyr Thr Ala Ala Ala Gly Ile Asp Pro Ala Ser Val Leu
145                 150                 155                 160

Pro Val Val Ile Asp Ala Gly Thr Asn Arg Lys Glu Leu Leu Glu Asp
                165                 170                 175

His Leu Tyr Leu Gly Asn His Gln Glu Arg Ile Tyr Gly Asp Gln Tyr
            180                 185                 190

Tyr Ser Phe Val Asp Gln Phe Val Glu Thr Ala Glu Ser Ile Phe Pro
        195                 200                 205

Lys Leu Tyr Leu His Trp Glu Asp Phe Gly Arg Ser Asn Ala Ala Thr
210                 215                 220

Ile Leu Asn Asn Tyr Lys Thr Lys Ile Pro Thr Phe Asn Asp Asp Ile
225                 230                 235                 240

Gln Gly Thr Gly Ile Val Val Leu Gly Gly Ile Phe Gly Ser Leu Asp
                245                 250                 255

Ile Thr Gly Glu Lys Leu Thr Asp Gln Val Tyr Leu Cys Tyr Gly Gly
            260                 265                 270

Gly Ser Ala Gly Ala Gly Ile Ala Gly Arg Val His Ala Glu Met Val
        275                 280                 285

Ser Glu Gly Leu Ser Glu Glu Ala Tyr Lys His Phe Phe Met Ile
290                 295                 300
```

```
Asp Gln Gln Gly Leu Leu Phe Asp Asp Met Glu Asp Leu Thr Pro Ala
305                 310                 315                 320

Gln Lys Pro Phe Ala Lys Lys Arg Ala Asp Tyr Lys Asp Ala Gly Asp
            325                 330                 335

Met Thr Asp Leu Leu Asn Val Val Lys Thr Val Lys Pro Thr Ile Leu
            340                 345                 350

Val Gly Thr Ser Thr Asn Pro Gly Ala Phe Thr Lys Glu Val Val Glu
            355                 360                 365

Ala Met Cys Ala Asn Thr Glu Arg Pro Val Ile Phe Pro Ile Ser Asn
370                 375                 380

Pro Thr Lys Lys Met Glu Thr Thr Ala Glu Gln Val Ile Glu Trp Ser
385                 390                 395                 400

Asp Gly Lys Ala Phe Val Ala Thr Gly Val Pro Ser Gly Thr Ile Ser
            405                 410                 415

Tyr Lys Gly Val Asp Tyr Gln Ile Gly Gln Ala Asn Asn Ser Leu Ile
            420                 425                 430

Tyr Pro Gly Leu Gly Leu Gly Met Leu Ala Ser Glu Ala Lys Leu Leu
            435                 440                 445

Thr Asp Glu Met Ile Gly Ala Ala Ala His Ser Leu Ser Gly Leu Val
450                 455                 460

Asp Pro Gly Lys Pro Gly Ala Pro Val Leu Pro Pro Phe Glu Phe Val
465                 470                 475                 480

Ala Asp Val Ser Ile Lys Val Ala Glu Ala Val Ala Lys Lys Ala Gln
            485                 490                 495

Glu Gln Gly Leu Thr Glu Ser Lys Glu Thr Asp Met Ala Lys Ala Val
            500                 505                 510

Arg Asp Leu Lys Trp Tyr Pro Glu Tyr
            515                 520

(2) INFORMATION FOR SEQ ID NO:5:

(i) SEQUENCE CHARACTERISTICS:
        (A) LENGTH: 2686 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Lactococcus lactis (vii) IMMEDIATE SOURCE:
        (B) CLONE: mleS (ix) FEATURE:
        (A) NAME/KEY: CDS
        (B) LOCATION: 467..2089

(xi) SEQUENCE DESCRIPTION: SEQ ID NO:5:

CTTTTGTTGA AAAAATTTCT AATCAAATTA TTAACCTAAA AGATACATAA ATTTAAAAAA      60

TAAAAGTAGA GTGATTTTAC TCTACTTTTT TAGAATACTT TTATATAATA GGAAATATGA     120

ATAAAGCAAA GCGCACAATT TTGGTTTTAT TTAAAAAAAT GGATACTTTA GATACACAAC     180

CACCATTGAC AAAAAATCTT AATCTTAAAT TGTTTGAAAC CCTGATAAAT TAGGAATAGT     240

AATAGGAGAA GAACAGTTTA TCATTTAATA GTTATAAGCT AATTTTTACT ACCATTTCTT     300

TGATTAATAT CATCTATTTT TATATAGAGA CTTTTAAATA AACATTGACA TTATTTATGC     360

GTTATAAATA AAATTTATCA ACACTAAGGA ATTTGACTAT AACGATAAAA GAAGTTTATA     420
```

```
GTAATAAAGT AATAACATTA ATTATAATTT TTATGGAGGT TGTACG ATG CGT GCA            475
                                                   Met Arg Ala
                                                     1

CAT GAA ATT TTA AAC AAT CCT TTT TTA AAT AAA GGA ACA GCT TTT ACT           523
His Glu Ile Leu Asn Asn Pro Phe Leu Asn Lys Gly Thr Ala Phe Thr
      5              10                  15

ATG AAA GAA CGT CAA GAA TTG GGG TTG ATT GGT CTT CTT CCA CCA ACT           571
Met Lys Glu Arg Gln Glu Leu Gly Leu Ile Gly Leu Leu Pro Pro Thr
 20              25                  30                  35

GTT CAA ACA ATT GAG GAA CAA GCT GTA CAA ACT TAC GAA CAA TAT TTG           619
Val Gln Thr Ile Glu Glu Gln Ala Val Gln Thr Tyr Glu Gln Tyr Leu
             40                  45                  50

ACA AAA CCA TCT GAT TTA GAA AAA CGT CAT TTC TTG ATG GAA ATT TTT           667
Thr Lys Pro Ser Asp Leu Glu Lys Arg His Phe Leu Met Glu Ile Phe
             55                  60                  65

AAT ACA AAC CGT ACT TTG TTT TAC TAC TTA TTC AAC AAA CAT ATT GTA           715
Asn Thr Asn Arg Thr Leu Phe Tyr Tyr Leu Phe Asn Lys His Ile Val
         70                  75                  80

GAA TTT AAT CCA GTT GTT TAT GAT CCA ACA ATT GCT GAT ACA ATT GAA           763
Glu Phe Asn Pro Val Val Tyr Asp Pro Thr Ile Ala Asp Thr Ile Glu
     85                  90                  95

AAC TAC AGT CAT TTG TTC GTA GAT CCA CAA TAT GCT GCT TAT CTT GAT           811
Asn Tyr Ser His Leu Phe Val Asp Pro Gln Tyr Ala Ala Tyr Leu Asp
100             105                 110                 115

ATT AAC CAC CCT GAA AAC ATT ACT GAA ACA TTG AAA AGT GCA GCA GGT           859
Ile Asn His Pro Glu Asn Ile Thr Glu Thr Leu Lys Ser Ala Ala Gly
             120                 125                 130

GAC AGA GAA ATT CGT CTT ATT GTT GTA ACT GAT GCT GAA GGA ATC CTT           907
Asp Arg Glu Ile Arg Leu Ile Val Val Thr Asp Ala Glu Gly Ile Leu
             135                 140                 145

GGT ATT GGA GAC TGG GGA ACT CAA GGT GTT GAT ATC TCA GTT GGT AAA           955
Gly Ile Gly Asp Trp Gly Thr Gln Gly Val Asp Ile Ser Val Gly Lys
            150                 155                 160

TTA ATG ATT TAT ACA GCC GCA GCA GGT ATT GAT CCA GCG TCT GTA CTT          1003
Leu Met Ile Tyr Thr Ala Ala Ala Gly Ile Asp Pro Ala Ser Val Leu
        165                 170                 175

CCA GTT GTT ATT GAT GCA GGA ACA AAT AGA AAA GAA CTT TTA GAA GAT          1051
Pro Val Val Ile Asp Ala Gly Thr Asn Arg Lys Glu Leu Leu Glu Asp
180                 185                 190                 195

CAT TTG TAT CTT GGA AAT CAT CAA GAA CGT ATT TAC GGT GAT CAA TAC          1099
His Leu Tyr Leu Gly Asn His Gln Glu Arg Ile Tyr Gly Asp Gln Tyr
                200                 205                 210

TAC AGT TTC GTC GAT CAA TTT GTA GAA ACT GCA GAA TCA ATT TTC CCT          1147
Tyr Ser Phe Val Asp Gln Phe Val Glu Thr Ala Glu Ser Ile Phe Pro
            215                 220                 225

AAA TTG TAC CTT CAC TGG GAA GAT TTC GGA CGT TCA AAT GCT GCA ACA          1195
Lys Leu Tyr Leu His Trp Glu Asp Phe Gly Arg Ser Asn Ala Ala Thr
        230                 235                 240

ATT TTA AAT AAC TAC AAA ACA AAA ATC CCA ACA TTT AAT GAT GAC ATT          1243
Ile Leu Asn Asn Tyr Lys Thr Lys Ile Pro Thr Phe Asn Asp Asp Ile
    245                 250                 255

CAA GGA ACT GGT ATT GTT GTT TTA GGT GGT ATT TTC GGA TCA CTT GAC          1291
Gln Gly Thr Gly Ile Val Val Leu Gly Gly Ile Phe Gly Ser Leu Asp
260                 265                 270                 275

ATT ACA GGT GAA AAA TTA ACT GAT CAA GTA TAT CTT TGC TAT GGT GGT          1339
Ile Thr Gly Glu Lys Leu Thr Asp Gln Val Tyr Leu Cys Tyr Gly Gly
                280                 285                 290

GGT TCA GCC GGT GCA GGG ATT GCT GGT CGT GTT CAT GCT GAA ATG GTT          1387
Gly Ser Ala Gly Ala Gly Ile Ala Gly Arg Val His Ala Glu Met Val
```

```
                  295                 300                 305
AGT GAA GGT CTT TCT GAA GAA GAA GCT TAC AAA CAT TTC TTC ATG ATT      1435
Ser Glu Gly Leu Ser Glu Glu Glu Ala Tyr Lys His Phe Phe Met Ile
            310                 315                 320

GAT CAA CAA GGT TTA CTT TTT GAT GAT ATG GAA GAC CTT ACA CCA GCT      1483
Asp Gln Gln Gly Leu Leu Phe Asp Asp Met Glu Asp Leu Thr Pro Ala
        325                 330                 335

CAA AAA CCA TTT GCT AAA AAA CGT GCT GAT TAT AAA GAT GCT GGA GAT      1531
Gln Lys Pro Phe Ala Lys Lys Arg Ala Asp Tyr Lys Asp Ala Gly Asp
340                 345                 350                 355

ATG ACT GAC CTT CTT AAC GTT GTT AAG ACA GTA AAA CCA ACT ATT TTA      1579
Met Thr Asp Leu Leu Asn Val Val Lys Thr Val Lys Pro Thr Ile Leu
                360                 365                 370

GTA GGA ACT TCA ACT AAT CCA GGT GCC TTT ACA AAA GAA GTT GTT GAA      1627
Val Gly Thr Ser Thr Asn Pro Gly Ala Phe Thr Lys Glu Val Val Glu
            375                 380                 385

GCA ATG TGT GCT AAT ACA GAA CGC CCA GTA ATC TTC CCT ATC TCA AAT      1675
Ala Met Cys Ala Asn Thr Glu Arg Pro Val Ile Phe Pro Ile Ser Asn
        390                 395                 400

CCA ACT AAA AAA ATG GAA ACT ACA GCT GAA CAA GTT ATT GAG TGG TCT      1723
Pro Thr Lys Lys Met Glu Thr Thr Ala Glu Gln Val Ile Glu Trp Ser
405                 410                 415

GAT GGA AAA GCT TTT GTC GCT ACT GGT GTT CCT TCA GGA ACA ATC AGC      1771
Asp Gly Lys Ala Phe Val Ala Thr Gly Val Pro Ser Gly Thr Ile Ser
420                 425                 430                 435

TAC AAA GGT GTT GAT TAT CAA ATT GGT CAA GCA AAT AAC TCA CTT ATC      1819
Tyr Lys Gly Val Asp Tyr Gln Ile Gly Gln Ala Asn Asn Ser Leu Ile
                440                 445                 450

CAC CCA GGT TTG GGC TTA GGA ATG TTG GCA TCT GAA GCA AAA CTT TTG      1867
His Pro Gly Leu Gly Leu Gly Met Leu Ala Ser Glu Ala Lys Leu Leu
            455                 460                 465

ACA GAT GAA ATG ATC GGT GCA GCT GCA CAT TCA TTG AGC GGT TTA GTA      1915
Thr Asp Glu Met Ile Gly Ala Ala Ala His Ser Leu Ser Gly Leu Val
        470                 475                 480

GAT CCA GGT AAA CCA GGT GCT CCT GTT CTT CCT CCA TTT GAA TTT GTT      1963
Asp Pro Gly Lys Pro Gly Ala Pro Val Leu Pro Pro Phe Glu Phe Val
    485                 490                 495

GCT GAT GTA TCA ATT AAA GTT GCA GAA GCA GTT GCT AAG AAA GCT CAA      2011
Ala Asp Val Ser Ile Lys Val Ala Glu Ala Val Ala Lys Lys Ala Gln
500                 505                 510                 515

GAA CAA GGT CTT ACT GAA TCT AAA GAA ACT GAT ATG GCT AAA GCA GTT      2059
Glu Gln Gly Leu Thr Glu Ser Lys Glu Thr Asp Met Ala Lys Ala Val
                520                 525                 530

CGT GAT CTT AAA TGG TAT CCA GAG TAC TAA GGGGAATATC TTAAATGAAA        2109
Arg Asp Leu Lys Trp Tyr Pro Glu Tyr  *
            535                 540

AAACTTAAAG AAACGAAAAT ATCGGGAATT AGTCTTCCCT TATATGCCTT TTTCGTAGCT    2169

GTCATCATAG TTGTAACACT ATTAGGAAAA CTTCCACTTG ATATGGTAGG GTTAACTCTC    2229

CTACTTGTAA CATTAGGCCA CCTATTATAC TTCATAGGAG AAAAATTCCC TATTATGAAT    2289

TCATACTTAG GTGGGGATC TGTTTTCACT TTAATTGGTG CTACTCTATT ATCTTTCTTC     2349

CACATTGTTC CTTCAAATGT TATTGGAGCA GTTTCCAATT TTATGGGTGG AAAATTTGGA    2409

TTTCTTGATT TTTATATAGC TGCACTTATC TGTGGATCTA TTTTAGGAAT GAACAGAAAT    2469

CTTTTGGTTA AAGCTTCCAA GAAATTTATT CCGATTGCTT TAATCACTAT GGTTATTGGT    2529

TTCTTCTCAG TAGGTCTTGT AGGAATGCTT ATTGGTAATG GATTTGCTGA TTCTGTAATG    2589

TATGTTTCTA TGCCAATGAT GTCAGGTGGT ATGGGAGCCG GAATTACTCC ACTCTCTCAA    2649
```

ATCTATGCAG CCGGATTGGC TCATGGAAAC CAAGCAG                                    2686

(2) INFORMATION FOR SEQ ID NO:6:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Ala His Glu Ile Leu Asn Asn Pro Phe Leu Asn Lys Gly Thr
  1               5                  10                  15

Ala Phe Thr Met Lys Glu Arg Gln Glu Leu Gly Leu Ile Gly Leu Leu
             20                  25                  30

Pro Pro Thr Val Gln Thr Ile Glu Glu Gln Ala Val Gln Thr Tyr Glu
         35                  40                  45

Gln Tyr Leu Thr Lys Pro Ser Asp Leu Glu Lys Arg His Phe Leu Met
     50                  55                  60

Glu Ile Phe Asn Thr Asn Arg Thr Leu Phe Tyr Tyr Leu Phe Asn Lys
 65                  70                  75                  80

His Ile Val Glu Phe Asn Pro Val Val Tyr Asp Pro Thr Ile Ala Asp
                 85                  90                  95

Thr Ile Glu Asn Tyr Ser His Leu Phe Val Asp Pro Gln Tyr Ala Ala
            100                 105                 110

Tyr Leu Asp Ile Asn His Pro Glu Asn Ile Thr Glu Thr Leu Lys Ser
        115                 120                 125

Ala Ala Gly Asp Arg Glu Ile Arg Leu Ile Val Val Thr Asp Ala Glu
    130                 135                 140

Gly Ile Leu Gly Ile Gly Asp Trp Gly Thr Gln Gly Val Asp Ile Ser
145                 150                 155                 160

Val Gly Lys Leu Met Ile Tyr Thr Ala Ala Gly Ile Asp Pro Ala
                165                 170                 175

Ser Val Leu Pro Val Val Ile Asp Ala Gly Thr Asn Arg Lys Glu Leu
                180                 185                 190

Leu Glu Asp His Leu Tyr Leu Gly Asn His Gln Glu Arg Ile Tyr Gly
            195                 200                 205

Asp Gln Tyr Tyr Ser Phe Val Asp Gln Phe Val Glu Thr Ala Glu Ser
    210                 215                 220

Ile Phe Pro Lys Leu Tyr Leu His Trp Glu Asp Phe Gly Arg Ser Asn
225                 230                 235                 240

Ala Ala Thr Ile Leu Asn Asn Tyr Lys Thr Lys Ile Pro Thr Phe Asn
                245                 250                 255

Asp Asp Ile Gln Gly Thr Gly Ile Val Val Leu Gly Gly Ile Phe Gly
            260                 265                 270

Ser Leu Asp Ile Thr Gly Glu Lys Leu Thr Asp Gln Val Tyr Leu Cys
        275                 280                 285

Tyr Gly Gly Gly Ser Ala Gly Ala Gly Ile Ala Gly Arg Val His Ala
    290                 295                 300

Glu Met Val Ser Glu Gly Leu Ser Glu Glu Ala Tyr Lys His Phe
305                 310                 315                 320

Phe Met Ile Asp Gln Gln Gly Leu Leu Phe Asp Asp Met Glu Asp Leu
                325                 330                 335

Thr Pro Ala Gln Lys Pro Phe Ala Lys Lys Arg Ala Asp Tyr Lys Asp
```

```
                    340             345             350
Ala Gly Asp Met Thr Asp Leu Leu Asn Val Val Lys Thr Val Lys Pro
            355                 360                 365

Thr Ile Leu Val Gly Thr Ser Thr Asn Pro Gly Ala Phe Thr Lys Glu
    370                 375                 380

Val Val Glu Ala Met Cys Ala Asn Thr Glu Arg Pro Val Ile Phe Pro
385                 390                 395                 400

Ile Ser Asn Pro Thr Lys Lys Met Glu Thr Thr Ala Glu Gln Val Ile
                405                 410                 415

Glu Trp Ser Asp Gly Lys Ala Phe Val Ala Thr Gly Val Pro Ser Gly
            420                 425                 430

Thr Ile Ser Tyr Lys Gly Val Asp Tyr Gln Ile Gly Gln Ala Asn Asn
            435                 440                 445

Ser Leu Ile His Pro Gly Leu Gly Leu Gly Met Leu Ala Ser Glu Ala
    450                 455                 460

Lys Leu Leu Thr Asp Glu Met Ile Gly Ala Ala Ala His Ser Leu Ser
465                 470                 475                 480

Gly Leu Val Asp Pro Gly Lys Pro Gly Ala Pro Val Leu Pro Pro Phe
                485                 490                 495

Glu Phe Val Ala Asp Val Ser Ile Lys Val Ala Glu Ala Val Ala Lys
                500                 505                 510

Lys Ala Gln Glu Gln Gly Leu Thr Glu Ser Lys Glu Thr Asp Met Ala
            515                 520                 525

Lys Ala Val Arg Asp Leu Lys Trp Tyr Pro Glu Tyr
            530                 535                 540

(2) INFORMATION FOR SEQ ID NO:7:

(i) SEQUENCE CHARACTERISTICS:
        (A) LENGTH: 2422 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Schizosaccharomyces pombe (vii) IMMEDIATE SOURCE:
        (B) CLONE: mae2

(ix) FEATURE:
        (A) NAME/KEY: CDS
        (B) LOCATION: 1..1698

(xi) SEQUENCE DESCRIPTION: SEQ ID NO:7:

ATG CCT GCA GGA ACC AAA GAA CAA ATC GAG TGT CCT TTA AAA GGA GTA     48
Met Pro Ala Gly Thr Lys Glu Gln Ile Glu Cys Pro Leu Lys Gly Val
1               5                   10                  15

ACT TTG TTA AAC TCT CCT CGC TAC AAT AAG GAC ACT GCT TTT ACA CCT     96
Thr Leu Leu Asn Ser Pro Arg Tyr Asn Lys Asp Thr Ala Phe Thr Pro
                20                  25                  30

GAG GAG CGT CAA AAA TTT GAG ATT TCA TCA CGT CTT CCC CCC ATT GTT    144
Glu Glu Arg Gln Lys Phe Glu Ile Ser Ser Arg Leu Pro Pro Ile Val
            35                  40                  45

GAA ACT TTG CAA CAA CAA GTG GAT CGC TGT TAT GAC CAG TAC AAA GCA    192
Glu Thr Leu Gln Gln Gln Val Asp Arg Cys Tyr Asp Gln Tyr Lys Ala
        50                  55                  60

ATC GGT GAT GAG CCC TTA CAG AAG AAT TTG TAT CTT TCT CAA TTA AGC    240
Ile Gly Asp Glu Pro Leu Gln Lys Asn Leu Tyr Leu Ser Gln Leu Ser
```

```
                65                    70                    75                    80
GTC ACC AAC CAA ACT CTG TTT TAC GCA CTC ATC AGC CAA CAT TTG ATC              288
Val Thr Asn Gln Thr Leu Phe Tyr Ala Leu Ile Ser Gln His Leu Ile
                    85                    90                    95

GAA ATG ATT CCT ATC ATC TAT ACA CCT ACC GAA GGC GAT GCC ATC AAG              336
Glu Met Ile Pro Ile Ile Tyr Thr Pro Thr Glu Gly Asp Ala Ile Lys
                100                   105                   110

CAG TTT TCC GAT ATA TAT CGT TAT CCT GAG GGT TGT TAT TTG GAT ATT              384
Gln Phe Ser Asp Ile Tyr Arg Tyr Pro Glu Gly Cys Tyr Leu Asp Ile
                115                   120                   125

GAT CAT AAC GAT TTG TCT TAT ATC AAG CAA CAG CTT TCC GAG TTT GGA              432
Asp His Asn Asp Leu Ser Tyr Ile Lys Gln Gln Leu Ser Glu Phe Gly
        130                   135                   140

AAA TCC GAT AGT GTC GAA TAC ATT ATC ATT ACC GAT TCT GAA GGT ATT              480
Lys Ser Asp Ser Val Glu Tyr Ile Ile Ile Thr Asp Ser Glu Gly Ile
145                   150                   155                   160

TTG GGT ATC GGC GAT CAA GGT GTT GGT GGT GTC TTA ATT TCA GTT GCC              528
Leu Gly Ile Gly Asp Gln Gly Val Gly Gly Val Leu Ile Ser Val Ala
                165                   170                   175

AAG GGA CAT TTA ATG ACT TTA TGC GCG GGT TTA GAC CCT AAT CGA TTC              576
Lys Gly His Leu Met Thr Leu Cys Ala Gly Leu Asp Pro Asn Arg Phe
                180                   185                   190

TTG CCC ATT GTT CTC GAT GTT GGC ACC AAC AAT GAA ACC CAT CGT AAA              624
Leu Pro Ile Val Leu Asp Val Gly Thr Asn Asn Glu Thr His Arg Lys
                195                   200                   205

AAT CAT CAA TAC ATG GGT TTG AGA AAG GAT CGT GTT CGT GGT GAA CAG              672
Asn His Gln Tyr Met Gly Leu Arg Lys Asp Arg Val Arg Gly Glu Gln
        210                   215                   220

TAT GAC AGC TTT TTG GAC AAT GTT ATA AAG GCC ATT CGT GAA GTC TTT              720
Tyr Asp Ser Phe Leu Asp Asn Val Ile Lys Ala Ile Arg Glu Val Phe
225                   230                   235                   240

CCT GAG GCC TTT ATT CAT TTT GAG GAT TTT GGT CTT GCC AAC GCC AAG              768
Pro Glu Ala Phe Ile His Phe Glu Asp Phe Gly Leu Ala Asn Ala Lys
                245                   250                   255

CGC ATT TTA GAC CAC TAT CGT CCT GAC ATT GCC TGC TTT AAC GAT GAT              816
Arg Ile Leu Asp His Tyr Arg Pro Asp Ile Ala Cys Phe Asn Asp Asp
                260                   265                   270

ATC CAG GGA ACC GGT GCC GTA GCA TTG GCC GCC ATT ATT GGC GCC CTT              864
Ile Gln Gly Thr Gly Ala Val Ala Leu Ala Ala Ile Ile Gly Ala Leu
                275                   280                   285

CAC GTT ACG AAA TCT CCC TTA ACC GAG CAG CGC ATC ATG ATC TTT GGT              912
His Val Thr Lys Ser Pro Leu Thr Glu Gln Arg Ile Met Ile Phe Gly
        290                   295                   300

GCA GGT ACT GCT GGT GTT GGT ATC GCC AAC CAA ATT GTT GCC GGT ATG              960
Ala Gly Thr Ala Gly Val Gly Ile Ala Asn Gln Ile Val Ala Gly Met
305                   310                   315                   320

GTG ACA GAT GGC CTT TCA TTA GAT AAG GCT AGA GGT AAT CTT TTC ATG             1008
Val Thr Asp Gly Leu Ser Leu Asp Lys Ala Arg Gly Asn Leu Phe Met
                325                   330                   335

ATT GAT CGT TGC GGT TTG CTT TTG GAG AGA CAT GCT AAG ATT GCT ACT             1056
Ile Asp Arg Cys Gly Leu Leu Leu Glu Arg His Ala Lys Ile Ala Thr
                340                   345                   350

GAT GGA CAA AAG CCA TTT TTG AAG AAG GAC TCT GAC TTT AAG GAA GTC             1104
Asp Gly Gln Lys Pro Phe Leu Lys Lys Asp Ser Asp Phe Lys Glu Val
                355                   360                   365

CCT TCT GGA GAC ATT AAT TTA GAG AGT GCT ATT GCA CTC GTC AAG CCC             1152
Pro Ser Gly Asp Ile Asn Leu Glu Ser Ala Ile Ala Leu Val Lys Pro
        370                   375                   380

ACC ATT CTT TTG GGA TGT TCC GGT CAA CCG GGT AAA TTT ACA GAG AAA             1200
```

```
Thr Ile Leu Leu Gly Cys Ser Gly Gln Pro Gly Lys Phe Thr Glu Lys
385                 390                 395                 400

GCC ATT CGT GAA ATG AGC AAG CAC GTC GAG CGC CCC ATC ATT TTC CCA      1248
Ala Ile Arg Glu Met Ser Lys His Val Glu Arg Pro Ile Ile Phe Pro
                405                 410                 415

ATC TCT AAT CCC ACT ACT CTT ATG GAA GCG AAG CCC GAT CAA ATT GAC      1296
Ile Ser Asn Pro Thr Thr Leu Met Glu Ala Lys Pro Asp Gln Ile Asp
            420                 425                 430

AAA TGG TCA GAT GGA AAG GCT TTG ATA GCC ACT GGT TCC CCA CTT CCT      1344
Lys Trp Ser Asp Gly Lys Ala Leu Ile Ala Thr Gly Ser Pro Leu Pro
        435                 440                 445

CCT CTC AAT CGC AAT GGT AAA AAA TAC GTG ATT TCC CAA TGC AAC AAT      1392
Pro Leu Asn Arg Asn Gly Lys Lys Tyr Val Ile Ser Gln Cys Asn Asn
450                 455                 460

GCC CTC CTT TAC CCT GCT CTT GGT GTT GCA TGT GTG TTA TCC CGT TGC      1440
Ala Leu Leu Tyr Pro Ala Leu Gly Val Ala Cys Val Leu Ser Arg Cys
465                 470                 475                 480

AAG TTA TTG AGT GAT GGT ATG CTG AAA GCA GCT TCC GAT GCT TTG GCC      1488
Lys Leu Leu Ser Asp Gly Met Leu Lys Ala Ala Ser Asp Ala Leu Ala
                485                 490                 495

ACT GTT CCC AGA TCT TTA TTT GCT GCT GAT GAA GCC CTC TTG CCA GAT      1536
Thr Val Pro Arg Ser Leu Phe Ala Ala Asp Glu Ala Leu Leu Pro Asp
            500                 505                 510

TTG AAC AAT GCT CGC GAA ATT TCT CGT CAC ATT GTT TTT GCA GTC TTG      1584
Leu Asn Asn Ala Arg Glu Ile Ser Arg His Ile Val Phe Ala Val Leu
        515                 520                 525

AAG CAA GCT GTT TCT GAG GGA ATG AGC ACT GTG GAT TTA CCC AAA GAT      1632
Lys Gln Ala Val Ser Glu Gly Met Ser Thr Val Asp Leu Pro Lys Asp
530                 535                 540

GAT GCT AAA TTG AAG GAA TGG ATT ATT GAA CGT GAA TGG AAT CCC GAA      1680
Asp Ala Lys Leu Lys Glu Trp Ile Ile Glu Arg Glu Trp Asn Pro Glu
545                 550                 555                 560

TAC AAG CCT TTT GTA TAA AGCCTTTTAT TTTATTTTTT TTTGAAACCT             1728
Tyr Lys Pro Phe Val  *
                565

GCTTTTTGGT CTGCTTGTAT TTAAAGATAT TCATGTAAAT AATTTTTTGA AAGATGAATT    1788

TACAATAAGT TGCTAAAAAG AAAATTCCCG TTTTATTCAA ATGCTCATAT TTGAATATTA    1848

GAAACATTAT GTACATATTT AGGCATCTTC CATTAAGAAT GATTAATGCG TAGAAAGATA    1908

ATCAATTATT ATTGCTTTTT TCTCCTATTG TTATTCATCA ACTATATACA TTAAAAAGAT    1968

TGGAGTATAG CAGAGGTAGA ATTTCTTTAC TCTGAAAAGT AAATCGAAAT AAATGGTATA    2028

TGATTCAGTC TGAAATAAAT TGAGCACGAG TATTCAAACC GTAAACCGTT ATGTATTGAA    2088

TGAACCATTT GATTTAATAA AGGTTATAAT TTTACGAATT TATAATGGGT AGTTATATAG    2148

AAACACCAAG TTAACTTTAT AATCAGATTA ATCTGAATAA TAAATTAAAA AGGGAAAGAG    2208

AAATCTGTAT ATGGATGAAA CAAACAAATA GTAAATCGCA TTTGACACCT ACAAAATGTG    2268

TGTGAATATA TACATACAAG GAGGGCCTGT AAATAGAACT TTGTATTCCC AAGGGATTTA    2328

GTGAACACCC TTAAAATCGT TATTACTAAA TTTCGTAGAT CAGTTTCTTG AAGGTAAACT    2388

CATCACCCCC AAGTCTGGCT ATGCAGAAAT CCCC                                2422

(2) INFORMATION FOR SEQ ID NO:8:

(i) SEQUENCE CHARACTERISTICS:
        (A) LENGTH: 565 amino acids
        (B) TYPE: amino acid
        (D) TOPOLOGY: linear
```

(ii) MOLECULE TYPE: protein (xi) SEQUENCE DESCRIPTION: SEQ ID NO:8:

```
Met Pro Ala Gly Thr Lys Glu Gln Ile Glu Cys Pro Leu Lys Gly Val
 1               5                  10                  15

Thr Leu Leu Asn Ser Pro Arg Tyr Asn Lys Asp Thr Ala Phe Thr Pro
             20                  25                  30

Glu Glu Arg Gln Lys Phe Glu Ile Ser Ser Arg Leu Pro Pro Ile Val
         35                  40                  45

Glu Thr Leu Gln Gln Gln Val Asp Arg Cys Tyr Asp Gln Tyr Lys Ala
     50                  55                  60

Ile Gly Asp Glu Pro Leu Gln Lys Asn Leu Tyr Leu Ser Gln Leu Ser
 65                  70                  75                  80

Val Thr Asn Gln Thr Leu Phe Tyr Ala Leu Ile Ser Gln His Leu Ile
                 85                  90                  95

Glu Met Ile Pro Ile Ile Tyr Thr Pro Thr Glu Gly Asp Ala Ile Lys
            100                 105                 110

Gln Phe Ser Asp Ile Tyr Arg Tyr Pro Glu Gly Cys Tyr Leu Asp Ile
        115                 120                 125

Asp His Asn Asp Leu Ser Tyr Ile Lys Gln Gln Leu Ser Glu Phe Gly
    130                 135                 140

Lys Ser Asp Ser Val Glu Tyr Ile Ile Ile Thr Asp Ser Glu Gly Ile
145                 150                 155                 160

Leu Gly Ile Gly Asp Gln Gly Val Gly Gly Val Leu Ile Ser Val Ala
                165                 170                 175

Lys Gly His Leu Met Thr Leu Cys Ala Gly Leu Asp Pro Asn Arg Phe
            180                 185                 190

Leu Pro Ile Val Leu Asp Val Gly Thr Asn Asn Glu Thr His Arg Lys
        195                 200                 205

Asn His Gln Tyr Met Gly Leu Arg Lys Asp Arg Val Arg Gly Glu Gln
    210                 215                 220

Tyr Asp Ser Phe Leu Asp Asn Val Ile Lys Ala Ile Arg Glu Val Phe
225                 230                 235                 240

Pro Glu Ala Phe Ile His Phe Glu Asp Phe Gly Leu Ala Asn Ala Lys
                245                 250                 255

Arg Ile Leu Asp His Tyr Arg Pro Asp Ile Ala Cys Phe Asn Asp Asp
            260                 265                 270

Ile Gln Gly Thr Gly Ala Val Ala Leu Ala Ala Ile Gly Ala Leu
        275                 280                 285

His Val Thr Lys Ser Pro Leu Thr Glu Gln Arg Ile Met Ile Phe Gly
    290                 295                 300

Ala Gly Thr Ala Gly Val Gly Ile Ala Asn Gln Ile Val Ala Gly Met
305                 310                 315                 320

Val Thr Asp Gly Leu Ser Leu Asp Lys Ala Arg Gly Asn Leu Phe Met
                325                 330                 335

Ile Asp Arg Cys Gly Leu Leu Leu Glu Arg His Ala Lys Ile Ala Thr
            340                 345                 350

Asp Gly Gln Lys Pro Phe Leu Lys Lys Asp Ser Asp Phe Lys Glu Val
        355                 360                 365

Pro Ser Gly Asp Ile Asn Leu Glu Ser Ala Ile Ala Leu Val Lys Pro
    370                 375                 380

Thr Ile Leu Leu Gly Cys Ser Gly Gln Pro Gly Lys Phe Thr Glu Lys
385                 390                 395                 400
```

-continued

```
Ala Ile Arg Glu Met Ser Lys His Val Glu Arg Pro Ile Ile Phe Pro
            405                 410                 415
Ile Ser Asn Pro Thr Thr Leu Met Glu Ala Lys Pro Asp Gln Ile Asp
            420                 425                 430
Lys Trp Ser Asp Gly Lys Ala Leu Ile Ala Thr Gly Ser Pro Leu Pro
            435                 440                 445
Pro Leu Asn Arg Asn Gly Lys Lys Tyr Val Ile Ser Gln Cys Asn Asn
        450                 455                 460
Ala Leu Leu Tyr Pro Ala Leu Gly Val Ala Cys Val Leu Ser Arg Cys
465                 470                 475                 480
Lys Leu Leu Ser Asp Gly Met Leu Lys Ala Ala Ser Asp Ala Leu Ala
                485                 490                 495
Thr Val Pro Arg Ser Leu Phe Ala Ala Asp Glu Ala Leu Leu Pro Asp
            500                 505                 510
Leu Asn Asn Ala Arg Glu Ile Ser Arg His Ile Val Phe Ala Val Leu
            515                 520                 525
Lys Gln Ala Val Ser Glu Gly Met Ser Thr Val Asp Leu Pro Lys Asp
        530                 535                 540
Asp Ala Lys Leu Lys Glu Trp Ile Ile Glu Arg Glu Trp Asn Pro Glu
545                 550                 555                 560
Tyr Lys Pro Phe Val
            565
```